(12) United States Patent
Ramsburg et al.

(10) Patent No.: US 11,958,889 B2
(45) Date of Patent: *Apr. 16, 2024

(54) COMPOSITIONS OF PHOSPHORYLATED TAU PEPTIDES AND USES THEREOF

(71) Applicants: Janssen Pharmaceuticals, Inc., Titusville, NJ (US); AC Immune SA, Lausanne (CH)

(72) Inventors: Elizabeth Anne Ramsburg, Chalfont, PA (US); Donata de Marco, Turnhout (BE); Charlotte Sadaka, San Diego, CA (US); Jaap Goudsmit, Amsterdam (NL); Andreas Muhs, Cugy (CH); Maria Pihlgren Bosch, Mont-sur-Lausanne (CH); Marija Vukicevic Verhille, St-Sulpice (CH); David Hickman, St-Sulpice (CH); Nicolas Piot, Grandvaux (CH); Saroj Raj Ghimire, Chavannes-Pres-Renens (CH)

(73) Assignees: Janssen Pharmaceuticals, Inc., Titusville, NJ (US); AC Immune SA, Lausanne (CH)

( * ) Notice: Subject to any disclaimer, the term of this patent is extended or adjusted under 35 U.S.C. 154(b) by 287 days.

This patent is subject to a terminal disclaimer.

(21) Appl. No.: 16/757,621

(22) PCT Filed: Oct. 24, 2018

(86) PCT No.: PCT/US2018/057286
§ 371 (c)(1),
(2) Date: Apr. 20, 2020

(87) PCT Pub. No.: WO2019/084118
PCT Pub. Date: May 2, 2019

(65) Prior Publication Data
US 2020/0376078 A1     Dec. 3, 2020

Related U.S. Application Data

(60) Provisional application No. 62/577,157, filed on Oct. 25, 2017.

(51) Int. Cl.
*C07K 14/47* (2006.01)
*A61K 9/127* (2006.01)
(Continued)

(52) U.S. Cl.
CPC .......... *C07K 14/4711* (2013.01); *A61K 9/127* (2013.01); *A61K 9/1271* (2013.01);
(Continued)

(58) Field of Classification Search
None
See application file for complete search history.

(56) References Cited

U.S. PATENT DOCUMENTS 5,843,779 A   12/1998   Vandermeeren et al.
6,444,793 B1   9/2002   Pepinsky et al.
(Continued)

FOREIGN PATENT DOCUMENTS

CN   105121465 A   12/2015
EA      003739 B1    8/2003
(Continued)

OTHER PUBLICATIONS

Asuni et al., "Immunotherapy Targeting Pathological Tau Conformers in a tangle Mouse Model Reduces Brain Pathology with Associated Functional Improvements," Journal of Neuroscience, vol. 27, No. 34, pp. 9115-9129 (2007).
(Continued)

*Primary Examiner* — Michelle S Horning
(74) *Attorney, Agent, or Firm* — Ice Miller LLP

(57) ABSTRACT

Liposomes containing tau peptides, preferably phosphorylated tau peptides, and conjugates containing tau peptides,
(Continued)

preferably phosphorylated tau peptides, conjugated to an immunogenic carrier are described. Pharmaceutical compositions and uses of the liposomes and/or conjugates for treating or preventing a neurodegenerative disease or disorder, such as Alzheimer's Disease, are also described.

24 Claims, 18 Drawing Sheets

Specification includes a Sequence Listing.

(51) Int. Cl.
 *A61K 38/17* (2006.01)
 *A61K 39/00* (2006.01)
 *A61K 39/39* (2006.01)
 *A61P 25/28* (2006.01)

(52) U.S. Cl.
 CPC ...... *A61K 38/1709* (2013.01); *A61K 39/0007* (2013.01); *A61K 39/39* (2013.01); *A61P 25/28* (2018.01); *A61K 2039/55516* (2013.01); *A61K 2039/55555* (2013.01); *A61K 2039/55561* (2013.01); *A61K 2039/55572* (2013.01); *A61K 2039/6018* (2013.01); *A61K 2039/627* (2013.01)

(56) References Cited

U.S. PATENT DOCUMENTS

| | | | |
|---|---|---|---|
| 7,408,027 | B1 | 8/2008 | Mandelkow et al. |
| 7,741,297 | B2 | 6/2010 | Jiang et al. |
| 8,647,631 | B2 | 2/2014 | Pfeifer et al. |
| 9,687,447 | B2 | 6/2017 | Reis et al. |
| 10,889,638 | B2 | 1/2021 | Barbour |
| 11,124,552 | B2 * | 9/2021 | Ramsburg ............ A61K 39/39 |
| 2001/0025320 | A1 | 9/2001 | Seng et al. |
| 2002/0086009 | A1 | 7/2002 | Ishiguro et al. |
| 2003/0232758 | A1 | 12/2003 | St George-Hyslop |
| 2004/0265920 | A1 | 12/2004 | Seubert et al. |
| 2005/0038239 | A1 | 2/2005 | Catchpole |
| 2005/0182295 | A1 | 8/2005 | Soper et al. |
| 2005/0221391 | A1 | 10/2005 | Davies |
| 2005/0261475 | A1 | 11/2005 | Tseng et al. |
| 2006/0073158 | A1 | 4/2006 | Nicolau et al. |
| 2008/0050383 | A1 | 2/2008 | Sigurdsson et al. |
| 2008/0220449 | A1 | 9/2008 | Vasan et al. |
| 2009/0098155 | A1 | 4/2009 | Garsky et al. |
| 2010/0316564 | A1 | 12/2010 | Sigurdsson et al. |
| 2012/0183599 | A1 | 7/2012 | Pfeifer |
| 2012/0322991 | A1 | 12/2012 | Montefeltro et al. |
| 2013/0022982 | A1 | 1/2013 | Wang et al. |
| 2014/0294713 | A1 | 10/2014 | Saito et al. |
| 2014/0314837 | A1 | 10/2014 | Pfeifer et al. |
| 2016/0008443 | A1 | 1/2016 | Mandler et al. |
| 2016/0031976 | A1 | 2/2016 | Seubert et al. |
| 2016/0031978 | A1 | 2/2016 | Brady et al. |
| 2016/0347804 | A1 | 12/2016 | Griswold-Prenner |
| 2017/0106063 | A1 | 4/2017 | Blackburn et al. |
| 2018/0240237 | A1 | 8/2018 | Donhowe et al. |
| 2019/0112362 | A1 | 4/2019 | Adolfsson |
| 2019/0119341 | A1 | 4/2019 | Ramsburg |
| 2020/0253873 | A1 * | 8/2020 | Pfeifer ............ A61K 39/0007 |
| 2020/0339643 | A1 | 10/2020 | Ramburg et al. |
| 2020/0376078 | A1 | 12/2020 | Ramsburg |
| 2021/0388044 | A1 | 12/2021 | Ramburg et al. |

FOREIGN PATENT DOCUMENTS

| | | | |
|---|---|---|---|
| EP | 2210901 | A1 | 7/2010 |
| EP | 2269633 | A1 | 1/2011 |
| JP | 5819401 | B2 | 11/2015 |
| TW | 461209 | B | 10/2001 |
| WO | 9014837 | A1 | 12/1990 |
| WO | 1996020218 | A1 | 7/1996 |
| WO | 1997034145 | A1 | 9/1997 |
| WO | 1998022120 | A1 | 5/1998 |
| WO | 2003066649 | A1 | 8/2003 |
| WO | 2004058258 | A1 | 7/2004 |
| WO | 2005080986 | A1 | 9/2005 |
| WO | 2005081872 | A2 | 9/2005 |
| WO | 2007068105 | A1 | 6/2007 |
| WO | 2007068411 | A2 | 6/2007 |
| WO | 2007098607 | A1 | 9/2007 |
| WO | 2010088411 | A2 | 8/2010 |
| WO | 2010106127 | A2 | 9/2010 |
| WO | 2010115843 | A2 | 10/2010 |
| WO | 2010144711 | A2 | 12/2010 |
| WO | 2011013034 | A1 | 2/2011 |
| WO | 2012020124 | A1 | 2/2012 |
| WO | 2012055933 | A1 | 5/2012 |
| WO | 2013041962 | A1 | 3/2013 |
| WO | 2014031694 | A2 | 2/2014 |
| WO | 2015197823 | A2 | 12/2015 |
| WO | 2017011590 | A1 | 1/2017 |
| WO | 2018106781 | A1 | 6/2018 |
| WO | 2019084118 | A2 | 5/2019 |
| WO | 2019094595 | A2 | 5/2019 |
| WO | 2020219646 | A1 | 10/2020 |

OTHER PUBLICATIONS

Bhaskar et al., "Tyrosine Phosphorylation of Tau Accompanies Disease Progression in Transgenic Mouse Models of Tauopathy," Neuropathology and Applied Neurobiology, vol. 36, No. 6, pp. 462-477 (2012).

Boimel et al., "Efficacy and safety of immunization with phosphorylated tau against neurofibrillary tangles in mice," Experimental Neurology, vol. 224, pp. 472-485 (2010).

Clinical Trials, "Safety Study of AADvac1, a Tau Peptide-KLH-Conjugate Active Vaccine to Treat Alzheimer's Disease", https://www.clinicaltrials.gov/ct2/show/record/nct018502387view=record, ClinicalTrials.gov Identifier: NCT01850238, Oct. 2015.

De Titta et al., "Nanoparticle Conjungation of CpG Enhances Adjuvancy from Cellular Immunity and Memory Recall at Low Dose", PNAS, vol. 110, No. 49, pp. 19902-19907 (2013).

Dominguez et al., "Novel Thereapeutic Strategies Provide the Real Test for the Amyloid Hypothesis Alzheimer's Disease," Trends in Pharmacological Sciences, vol. 23, No. 7, pp. 324-330 (2002).

Friedhoff et al., "Structure of tau protein and assembly into paired helical filaments", Biochimica et Biophysica Acta, 1502, pp. 122-132, 2000.

Gandhi et al., "A Phosphorylation-Induced Turn Defines the Alzheimer's Disease AT8 Antibody Epitope on the Tau Protein," Angew Chem Int Ed Engl, vol. 54, No. 23, pp. 6819-6823 (2015).

Hanger et al., "Tau phosphorylation: the therapeutic challenge for neurodegenerative disease" Trends in Molecular Medicine, vol. 15, No. 3, pp. 112-119 (2009).

Hickman et al., "Sequence-independent Conftrol of Peptide Conformation in Liposomal Vaccines for Targeting Protein Misfolding Diseases," The Journal of Biological Chemistry, vol. 286, No. 16, pp. 13966-13976 (2011).

Hills et al., "A Rapid-Response Humoral Vaccine Platform Exploiting pre-Existing Non-Cognate Populations of Anti-Vaccine or Anti-Viral CD4+ T Helper Cells to confirm B Cell Activation," PLOS One, 20 pages, Nov. 18, 2016.

Hirata-Fukae et al., "Levels of Soluble and Insoluble Tau Reflect Overall Status of Tau Phosphorylation in Vivo," Neuroscience Letters, vol. 450, No. 1, pp. 51-55 (2009).

Hoffman et al., "Unique Alzheimer's Disease Paired Helical Filament Specific Epitopes Involve Double Phosphorylation at Specific Sites," Biochemistry, vol. 36, No. 26, pp. 8114-8124 (1997).

Jicha et al., "Camp-Dependent Protein Kinase Phosphorylations on Tau in Alzheimer's Disease," Journal of Neuroscience, vol. 19, No. 17, pp. 7486 (1999).

Kontsekova et al., "Identification of structural determinants on tau protein essential for its pathological function: novel therapeutic

(56) References Cited

OTHER PUBLICATIONS target for tau immunotherapy in Alzheimer's Disease," Alzheimer's research & therapy, vol. 6, No. 45, pp. 1-16 (2014).
Lee et al., "Phosphorylation of Tau by Fyn: Implications for Alzheimer's Disease," Journal of Neuroscience, Mar. 3, 2004, vol. 24, No. 9, pp. 2304-2312.
Lewis et al., "Neurofibrillary Tangles, Amyotrophy and Progressive Motor Disturbance in Mice Expressing Mutant (P301L) Tau Protein," Nature America, Inc., vol. 25, pp. 402-405 (2000).
Lichtenberg-Kraag et al., "Phosphorylation-Dependent Epitopes of Neurofilament Antibodies on Tau Protein and Relationship with Alzheimer Tau," PNAS, vol. 89, No. 12, pp. 5384-5388 (1992).
Masliah et al., "Effects of a-Synuclein Immunization in a Mouse Model of Parkinson's Disease," Neuron, vol. 46, pp. 857-868 (2005).
Matyas et al., "Liposomes containing monophosphoryl lipid A: A Potent adjuvant system for inducing antibodies to heroin hapten analogs", Vaccine, vol. 21, pp. 2804-2810 (2013).
Muhs et al., "Liposomal Vaccines with Conformation-Specific Amyloid Peptide Antigens Define Immune Response and Efficacy in APP Transgenic Mice," PNAS, vol. 104, No. 23, pp. 9810-9815 (2007).
Muyllaert et al., "Glycogen Synthase Kinase-3p, or a Link Between Amyloid and Tau Pathology?" Genes, Brain and Behavior, vol. 7, Suppl. 1, pp. 57-66 (2008).
Muyllaert et al., "Transgenic Mouse Models for Alzheimer's Disease: the Role of GSK-3p in Combined Amyloid and Tau-Pathology," Rev Neurol (Paris), vol. 162, No. 10, pp. 903-907 (2006).
Nakamura et al., "Cisphosphorylated tau as the earliest detectable pathogenic conformation in Alzheimer disease, offering novel diagnostic and therapeutic strategies," Prion, vol. 7, No. 2, pp. 117-120 (2013).
Neeland et al., "Incorporation of CpG into a Liposomal Vaccine Formulation Increases the Maturation of Antigen-Loaded dendritic Cells and Monocytes to Improve Local and Systemic Immunity", Journal of Immunology, vol. 192, pp. 3666-3675 (2014).
Nicolau et al., "A Liposome-Based Therapeutic Vaccine Against (3-Amyloid Plaques on the Pancreas of Transgenic Mice," PNAS, vol. 99, No. 4, pp. 2332-2337 (2012).
Nicoll et al., "Neuropathology of Human Alzheimer Disease After Immunization with Amyloid—p Peptide: A Case Report," Nature Medicine, vol. 9, No. 4, pp. 448-452 (2003).
Novak et al., "Characterisation of the Antibody Response to Aadvac1: The First-in-Kind Active Vaccine Against Neurofibrillary Tau Pathology", Alzeheimer's & Dementia: The Journal of the Alzheimer's Association, vol. 12, No. 7, pp. P351 (2016).
Novak et al., "Safety and immunogenicity of the tau vaccine AADvac1 in patients with Alzheimer's disease: randomised, double-blind, placebo-controlled, phase 1 trail," Lancet Neurol, vol. 16, pp. 123-134 (2017).
Oddo et al., "A-beta Immunotherapy Leads to Clearance of Early, but Not Late, Hyperphosporylated Tau Aggregates via the Proteasome," Neuron, vol. 43, pp. 321-332 (2004).
Oddo et al., "Reduction of Soluble Abeta and Tau, but Not Soluble Abeta Alone, Ameliorates Cognitive Decline in Transgenic Mice with Plaques and Tangles," Journal of Biological Chemistry, vol. 281, No. 51, pp. 39413-39423 (2006).
Otvos et al., "Monoclonal Antibody PHF4 Recognizes Tau Protein Phosphorylated at Serine Residues 396 and 404," Journal of Neuroscience Research, vol. 39, pp. 669-673 (1994).
Ribe et al., "Accelerated Amyloid Deposition, Neurofibrillary Degeneration and Neuronal Loss in Double Mutant APP/TAU Transgenic Mice," Neurobiology of Disease, vol. 20, pp. 814-822 (2005).
Richter et al., "Doubly Phosphorylated Peptide Vaccines to Protect Transgenic P301S Mice against Alzheimer's Disease Like Tau Aggregation", Vaccines, vol. 2, pp. 601-623 (2014).
Ries et al., "Convenient synthesis and application of versatile nucleic acid lipid membrane anchors in the assembly and fusion of liposomes", Organic & Biomolecular Chemistry, vol. 13, pp. 9673-9680 (2015).
Roberson et al., "Reducing Endogenous Tau Ameliorates Amyloid (3-Induced Deficits in an Alzheimer's Disease Mouse Model," Science, vol. 316, pp. 750-754 (2007).
Roder et al., "Phosphorylation-Dependent Monoclonal Tau Antibodies Do Not Reliably Report Phosphorylation by Extracellular Signal-Regulated Kinase 2 at Specific Sites," Journal of Biological Chemistry, vol. 272, No. 7, pp. 4509-4515 (1997).
Roman et al., "Therapeutic Vaccination Using Cationic Liposome-Adjuvanted HIV Type 1 Peptides Representing HLA-Supertype-Restricted Subdominant T Cell Epitopes: Safety, Immunogenicity, and Feasibility in Guinea-Bissau," AIDS Research and Human Retroviruses, vol. 29, No. 11, pp. 1504-1512 (2013).
Rosenmann et al., "Tauopathy-Like Abnormalities and Neurologic Deficits in Mice Immunized with Neuronal Tau Protein," Arch Neurol, vol. 63, pp. 1459-1467 (2006).
Rueda et al., "Effect of TLR ligands co-encapsulated with multiepitopic antigen in nanoliposomes tartgeted to human DCs via Fc receptor for cancer vaccines," Immunobiology, vol. 222, pp. 989-997 (2017).
Sela et al., "Therapeutic Vaccines: Realities of Today and Hopes for the Future," Drug Discovery Today—Reviews, Therapeutic Focus, vol. 7, No. 12, pp. 664-673 (2002).
Singer et al., "Characterization of Phosphorylation Dependent Antibodies to Study the Phosphorylation Dependent Antibodies to Study the Phosphorylation Status of the Tau Protein," International Journal of Peptide Research and Therapeutics (formerly known as Letters in Pepdtide Science), vol. 11, No. 4, pp. 279-289 (2005).
Singer et al., "Immuno-PCR-Based Quantification of Multiple Phosphorylated Tau-Epitopes Linked to Alzheimer's Disease," Analytical and Bioanalytical Chemistry, vol. 395, No. 7, pp. 2263-2267 (2009).
Tabira, "Immunization Therapy for Alzheimer Disease: A Comprehensive Review of Active Immunization Strategies," Tohoku J. Exp. Med., vol. 220, pp. 95-106 (2010).
Terwel et al., "Amyloid Activates GSK-3p to Aggravate Neuronal Tauopathy in Bigenic Mice," The American Journal of Pathology, vol. 172, No. 3, pp. 786-798 (2008).
Theunis et al., "Efficacy and Safety of a Liposome-Based vaccine against Protein Tau, Assessed in Tau. P301 L Mice That Model Tauopathy," PLOS ONE, vol., 8, Issue 8, pp. e72301, 13 pages (2013).
Theunis et al., "Novel Phospho-Tau monoclonal Antibody Generated Using a Liposomal Vaccine, with Enhanced Recognition of Conformational Tauopathy Epitope", Journal of Alzheimer's Disease, vol. 56, No. 2, pp. 585-599 (2017).
Torreilles et al., "Binding Specificity of Monoclonal Antibody AD2: Influence of the Phosphorylation State of Tau," Molecular Brain Research, vol. 78, pp. 181-185 (2001).
Vanhelmont et al., "Serine-409 Phosphorylation and Oxidative Damage Define Aggregation of Human Protein Tau in Yeast," Fems Yeast Research, vol. 10, No. 8, pp. 992-1005 (2010).
Zemlan et al., "Monoclonal Antibody PHF-9 Recognizes Phosphorylated Serine 404 of Tau Protein and Labels Paired Helical Filaments," Journal of Neuroscience Research, vol. 46, No. 1, pp. 90-97 (1996).
Zheng-Fischhoefer et al., "Sequential Phosphorylation of Tau by Glycogen Synthase Kinase-3beta and Protein Kinase A at Thr212 and Ser214 Generates the Alzheimer-Specific Epitope of Antibody AT100 and Requires a Paired-Helical-Filament-Like Conformation," European Journal of Biochemistry, vol. 252, No. 3, pp. 542-552 (1998).
International Search Report dated May 8, 2019 in International Application No. PCT/US2018/057286.
Lu, Shan. Heterologous prime-boost vaccination. Curr. Opin. Immunol. 2009, 21(3):346-351. (Year: 2009).
Sigurdsson, Einar M., "Tau Immunotherapy", Neurodegener Dis., 16(0), 34-38, 2016.
Novak, Petr, et al., "Fundamant: an interventional 72-week phase 1 follow-up study of AADvad1, an active immunotherapy against tau protein pthology in Alzheimer's disease", Alzheimer's Research & Therapy, 10:108, 2018.

(56) References Cited

OTHER PUBLICATIONS

Dubois, Bruno, et al., "Preclinical Alzheimer's disease: Definition, natural history, and diagnostic criteria", Alzheimers Dement. 12(3), 292-323, 2016.
Dubois, Bruno, et al., "Advancing research diagnostic criteria for Alzheimer's disease: the IWG-2 criteria", Lancet Neurol, 13, 614-629, 2014.
Jack, Jr., Clifford R., et al., "NIA-AA Research Framework: Toward a biological definition of Alzheimer's disease", Alzheimer's & Dementia, 14, 535-562, 2018.
Orgogozo, M.D., J.M., et al., "Subacute meningoencephalitis in a subset of patients with AD after AB42 immunization", Neurology 61, 46-54, 2003.
Novak, Petr, et al., "Ten Years of Tau-Targeted Immunotherapy: The Path Walked and the Roads Ahead", Front. Neurosci., 12, 798, 2018.
Rosenmann, Hanna, "Immunotherapy for Targeting Tau Pathology in Alzheimer's Disease and Tauopathier", Current Alzheimer Research, 10, 217-228, 2013.
Alving C R, "Antibodies To Liposomes Phospholipids and Phosphate Esters", Chemistry and Physics of Lipids, (1986), vol. 40, No. 2-4, doi:doi:10.1016/0009-3084(86)90075-7, ISSN 0009-3084, pp. 303-314, XP025418929.
Andronesi Ovidiu C et al, "Characterization of Alzheimer's-like paired helical filaments from the core domain of tau protein using solid-state NMR spectroscopy", Journal of the American Chemical Society, (May 2008), vol. 130, No. 18, ISSN 0002-7863, pp. 5922-5928.
Boutajangout Allal et al., "Immunotherapy Targeting Pathological Tau Prevents Cognitive Decline in a New Tangle Mouse Model", Journal of Neuroscience, (Dec. 2010), vol. 30, No. 49, doi:doi:10.1523/JNEUROSCI.4363-10.2010, ISSN 0270-6474, pp. 16559-16566, XP055203597.
Wassef N M et al, "Phosphate-Binding Specificities of Monoclonal Antibodies Against Phosphoinositides in Liposomes", Molecular Immunology, (1984), vol. 21, No. 10, doi:doi:10.1016/0161-5890(84)90140-8, ISSN 0161-5890, pp. 863-868, XP023786303.
Bentebibel et al., "Induction of ICOS+CXCR3+CXCR5+ Th Cells Correlates with Antibody Responses to Influenza Vaccination," Mar. 2013, Science Translational Medicine, vol. 5, issue 176, pp. 176ra32, DOI: 10.1126/scitranslmed.3005191.
Crotty, Shane, "Follicular helper CD4 T cells (Tfh)," Apr. 2011, Annual Review of Immunology, vol. 29, pp. 621-663.
Greenberg et al. "A preparation of Alzheimer paired helical filaments that displays distinct tau proteins by polyacrylamide gel electrophoresis," Aug. 1990, Proceedings of the National Academy of Sciences of the United States of America, vol. 87, issue 15, pp. 5827-5831.
Peeraer et al., "Intracerebral injection of preformed synthetic tau fibrils initiates widespread tauopathy and neuronal oss in the brains of tau transgenic mice," Jan. 2015, Neurobiology of Disease, vol. 73, pp. 83-95.
Spensier et al., "Human circulating influenza-CD4+ ICOS1+IL-21+ T cells expand after vaccination, exert helper function, and predict antibody responses," Aug. 2013, Proceedings of the National Academy of Sciences of the United States of America, vol. 110, issue 35, pp. 14330-14335.

Davtyan, Hayk, et al., "MultiTEP platform-based AD epitope vaccine activates broad repertoire of T helper cells in non-human primates", Alzheimers Dement. 10;3, 271-283, 2014.
Davtyan, H. et al., Alzheimer's disease Advax(CpG)—adjuvanted MultiTEP-based dual and single vaccines induce high-titer antibodies against various forms of tau and Aß pathological molecules, Scientific Reports ,2016, vol. 6, 28912, doi:10.1038/srep28912.
International Search Report and Written Opinion for App. No. PCT/US2022/074902, dated Jan. 18, 2023, 15 pages.
Study: ACI-35-LEGOO5-002 "Specificity of the ACI-35 immunogenicity in TPLH mice tested on different phospho- and non-phospho-Tau peptides," AC Immune, pp. 1-8.
Dick, Fritz "Acid CleavagefDeprotection in Fmoc/tBu Solid-Phase Peptide Synthesis," Methods in Molecular Biology, vol. 35 (1994) pp. 63-72.
Smet, Caroline "Theses," In Docteur DE L'Universite De, Absract Only (Oct. 18, 2004).
Smet, Caroline et al. "The Peptidyl Prolyl cis/trans-Isomerase Pin1 Recognizes the Phospho-Thr212-Pro213 Site on Tau," Biochemistry, vol. 43 (2004) pp. 2032-2040.
Jovanovic, Jasmina N., "Chapter 4 Phosphorylation Site-Specific Antibodies as Research Tools in Studies of Native GABA Receptors,", NCBI Bookshelf. A service of the National Library of Medicine, National Institutes of Health (2006) 17 pages.
Iqbal, Khalid et al. "Tau Pathology in Alzheimer Disease and other Tauopathies," Biochimica et Biophysica Acta, vol. 1739 (2005) pp. 198-210.
Hermanson, Greg T. "Chapter 6: Heterobifunctional Crosslinkers," Bioconjugate Techniques, 3rd Edition, Elsevier Science & Technology (2013) pp. 299-339.
Berg, Leonard, "Clinical Dementia Rating (CDR)," Psychopharmacol Bull. 1988;24(4):637-639.
Kwong, Brandone et al., "Induction of potent anti-tumor responses while eliminating systemic side effects via liposome-anchored combinatorial immunotherapy," Biomaterials, vol. 32, issue 22 (Aug. 2011) pp. 5134-5147.
Novak, Petr et al., "ADAMANT: a placebo-controlled randomized phase 2 study of AADvac1, an active immunotherapy against pathological tau in Alzheimer's disease," Nature Aging, vol. 1 (Jun. 2021) pp. 521-534.
Alving, Carl R., et al., "Lipid A and liposomes containing lipid A as antigens and adjuvants," Journal of Vaccine, vol. 26 (2008) pp. 3036-3045.
Brumbaugh, Kathy et al., "Overview of the Generation, Validation, and Application of Phosphosite-Specific Antibodies," Signal Transduction Immunohistochemistry: Methods and Protocols, Methods in Molecular Biology, vol. 717 (2011) pp. 3-43.
Vassilakopoulou, Vyronia et al. "Peptide-Based Vaccines For Neurodegenerative Diseases: Recent Endeavors And Future Perspectives," Journal of Vaccines, vol. 9, (2021) pp. 1-27.
Archuleta, Amy et al., "Optimized Protocol to Make Phospho-Specific Antibodies that Work," Methods in Molecular Biology, vol. 717 (Jan. 2011) pp. 69-88. Abstract Only.
Zaman, Mehfuz et al. "Novel platform technology for modular mucosal vaccine that protects against *streptococcus*," Scientific Reports, vol. 6, issue 39274 (2016) pp. 1-11.

\* cited by examiner

COMPOSITIONS OF PHOSPHORYLATED TAU PEPTIDES AND USES THEREOF

CROSS-REFERENCE TO RELATED APPLICATION

This application is a Section 371 of International Application No. PCT/US2018/057286, filed on Oct. 24, 2018, published in the English language on May 2, 2019, under International Publication No. WO 2019/084118 A2, which claims priority to U.S. Provisional Application No. 62/577,157, filed on Oct. 25, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "065794_2US3_Sequence_Listing" and a creation date of Apr. 17, 2020 and having a size of 23 KB. The sequence listing submitted via EFS-Web is part of the specification and is herein incorporated by reference in its entirety.

FIELD OF THE INVENTION

The present invention is in the field of medicine. The invention in particular relates to liposomes or conjugates of tau peptides and the use thereof for preventing or treating tauopathy, such as Alzheimer's disease.

BACKGROUND

Alzheimer's disease (AD) is a progressive debilitating neurodegenerative disease that affects an estimated 44 million people worldwide (Alzheimers.net). AD therapies that are currently available in the clinic aim to slow the progression of clinical symptoms, but do not target the pathogenic processes that underlie the disease. Unfortunately, these therapies are only minimally efficacious, and there is therefore an urgent need to develop and test additional preventive and therapeutic measures.

The hallmark pathologies for Alzheimer's disease are an accumulation of extracellular plaques comprising aggregated amyloid beta protein and intracellular "tangles" or aggregations of hyperphosphorylated tau protein. The molecular events that lead to accumulation of these proteins are poorly characterized. For amyloid, it is hypothesized that aberrant cleavage of the amyloid precursor protein leads to an accumulation of the aggregation-prone fragment comprising amino acids 1-42. For tau, it is hypothesized that dysregulation of either kinases, phosphatases, or both, leads to aberrant phosphorylation of tau. Once tau becomes hyperphosphorylated it loses the ability to effectively bind and stabilize microtubules, and instead accumulates in the cytoplasm of the affected neuron. The unbound and hyperphosphorylated tau appears to form first oligomers and then higher order aggregates, the presence of which presumably negatively affects function of the neuron in which they form, perhaps via interruption of normal axonal transport.

In developed nations, individuals diagnosed with Alzheimer's disease or other dementing tauopathies are commonly treated with cholinesterase inhibitors (e.g. Aricept®) or memantines (e.g. Namenda™). These drugs, although reasonably well tolerated, have very modest efficacy. For example, Aricept® delays the worsening of symptoms for 6-12 months in approximately 50% of treated individuals. The remainder of treatment is non-pharmacologic, and focuses on making patients more capable of managing day to day tasks as their cognitive ability declines.

Several published studies (Asuni A A et al., J Neurosci. 2007 Aug. 22; 27(34):9115-29., Theunis C et al., PLoS One. 2013; 8(8): e72301., Kontsekova E et al., Alzheimers Res Ther. 2014 Aug. 1; 6(4):44) demonstrate that active vaccines containing tau peptides can induce anti-tau immune responses in mice or rats; reduce the accumulation of pathologic tau aggregates in the brain of rodents; and reduce the rate of progression of cognitive decline in animal models of Alzheimer's disease. An active vaccine against pathological tau proteins was shown to be immunogenic in human patients with Alzheimer's disease (Novak P et al., Lancet Neurology 2017, 16:123-134). WO2010/115843 describes antigenic phosphopeptide mimicking a major pathological phospho-epitope of protein tau and related compositions for the therapeutic and diagnostic use in the treatment of tauopathies including Alzheimer's Disease. However, at present there are still no approved efficacious vaccines on the market to prevent the onset of tau-mediated disease. Neither are there efficacious drugs on the market to intercept or slow the course of disease once it begins. There is therefore a pressing need to identify new preventative measures (e.g. vaccines) that can prevent these diseases.

SUMMARY OF THE INVENTION

In one general aspect, the invention relates to a liposome, comprising:
   a. a tau peptide, preferably the tau peptide is a tau phosphopeptide; and
   b. a helper T-cell epitope,
   wherein the tau peptide is presented on the surface of the liposome.

In one embodiment, the liposome further comprises at least one adjuvant comprising a toll-like receptor ligand. Preferably, the liposome further comprises at least one of a toll-like receptor 4 ligand and a toll-like receptor 9 ligand.

In a preferred embodiment, the invention relates to a liposome, comprising:
   a. a tau peptide, preferably the tau peptide is a tau phosphopeptide;
   b. a helper T-cell epitope; and
   c. at least one of
   i. a toll-like receptor 9 ligand, preferably a lipidated CpG oligonucleotide; and
   ii. a toll-like receptor 4 ligand, preferably a toll-like receptor 4 agonist,
   wherein the tau peptide is presented on the surface of the liposome.

In a further preferred embodiment, the invention relates to a liposome, comprising:
   a. a tau phosphopeptide;
   b. a helper T-cell epitope;
   c. a lipidated CpG oligonucleotide; and
   d. an adjuvant containing a toll-like receptor 4 ligand;
   wherein the tau phosphopeptide is presented on the surface of the liposome.

In another general aspect, the invention relates to a conjugate comprising a tau peptide, preferably a tau phosphopeptide, and an immunogenic carrier conjugated thereto, wherein the tau peptide is conjugated to the carrier via a linker. The linker can comprise one or more of polyethylene glycol (PEG), succinimidyl 3-(bromoacetamido)propionate (SBAP), and m-maleimidobenzoyl-N-hydroxysuccinimide ester (MBS). Examples of the immunogenic carrier useful for the invention include, but are not limited to, keyhole limpet hemocyanin (KLH), tetanus toxoid (TT), CRM197, and an outer membrane protein mixture from *N. meningitidis* (OMP), or a derivative thereof.

In one preferred embodiment, the invention relates to a conjugate having the structure of formula (I):

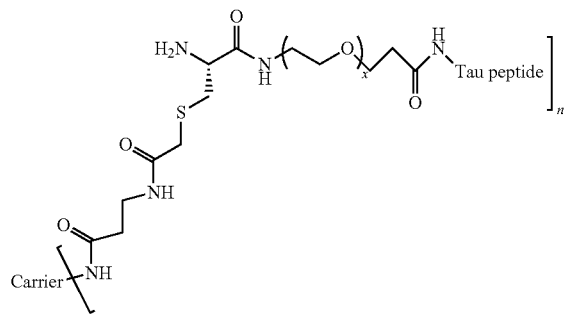

or the structure of formula (II):

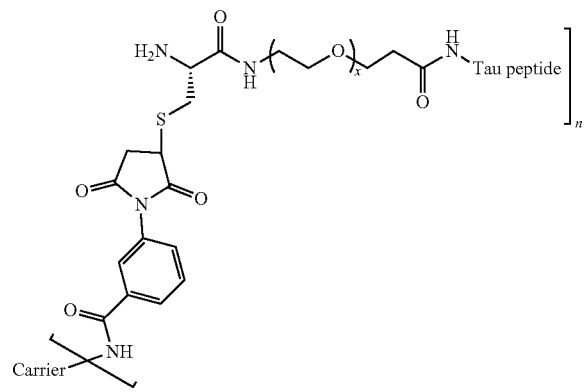

wherein
x is an integer of 0 to 10, preferably 2 to 6, most preferably 3; and
n is an integer of 2 to 11, preferably 3 to 11.

Further aspects of the invention relate to a pharmaceutical composition comprising a liposome or a conjugate of the invention and a pharmaceutically acceptable carrier, methods of preparing the pharmaceutical composition, and the use of the pharmaceutical composition in inducing an immune response against tau, or treating or preventing a neurodegenerative disease or disorder in a subject in need thereof.

In one embodiment, the invention relates to a method for inducing an immune response in a subject suffering from a neurodegenerative disorder, or for treating or preventing a neurodegenerative disease or disorder in a subject in need thereof. The method comprises administering to the subject a pharmaceutical composition comprising a liposome of the invention and a pharmaceutically acceptable carrier, or a pharmaceutical composition comprising a conjugate of the invention and a pharmaceutically acceptable carrier. Preferably, the method comprises administering to the subject a pharmaceutical composition of the invention for priming immunization, and a pharmaceutical composition of the invention for boosting immunization.

Further aspects, features and advantages of the present invention will be better appreciated upon a reading of the following detailed description of the invention and claims.

BRIEF DESCRIPTION OF THE FIGURES

The foregoing summary, as well as the following detailed description of preferred embodiments of the present application, will be better understood when read in conjunction with the appended drawings. It should be understood, however, that the application is not limited to the precise embodiments shown in the drawings.

FIG. 7 shows the titers of anti-phosphorylated tau antibodies in Rhesus macaques induced by liposomal vaccines according to embodiments of the invention, Liposomes X, Y and Z, each of which contains encapsulated T-cell epitope T50 and one or more adjuvants; the titers were measured by ELISA and presented in end point titers over time in individual monkeys. In particular:

FIG. 13 shows that Tau conjugate (KLH-TAUVAC-p7.1 or KLH-TAUVAC-p22.1) induces TfH cells and robust Ab titers against tau peptide in wild-type mice, in particular:

FIG. 13C shows binding titers to the phosphorylated tau peptide p7.1;

FIG. 13D shows binding titers to the phosphorylated tau peptide p22.1;

FIG. 13E shows binding titers to the non-phosphorylated tau peptide 7.1;

FIG. 13F shows binding titers to the non-phosphorylated tau peptide 22.1; and FIGS. 13G and H each show binding titers to the carrier protein KLH;

FIG. 15 shows that vaccine-induced antibodies reduce aggregated tau in an accelerated tauopathy model, in particular:

(p<0.0001, using an ANOVA test followed by Holm-Bonferroni adjustment for multiple comparisons); and FIG. 16 shows that Tau conjugate (Conjugate B) according to an embodiment of the invention induces high titers of antibodies against phosphorylated Tau and ePHF in non-human primates: Rhesus macaques were immunized with alum and CpG adjuvanted KLH-TAUVAC-p7.1 (n=6) or with KLH (n=2) at day 1, 29, 85 and 169; blood was collected every 14 days, in particular:

FIG. 17 shows that mice immunized with a conjugate vaccine (Conjugate A) according to an embodiment of the invention and a combination with alum hydroxide (alum) and oligo CpG (CpG) adjuvant results in higher titer antibody responses to the vaccine peptide: adult female C57BL/6 mice (n=5-6 per group) were immunized intramuscularly with either 2 ug or 0.2 ug of the Conjugate A vaccine, and the conjugate vaccine was either administered alone, with alum, with CpG, or with alum and CpG combined; all mice received a primary immunization on day 0 of the study followed by a single booster immunization on day 28; doses for the alum adjuvant was 500 ug per mouse per injection, and doses for the CpG adjuvant was 20 ug/mouse per injection; the graphs show the results of binding ELISA using serum collected from immunized mice with vaccine peptide T3.5 as the coating antigen, with T3.5 specific mean endpoint titers per group plotted, before immunization (day 0) and at two time points after immunization (day 28 and 42), and with error bars representing standard error; the tables show the statistical analysis of the results, in which antibody titers were compared using the non-parametric Kruskal-Wallis Test, and pairwise group comparisons were assessed using the Wilcoxon Signed Rank test as post-hoc to the Kruskal Wallis test; in particular:

DETAILED DESCRIPTION OF THE INVENTION

Figure 1:
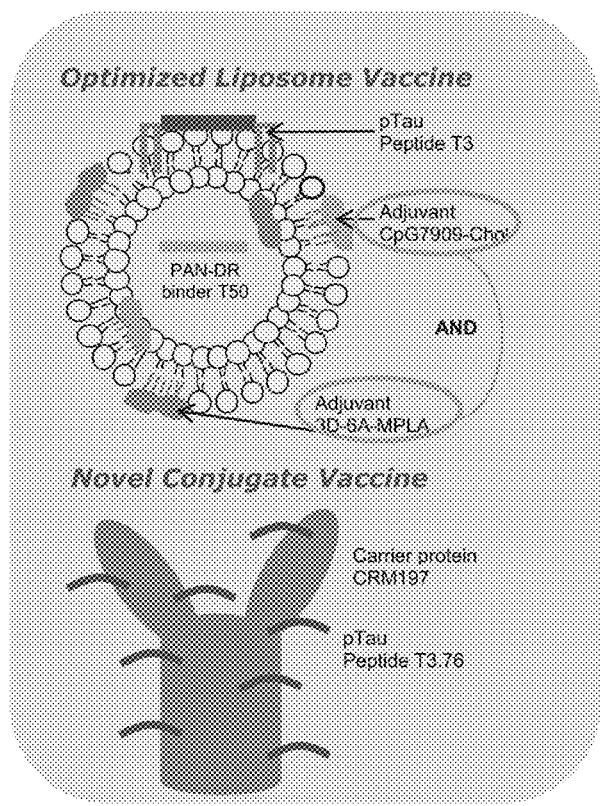
FIG. 1 illustrates novel vaccines according to embodiments of the invention: a tau liposome according to an embodiment of the invention (top), and a tau conjugate according to an embodiment of the invention (bottom)

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

As used herein, the term "tau" or "tau protein", also known as microtubule-associated protein tau, MAPT, neurofibrillary tangle protein, paired helical filament-tau, PHF-tau, MAPTL, MTBT1, refers to an abundant central and peripheral nervous system protein having multiple isoforms. In the human central nervous system (CNS), six major tau isoforms ranging in size from 352 to 441 amino acids in length exist due to alternative splicing (Hanger et al., *Trends Mol Med.* 15:112-9, 2009). Examples of tau include, but are not limited to, tau isoforms in the CNS, such as the 441-amino acid longest tau isoform (4R2N) that has four repeats and two inserts and the 352-amino acid long shortest (fetal) isoform (3R0N) that has three repeats and no inserts. Examples of tau also include the "big tau" isoform expressed in peripheral nerves that contains 300 additional residues (exon 4a). Friedhoff et al., *Biochimica et Biophysica Acta* 1502 (2000) 122-132. Examples of tau include a human big tau that is a 758 amino acid-long protein encoded by an mRNA transcript 6762 nucleotides long (NM_016835.4), or isoforms thereof. The amino acid sequence of the exemplified human big tau is represented in GenBank Accession No. NP_058519.3. As used herein, the term "tau" includes homologs of tau from species other than human, such as Macaca Fascicularis (cynomolgus monkey) or Pan troglodytes (chimpanzee). As used herein, the term "tau" includes proteins comprising mutations, e.g., point mutations, fragments, insertions, deletions and splice variants of full length wild type tau. The term "tau" also encompasses post-translational modifications of the tau amino acid sequence. Post-translational modifications include, but are not limited to, phosphorylation.

As used herein, the term "peptide" or "polypeptide" refers to a polymer composed of amino acid residues, related naturally occurring structural variants, and synthetic non-naturally occurring analogs thereof linked via peptide bonds. The term refers to a peptide of any size, structure, or function. Typically, a peptide is at least three amino acids long. A peptide can be naturally occurring, recombinant, or synthetic, or any combination thereof. Synthetic peptides can be synthesized, for example, using an automated polypeptide synthesizer. Examples of tau peptides include any peptide of tau protein of about 5 to about 30 amino acids in length, preferably of about 10 to about 25 amino acids in length, more preferably of about 16 to about 21 amino acids in length. In the present disclosure, peptides are listed from N to C terminus using the standard three or one letter amino acid abbreviation, wherein phosphoresidues are indicated with "p". Examples of tau peptides useful in the invention include, but are not limited to, tau peptides comprising the amino acid sequence of any of SEQ ID NOs: 1-12, or tau peptides having an amino acid sequence that is at least 75%, 80%, 85%, 90% or 95% identical to the amino acid sequence of any of SEQ ID NOs: 1-12.

As used herein, the term "phosphopeptide" or "phospho-epitope" refers to a peptide that is phosphorylated at one or more amino acid residues. Examples of tau phosphopeptides include any tau peptide comprising one or more phosphorylated amino acid residue. Examples of tau phosphopeptides useful in the invention include, but are not limited to, tau phosphopeptides comprising the amino acid sequence of any of SEQ ID NOs: 1-3 or 5-12, or tau phosphopeptides having an amino acid sequence that is at least 75%, 80%, 85%, 90% or 95% identical to the amino acid sequence of any of SEQ ID NOs: 1-3 or 5-12.

The tau peptides of the present invention can be synthesized by solid phase peptide synthesis or by recombinant expression systems. Automatic peptide synthesizers are commercially available from numerous suppliers, such as Applied Biosystems (Foster City, Calif). Recombinant expression systems can include bacteria, such as *E. coli*, yeast, insect cells, or mammalian cells. Procedures for recombinant expression are described by Sambrook et al., Molecular Cloning: A Laboratory Manual (C.S.H.P. Press, NY 2d ed., 1989).

Tau is a human "self" protein. This means that, in principle, all lymphocytes bearing a receptor specific for tau should have been deleted during development (central tolerance) or rendered unresponsive by a peripheral tolerance mechanism. This problem has proved to be a significant roadblock to the development of vaccines against self or "altered self" proteins (e.g. tumor antigens).

Generating high-quality antibodies against an antigen (self or infectious) requires the action of not only B lymphocytes, which produce the antibody, but also of $CD4^+$ T "helper" lymphocytes. $CD4^+$ T-cells provide critical survival and maturation signals to B lymphocytes, and $CD4^+$ T-cell deficient animals are profoundly immunosuppressed. $CD4^+$ T-cells are also subject to tolerance mechanisms, and an additional roadblock to generating strong anti-self (e.g., anti-tau) antibody responses is that tau-reactive $CD4^+$ T-cells are also likely to be rare to non-existent in the human/animal repertoire.

While not wishing to be bound by theory, it is believed, but in no way limiting the scope of the present invention, that this problem is circumvented by vaccine compositions of the present invention.

Figure 2:
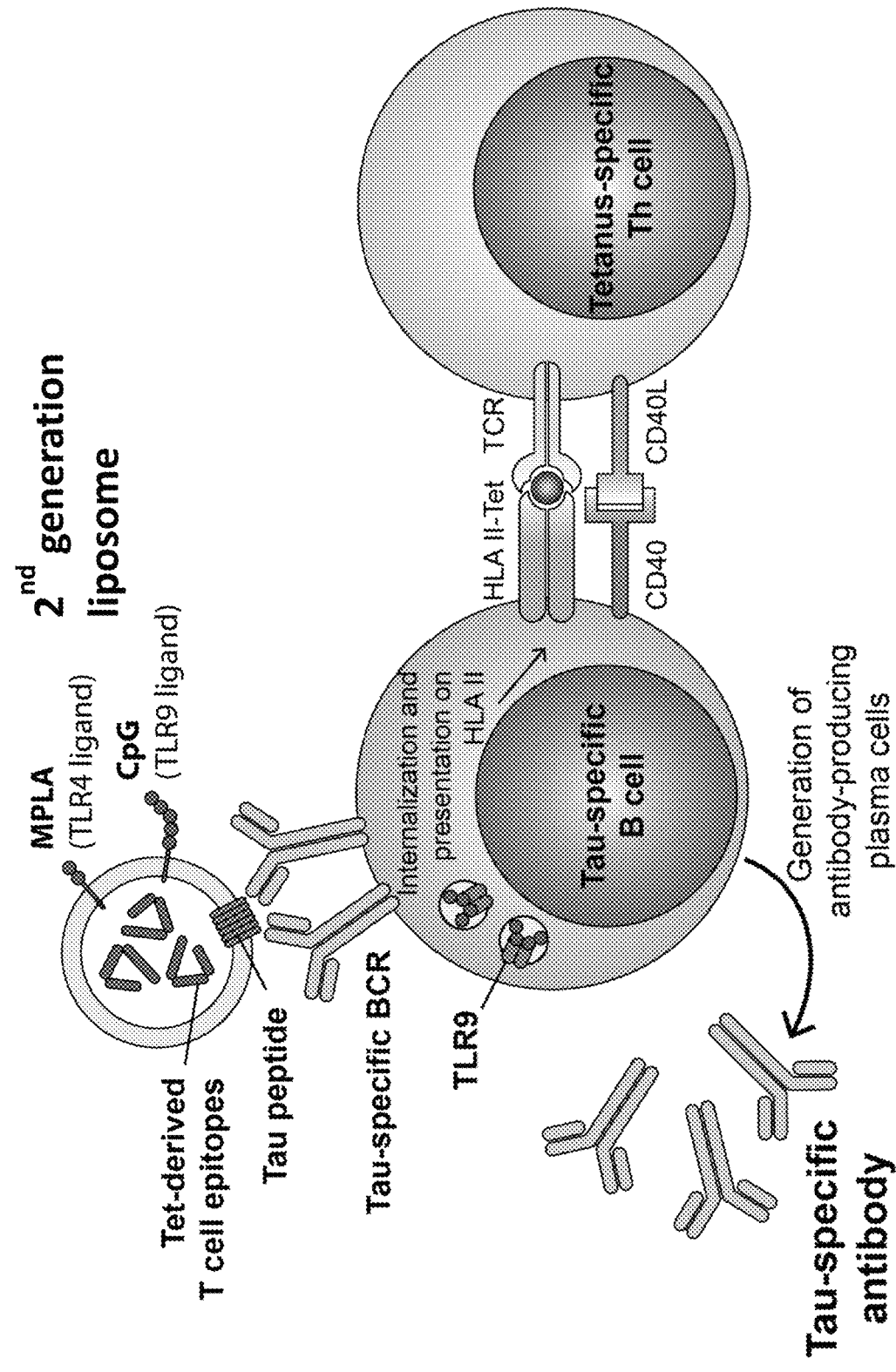
FIG. 2 illustrates that a vaccine comprising a liposome according to an embodiment of the invention (2nd generation liposome) which contains an encapsulated helper T-cell epitope (e.g., tetanus polypeptide (tet)) activates helper T-cells.
Figure 3:
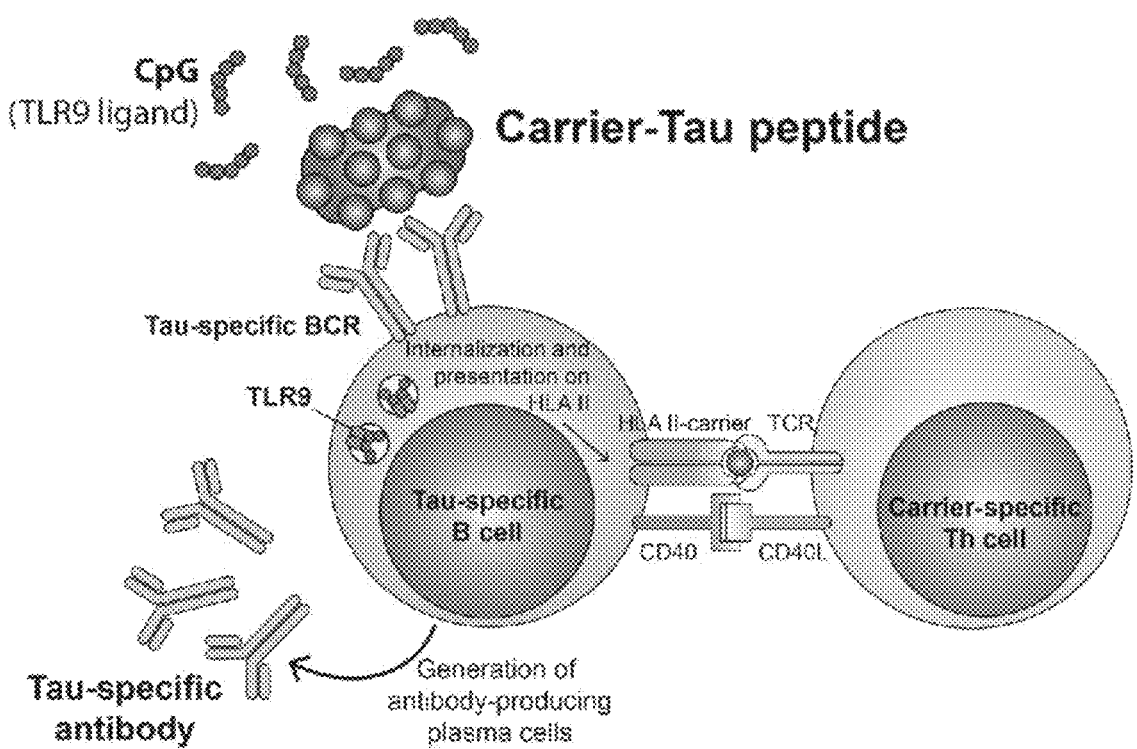
FIG. 3 illustrates that a vaccine comprising a conjugate according to an embodiment of the invention which contains non-self or immunogenic carrier protein activates helper T-cells.

In one embodiment, a liposome comprising a tau peptide (one example is shown in FIG. 1; top) is produced that also comprises a T-cell epitope that is capable of binding most or all HLA DR (Human Leukocyte Antigen—antigen D Related) molecules. The T-cell epitope is then able to activate $CD4^+$ T-cells and provides essential maturation and survival signals to the tau-specific B-cells (FIG. 2). In another embodiment, a conjugate of a tau peptide with a carrier protein is produced (one example is shown in FIG. 1; bottom), which generates a strong helper T-cell response (FIG. 3). In this embodiment "non-linked recognition" is used, in which carrier-specific T-cells provide survival and maturation signals to self-reactive B-cells. Accordingly, the tau-specific B-cells receive crucial signals to trigger affinity maturation, immunoglobulin class switching, and to establish a long-term memory pool. The tau liposomes and tau conjugates can be used to generate high-quality antibodies against the tau antigen in homologous or heterologous immunization schemes, with either liposome or conjugate used in the prime and/or in the boost.

Liposomes

In one general aspect, the invention relates to a liposome, comprising:
 a. a tau peptide, preferably the tau peptide is a tau phosphopeptide; and
 b. a helper T-cell epitope, wherein the tau peptide is presented on the surface of the liposome.

Liposomes according to embodiments of the invention are also referred to herein as "improved liposomes," "improved liposomal vaccines" or "liposomal vaccines according to embodiments of the invention" or "Tau liposomes" or "optimized liposomal vaccines" of "$2^{nd}$ generation liposomes".

As used herein, the term "liposome" refers generally to a lipid vesicle that is made of materials having high lipid content, e.g., phospholipids, cholesterol. The lipids of these vesicles are generally organized in the form of lipid bilayers. The lipid bilayers generally encapsulate a volume which is either interspersed between multiple onion-like shells of lipid bilayers, forming multilamellar lipid vesicles (MLVs) or contained within an amorphous central cavity. Lipid vesicles having an amorphous central cavity are unilamellar lipid vesicles, i.e., those with a single peripheral bilayer surrounding the cavity. Large unilamellar vesicles (LUVs) generally have a diameter of 100 nm to few micrometer, such as 100-200 nm or larger, while small unilamellar lipid vesicles (SUV) generally have a diameter of less than 100 nm, such as 20-100 nm, typically 15-30 mm.

According to particular embodiments, the liposome comprises one or more tau peptides. According to particular embodiments, the tau peptides in the liposome can be the same or different.

Any suitable tau peptide known to those skilled in the art can be used in the invention in view of the present disclosure. According to particular embodiments, one or more of the tau peptides comprise the amino acid sequence of one of SEQ ID NOs: 1-12. In other embodiments, one or more of the tau peptides comprise an amino acid sequence that is at least 75%, 80%, 85%, 90% or 95% identical to the amino acid sequence of one of SEQ ID NOs: 1-12, wherein none of the amino acid residues are phosphorylated, or one or more amino acid residues are phosphorylated.

According to particular embodiments, one or more of the tau peptides is a tau phosphopeptide. According to particular embodiments, the one or more tau phosphopeptides comprise the amino acid sequence of one of SEQ ID NOs: 1-3 or 5-12, or an amino acid sequence that is at least 75%, 80%, 85%, 90% or 95% identical to the amino acid sequence of one of SEQ ID NOs: 1-3 or 5-12, wherein one or more of the indicated amino acid residues are phosphorylated. Preferably, the tau phosphopeptide comprises the amino acid sequence of one of SEQ ID Nos: 1-3. The tau peptide can have the C-terminus amidated.

According to embodiments of the application, a tau peptide is presented on the surface of the liposome. A tau peptide, preferably a tau phosphopeptide, can be presented on the surface of the liposome using methods known in the art in view of the present disclosure. See, for example, the relevant disclosure in U.S. Pat. Nos. 8,647,631 and 9,687, 447, the content of which is incorporated herein by reference. According to particular embodiments, the one or more tau peptides, including phosphopeptides, further comprise one or more modifications, such as palmitoylation or dodecyl modification to allow the tau peptides to be presented on the surface of the liposome. Additional amino acid residues, such as Lys, Cys, or sometimes Ser or Thr, can be added to the tau peptide to facilitate the modification. It was reported that the position of lipid anchors induces different conformations of the peptide sequence (Hickman et al., J. Biol. Chem. vol. 286, NO. 16, pp. 13966-13976, Apr. 22, 2011). While not wishing to be bound by theory, it is believed that adding hydrophobic moieties at both termini may increase the pathological beta-sheet conformation of the tau peptide. Thus, the one or more tau peptides further comprise hydrophobic moieties at both termini. The modified tau peptide can have the C-terminus amidated. Preferably, a tau peptide presented on the surface of the liposome consists of the amino acid sequence of one of SEQ ID NO:27 to SEQ ID NO:38.

As used herein, the term "helper T-cell epitope" refers to a polypeptide comprising an epitope that is capable of recognition by a helper T-cell. Examples of helper T-cell epitopes include, but are not limited to, tetanus toxoid (e.g., the P2 and P30 epitopes, also named, respectively as T2 and T30), Hepatitis B surface antigen, *cholera* toxin B, toxoid, diphtheria toxoid, measles virus F protein, *Chlamydia trachomatis* major outer membrane protein, *Plasmodium falciparum* circumsporozite T, *P. falciparum* CS antigen, *Schistosoma mansoni triose* phosphate isomerase, *Bordetella pertussis, Clostridium tetani, Pertusaria trachythallina, Escherichia coli* TraT, and Influenza virus hemagglutinin (HA).

Any suitable helper T-cell epitope known to those skilled in the art can be used in the invention in view of the present disclosure. According to particular embodiments, the helper T-cell epitope comprises at least one amino acid sequence selected from the group consisting of SEQ ID NO:23 to SEQ ID NO:26. Preferably, the helper T-cell epitope comprises two or more of the amino acid sequences of SEQ ID NO:23 to SEQ ID NO:26 fused together via a linker, such as a peptide linker comprising one or more amino acids, e.g., Val (V), Ala (A), Arg (R), Gly (G), Ser (S), Lys (K). The length of the linker can vary, preferably 1-5 amino acids. Preferably, the helper T-cell epitope comprises three or more of the amino acid sequences of SEQ ID NO:23 to SEQ ID NO:26 fused together via one or more linkers selected from the group consisting of VVR, GS, RR, RK. The helper T-cell epitope can have its C-terminus amidated.

According to embodiments of the application, the helper T-cell epitopes can be incorporated on the liposomal surface, e.g. anchored by a covalently bound hydrophobic moiety wherein said hydrophobic moiety is an alkyl group, a fatty acid, a triglyceride, diglyceride, steroid, sphingolipid, glycolipid or a phospholipid, particularly an alkyl group or a fatty acid, particularly with a carbon backbone of at least 3 carbon atoms, particularly of at least 4 carbon atoms, particularly of at least 6 carbon atoms, particularly of at least 8 carbon atoms, particularly of at least 12 carbon atoms, particularly of at least 16 carbon atoms. In one embodiment of the invention, the hydrophobic moiety is palmitic acid. Alternatively, the helper T-cell epitopes can be encapsulated in the liposomes. According to particular embodiments, the helper T-cell epitope is encapsulated in the liposome.

The helper T-cell epitope can be modified for its desired location in the liposomes using methods known in the art in view of the present disclosure. According to particular embodiments, the helper T-cell epitope useful for the invention comprises an amino acid sequence of one of SEQ ID NO:39 to SEQ ID NO:44. Preferably, the helper T cell epitope consists of an amino acid sequence selected from the group consisting of SEQ ID NO:13 to SEQ ID NO:17.

According to particular embodiments, the liposome comprises a tau peptide and a helper T-cell epitope at a weight ratio of 1:1, 2:1, 3:1, 4:1, 5:1 or 6:1.

In an embodiment, the liposome further comprises at least one adjuvant comprising a toll-like receptor ligand. Thus, in another general aspect, the invention relates to a liposome, comprising:
 a. a tau peptide, preferably a tau phosphopeptide;
 b. a helper T-cell epitope; and c. at least one of
  i. a toll-like receptor 9 ligand, and
  ii. a toll-like receptor 4 ligand.

As used herein, the term "toll-like receptor" or "TLR" refers to a class of pattern recognition receptor (PRR) proteins that play a key role in the innate immune response. TLRs recognize pathogen-associated molecular patterns (PAMPs) from microbial pathogens, such as bacteria, fungi, parasites and viruses, which can be distinguished from host molecules. TLRs are membrane-spanning proteins that typically function as dimers and are expressed by cells involved in the innate immune response, including antigen-presenting dendritic cells and phagocytic macrophages. There are at least ten human TLR family members, TLR1 to TLR10, and at least twelve murine TLR family members, TLR1 to TLR9 and TLR11 to TLR13, and they differ in the types of antigens they recognize. For example, TLR4 recognizes lipopolysaccharides (LPS), a component present in many Gram-negative bacteria, as well as viral proteins, polysaccharide, and endogenous proteins such as low-density lipoprotein, beta-defensins and heat shock protein; and TLR9 is a nucleotide-sensing TLR which is activated by unmethylated cytosine-phosphate-guanine (CpG) single-stranded or double-stranded dinucleotides, which are abundant in prokaryotic genomes but rare in vertebrate genomes. Activation of TLRs leads to a series of signaling events resulting in the production of type I interferons (IFNs), inflammatory cytokines, and chemokines, and the induction of immune responses. Eventually, this inflammation also activates the adaptive immune system, which then results in the clearance of the invading pathogens and the infected cells.

As used herein, the term "ligand" refers to a molecule that forms a complex with a biomolecule (e.g., a receptor) to serve a biological purpose. According to particular embodiments, the toll-like receptor ligand is a toll-like receptor agonist.

As used herein, the term "agonist" refers to a molecule that binds to one or more TLRs and induces a receptor mediated response. For example, an agonist can induce, stimulate, increase, activate, facilitate, enhance, or up regulate the activity of the receptor. Such activities are referred to as "agonistic activities." For example, a TLR4 or TLR9 agonist can activate or increase cell signaling through the bound receptor. Agonists include, but are not limited to nucleic acids, small molecules, proteins, carbohydrates, lipids or any other molecules that bind or interact with receptors. Agonists can mimic the activity of a natural receptor ligand. Agonists can be homologous to these natural receptor ligands with respect to sequence, conformation, charge or other characteristics such that they can be recognized by the receptors. This recognition can result in physiologic and/or biochemical changes within the cell, such that the cell reacts to the presence of the agonist in the same manner as if the natural receptor ligand were present. According to particular embodiments, the toll-like receptor agonist is at least one of a toll-like receptor 4 agonist and a toll-like receptor 9 agonist.

As used herein, the term "toll-like receptor 4 agonist" refers to any compound that acts as an agonist of TLR4. Any suitable toll-like receptor 4 agonist known to those skilled in the art in view of the present disclosure can be used in the invention. Examples of toll-like receptor 4 ligand useful for the invention include TLR4 agonist, including, but not limited to, monophosphoryl lipid A (MPLA). As used herein, the term "monophosphoryl lipid A" or MPLA" refers to a modified form of lipid A, which is the biologically active part of Gram-negative bacterial lipopolysaccharide (LPS) endotoxin. MPLA is less toxic than LPS while maintaining the immunostimulatory activity. As a vaccine adjuvant, MPLA stimulates both cellular and humoral responses to the vaccine antigen. Examples of MPLA include, but are not limited to, 3-O-desacyl-4'-monophosphoryl lipid A, monophosphoryl hexa-acyl lipid A, 3-deacyl, monophosphoryl 3-deacyl lipid A, and structurally related variants thereof. MPLA useful for the invention can be obtained using methods known in the art, or from a commercial source, such as 3D-(6-acyl) PHAD®, PHAD®, PHAD®-504, 3D-PHAD® from Avanti Polar Lipids (Alabaster, Ala., USA) or MPL™ from various commercial sources. According to particular embodiments, the toll-like receptor 4 agonist is MPLA. As used herein, the term "toll-like receptor 9 agonist" refers to any compound that acts as an agonist of TLR9. Any suitable toll-like receptor 9 agonist known to those skilled in the art in view of the present disclosure can be used in the invention. Examples of toll-like receptor 9 ligand useful for the invention include TLR9 agonist including, but not limited to, CpG oligonucleotides.

As used herein, the term "CpG oligonucleotide", "CpG oligodeoxynucleotide" or "CpG ODN" refers to an oligonucleotide comprising at least one CpG motif. As used herein, "oligonucleotide," "oligodeoxynucleotide" or "ODN" refers to a polynucleotide formed from a plurality of linked nucleotide units. Such oligonucleotides can be obtained from existing nucleic acid sources or can be produced by synthetic methods. As used herein, the term "CpG motif" refers to a nucleotide sequence which contains unmethylated cytosine-phosphate-guanine (CpG) dinucleotides (i.e., a cytosine (C) followed by a guanine (G)) linked by a phosphate bond or a phosphodiester backbone or other internucleotide linkages.

According to particular embodiments, the CpG oligonucleotide is lipidated, i.e. conjugated (covalently linked) to a lipid moiety.

As used herein, a "lipid moiety" refers to a moiety containing a lipophilic structure. Lipid moieties, such as an alkyl group, a fatty acid, a triglyceride, diglyceride, steroid, sphingolipid, glycolipid or a phospholipid, particularly a sterol such as cholesterol, or fatty acids, when attached to highly hydrophilic molecules, such as nucleic acids, can substantially enhance plasma protein binding and consequently circulation half-life of the hydrophilic molecules. In addition, binding to certain plasma proteins, such as lipoproteins, has been shown to increase uptake in specific tissues expressing the corresponding lipoprotein receptors (e.g., LDL-receptor HDL-receptor or the scavenger receptor SR-B1). In particular, a lipid moiety conjugated to the phosphopeptides and/or CpG oligonucleotide allows anchoring the said peptides and/or oligonucleotides into the membrane of a liposome via a hydrophobic moiety.

According to particular embodiments, in view of the present disclosure, the CpG oligonucleotide can comprise any suitable internucleotide linkages.

As used herein, the term "internucleotide linkage" refers to a chemical linkage to join two nucleotides through their sugars consisting of a phosphorous atom and a charged or neutral group between adjacent nucleosides. Examples of internucleotide linkage include phosphodiester (po), phosphorothioate (ps), phosphorodithioate (ps2), methylphosphonate (mp), and methylphosphorothioate (rp). Phosphorothioate, phosphorodithioate, methylphosphonate and methylphosphorothioate are stabilizing internucleotide linkages, while phosphodiester is a naturally-occurring internucleotide linkage. Oligonucleotide phosphorothioates are typically synthesized as a random racemic mixture of Rp and Sp phosphorothioate linkages.

Any suitable CpG oligonucleotide known to those skilled in the art can be used in the invention in view of the present disclosure. Examples of such CpG oligonucleotides include, but are not limited to CpG2006 (also known as CpG 7909), CpG 1018, CpG2395, CpG2216 or CpG2336.

A CpG oligonucleotide can be lipidated using methods known in the art in view of the present disclosure. In some embodiments, 3' terminus of a CpG oligonucleotide is covalently linked to a cholesterol molecule through a phosphate bond, optionally via a PEG linker. Other lipophilic moiety can also be covalently linked to the 3' terminus of a CpG oligonucleotide. For example a CpG oligonucleotide can be covalently linked to a lipid anchor of the same length as the phospholipids from liposome: one palmitic acid chain (using Pal-OH or similar, activated for coupling) or two palmitic acids (e.g., using 1,2-dipalmitoyl-sn-glycero-3-phosphoethanolamine-N-(succinyl) or similar, activated for coupling), optionally via a PEG linker. See, e.g., relevant disclosure in U.S. Pat. No. 7,741,297, the content of which is incorporated herein by reference. The length of PEG can vary, from example, from 1 to 5 PEG units.

Other linkers can also be used to covalently connect a CpG oligonucleotide to a lipophilic moiety (such as a cholesterol molecule), examples of which include, but are not limited to an alkyl spacer having 3 to 12 carbons. A short linker compatible with oligonucleotide chemistry is needed as aminodiol. In some embodiment, no linker is used for the covalent bonding. See e.g., Ries et al., "Convenient synthesis and application of versatile nucleic acid lipid membrane anchors in the assembly and fusion of liposomes, *Org. Biomol. Chem.*, 2015, 13, 9673, the relevant disclosure of which is incorporated herein by reference.

According to particular embodiments, lipidated CpG oligonucleotide useful for the invention comprises a nucleotide sequence selected from the group consisting of SEQ ID NO:18 to SEQ ID NO:22, wherein the nucleotide sequence comprises one or more phosphorothioate internucleotide linkages, and the nucleotide sequence is covalently linked to at least one cholesterol via a linker. Any suitable linkers can be used to covalently link a CpG oligonucleotide to a cholesterol molecule. Preferably, the linker comprises polyethylene glycol (PEG).

According to particular embodiments, the liposome comprises:
a. a tau phosphopeptide;
b. a helper T-cell epitope;
c. a lipidated CpG oligonucleotide; and
d. a toll-like receptor 4 ligand;
wherein the tau phosphopeptide is presented on the surface of the liposome, and the helper T-cell epitope is encapsulated in the liposome.

According to particular embodiments, the liposome comprises:
a. a tau peptide having an amino acid sequence selected from the group consisting of SEQ ID NO:27 to SEQ ID NO:38;
b. a helper T cell epitope having an amino acid sequence selected from the group consisting of SEQ ID NO:39 to SEQ ID NO:44, preferably, the helper T cell epitope consisting of an amino acid sequence selected from the group consisting of SEQ ID NO:13 to SEQ ID NO:17;
c. a lipidated CpG oligonucleotide having a nucleotide sequence selected from the group consisting of SEQ ID NO:18 to SEQ ID NO:22, wherein the CpG oligonucleotide comprises one or more phosphorothioate internucleotide linkages, and the CpG oligonucleotide is covalently linked to at least one cholesterol via a linker; and
d. monophosphoryl lipid A (MPLA).

According to particular embodiments, the liposome further comprises one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

According to particular embodiments, the liposome further comprises a buffer. Any suitable buffer known to those skilled in the art in view of the present disclosure can be used in the invention. In one embodiment, the liposome comprises a phosphate-buffered saline. According to particular embodiments, the buffer comprises histidine and sucrose.

According to particular embodiments, the liposome comprises DMPC, DMPG, cholesterol, tau phosphopeptide and helper T-cell epitope at a molar ratio of 9:1:7:0.07:0.04.

Liposomes of the invention can be made using methods known in the art in view of the present disclosure.

An exemplary liposome of the present application is illustrated in FIG. 1. More specifically, a tau tetrapalmitoylated phosphopeptide (pTau Peptide T3, SEQ ID NO: 28) is presented on the surface of the liposome via two palmitic acids at each terminus of the tau peptide. A TLR-9 ligand comprising lipidated CpG (Adjuvant CpG7909-Chol) is incorporated into the liposome membrane via the covalently linked cholesterol. A TLR-4 ligand (Adjuvant 3D-(6-acyl) PHAD®) is also incorporated into the membrane. A helper T-cell epitope (PAN-DR binder T50) is encapsulated.

Conjugates

In one general aspect, the invention relates to a conjugate comprising a tau peptide and an immunogenic carrier conjugated thereto.

According to particular aspects, the conjugate has the following structure:

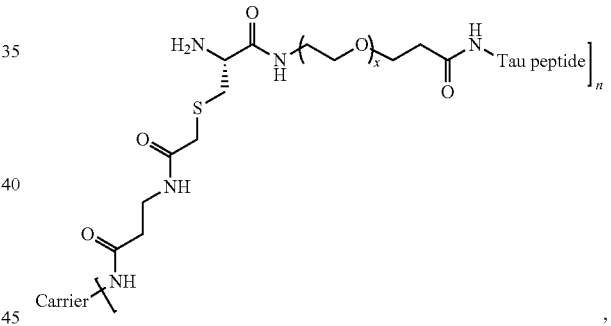

or the structure of formula (II):

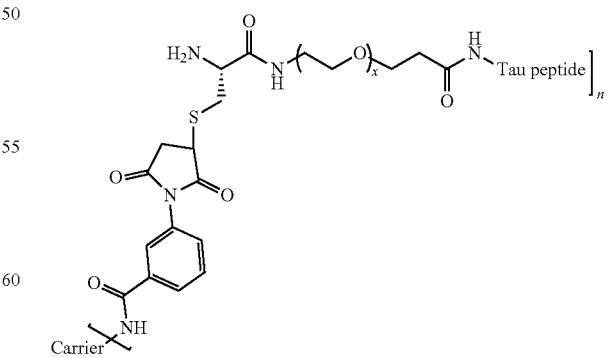

wherein
x is an integer of 0 to 10; and
n is an integer of 2 to 15, preferably 3-11.

According to particular embodiments, x is an integer of 1 to 10, 2 to 9, 2 to 8, 2 to 7, 2 to 6, 2 to 5, 2 to 4, or 2 to 3. According to particular embodiments, x is 3.

According to particular embodiments, n is 2 to 15, 3 to 11, 3 to 9, 3 to 8, or 3 to 7.

According to particular embodiments, the conjugate comprises one or more tau peptides. According to particular embodiments, the tau peptides of the conjugate can be the same or different.

According to particular embodiments, in view of the present disclosure, any suitable tau peptides can be used in the invention. According to particular embodiments, one or more of the tau peptides comprise the amino acid sequence of one of SEQ ID NOs: 1-12, or an amino acid sequence that is at least 75%, 80%, 85%, 90% or 95% identical to the amino acid sequence of one of SEQ ID NOs: 1-12, wherein none, one or more of the amino acid residues are phosphorylated.

According to particular embodiments, one or more of the tau peptides is a tau phosphopeptide. According to particular embodiments, the one or more tau phosphopeptides comprise the amino acid sequence of one of SEQ ID NOs: 1-3 or 5-12, or an amino acid sequence that is at least 75%, 80%, 85%, 90% or 95% identical to the amino acid sequence of one of SEQ ID NOs: 1-3 or 5-12, wherein one or more of the indicated amino acid residues are phosphorylated.

According to particular embodiments, the tau phosphopeptide consists of the amino acid sequence of one of SEQ ID NOs: 1-3.

term "linker" refers to a chemical moiety that joins a immunogenic carrier to a tau peptide. Any suitable linker known to those skilled in the art in view of the present disclosure can be used in the invention. The linkers can be, for example, a single covalent bond, a substituted or unsubstituted alkyl, a substituted or unsubstituted heteroalkyl moiety, a polyethylene glycol (PEG) linker, a peptide linker, a sugar-based linker, or a cleavable linker, such as a disulfide linkage or a protease cleavage site, or an amino acid, or a combination thereof. Examples of the linker can comprises one or more of polyethylene glycol (PEG), succinimidyl 3-(bromoacetamido)propionate (SBAP), m-maleimidobenzoyl-N-hydroxysuccinimide ester (MBS), or one or more amino acids such as Cys, Lys or sometimes Ser or Thr, or a combination thereof.

According to particular embodiments, the linker comprises $(C_2H_4O)x$-cysteine-acetamidopropionamide or m-maleimidobenzoyl-N-hydroxysuccinimide ester-cysteine-$(C_2H_4O)x$, wherein x is an integer of 0 to 10, such as 0, 1, 2, 3, 4, 5, 6, 7, 8, 9, or 10.

According to particular embodiments, the carrier is covalently linked to the N-terminus of the tau peptide, via a linker.

According to other particular embodiments, the carrier is covalently linked to the C-terminus of the tau peptide, via a linker.

According to particular embodiments, the conjugate has the structure of:

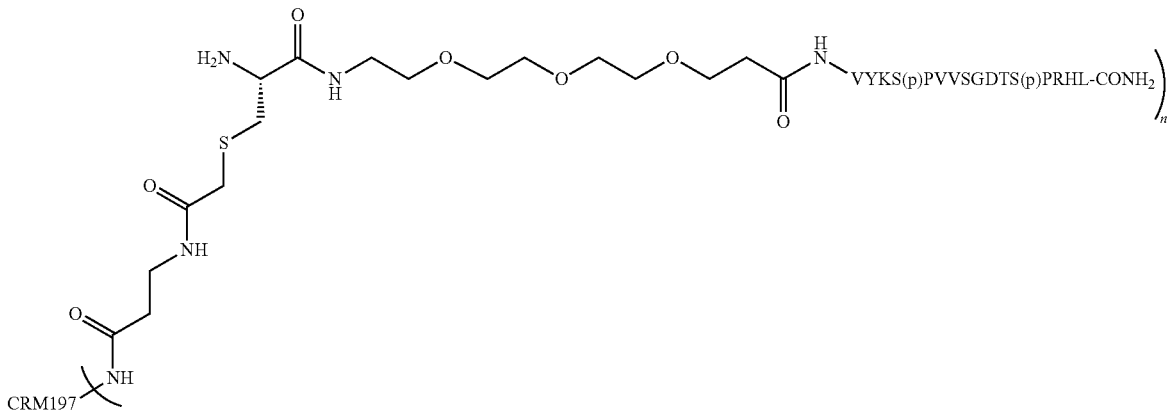

As used herein, the term "immunogenic carrier" refers to an immunogenic substance that can be coupled to a tau peptide. An immunogenic moiety coupled to a tau peptide can induce an immune response and elicit the production of antibodies that can specifically bind the tau peptide. Immunogenic moieties are operative moieties that include proteins, polypeptides, glycoproteins, complex polysaccharides, particles, nucleic acids, polynucleotides, and the like that are recognized as foreign and thereby elicit an immunologic response from the host. Any suitable immunogenic carrier known to those skilled in the art in view of the present disclosure can be used in the invention. According to particular embodiments, the immunogenic carrier is keyhole limpet hemocyanin (KLH), tetanus toxoid, CRM197 (a non-toxic form of diphtheria toxin), an outer membrane protein mixture from $N$ meningitidis (OMP), or a derivative thereof. According to particular embodiments, the immunogenic carrier is KLH or CRM197.

According to particular embodiments, the tau peptide is conjugated to the carrier via a linker. As used herein, the wherein n is an integer of 2 to 15, preferably 3-11, more preferably 3-7.

Conjugates of the invention can be made by methods known in the art in view of the present disclosure. For example, the above conjugate can be formed by reacting succinimidyl-3-(bromoacetamido)propionate (SBAP):

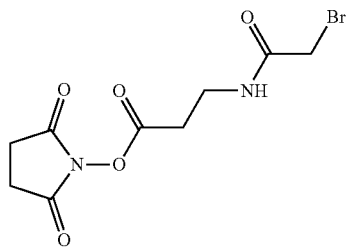

with an amino group of CRM197 to form an amide linkage. This CRM197 precursor can be subsequently reacted with the tau peptide (e.g., the phosphorylated tau peptide of SEQ ID NO: 2) conjugated at its N-terminus or at its C-terminus to a PEG-cysteine linker with a free nucleophilic thiol group to form the tau phosphopeptide conjugate.

An exemplary conjugate according to an embodiment of the present application is illustrated in FIG. 1. More specifically, multiple tau phosphopeptides (pTau Peptide T3.76) is covalently linked to a carrier protein CRM197.

Pharmaceutical Compositions

In one general aspect, the invention relates to pharmaceutical compositions comprising a therapeutically effective amount of liposome or conjugate of the invention, together with a pharmaceutically acceptable excipient and/or carrier. Pharmaceutically acceptable excipients and/or carriers are well known in the art (see Remington's Pharmaceutical Science (15th ed.), Mack Publishing Company, Easton, Pa., 1980). The preferred formulation of the pharmaceutical composition depends on the intended mode of administration and therapeutic application. The compositions can include pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers, and the like. It will be understood that the characteristics of the carrier, excipient or diluent will depend on the route of administration for a particular application.

The pharmaceutical composition can contain a mixture of the same immunogenic tau peptide. Alternatively, the pharmaceutical composition can contain a mixture of different immunogenic tau peptides of the present invention.

Another problem associated with vaccines against neuronal diseases is that exceptionally high antibody titers are likely to be necessary to assure efficacy. This is because the target antigen for the vaccine is located in the brain. The brain is separated from the circulation by a specialized cellular structure called the blood-brain barrier (BBB). The BBB restricts passage of substances from the circulation into the brain. This prevents the entry of toxins, microbes, etc. into the central nervous system. The BBB also has the potentially less desirable effect of preventing the efficient entry of immune mediators (such as antibodies) into the interstitial and cerebrospinal fluid that surrounds the brain.

Approximately 0.1% of antibodies that are present in the systemic circulation cross the BBB and enter the brain. This means that systemic titers induced by a vaccine targeting a CNS antigen must be at least 1000 times greater than the minimal effective titer to be efficacious in the brain.

According to particular embodiments, the pharmaceutical compositions of the present invention therefore further comprise one or more suitable adjuvants. Thus, the tau peptides of the present invention, present in the liposome or the conjugate, can be administered in combination with a suitable adjuvant to achieve the desired immune response in the subject. Suitable adjuvants can be administered before, after, or concurrent with administration of liposome or conjugate of the present invention. Preferred adjuvants augment the intrinsic response to an immunogen without causing conformational changes in the immunogen that affect the qualitative form of the response. Examples of adjuvants are the aluminum salts (alum), such as aluminum hydroxide, aluminum phosphate, and aluminum sulfate. Such adjuvants can be used with or without other specific immunostimulating agents, such as MPLA Class (3 De-O-acylated monophosphoryl lipid A (MPL™), monophosphoryl hexa-acyl Lipid A 3-deacyl synthetic (3D-(6-acyl) PHAD®), PHAD™, PHAD®-504, 3D-PHAD®) lipid A), polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include MF59 (see WO 90/14837), containing 5% Squalene, 0.5% Tween® 80, and 0.5% Span® 85 (optionally containing various amounts of MTP-PE) formulated into submicron particles using a microfluidizer; SAF, containing 10% Squalene, 0.4% Tween® 80, 5% pluronic-blocked polymer L121, and thr-MDP, either microfluidized into a submicron emulsion or vortexed to generate a larger particle size emulsion; and the Ribi™ adjuvant system (RAS) (Ribi ImmunoChem, Hamilton, Mont.) 0.2% Tween® 80, and one or more bacterial cell wall components selected from the group consisting of monophosphoryl lipid A (MPL™), trehalose dimycolate (TDM), and cell wall skeleton (CWS), preferably MPL™+CWS (Detox™). Other adjuvants include Complete Freund's Adjuvant (CFA), and cytokines, such as interleukins (IL-1, IL-2, and IL-12), macrophage colony stimulating factor (M-CSF), and tumor necrosis factor (TNF).

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Pharmaceutical compositions of the present invention can be formulated according to methods well known in the art. The optimal ratios of each component in the compositions can be determined by techniques well known to those skilled in the art in view of the present disclosure.

Methods of Use

Another general aspect of the invention relates to methods for inducing an immune response against tau protein in a subject suffering from a neurodegenerative disease, disorder, or condition, comprising administering to the subject a pharmaceutical composition according to an embodiment of the invention. According to particular aspects, the immune response is induced against phosphorylated tau protein, preferably ePHF.

Another general aspect of the invention relates to methods for treating or preventing a neurodegenerative disease, disorder, or condition, comprising administering to the subject a pharmaceutical composition according to an embodiment of the invention.

As used herein, the terms "induce" and "stimulate" and variations thereof refer to any measurable increase in cellular activity. Induction of an immune response can include, for example, activation, proliferation, or maturation of a population of immune cells, increasing the production of a cytokine, and/or another indicator of increased immune function. In certain embodiments, induction of an immune response can include increasing the proliferation of B cells, producing antigen-specific antibodies, increasing the proliferation of antigen-specific T cells, improving dendritic cell antigen presentation and/or an increasing expression of certain cytokines, chemokines and co-stimulatory markers.

The ability to induce or stimulate an anti-tau immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed. J Wiley & Sons Inc, National Institute of Health). Measurement of cellular immunity can be performed by methods readily known in the art, e.g., by measurement of cytokine profiles secreted by activated effector cells including those derived from $CD4^+$ and $CD8^+$ T-cells (e.g. quantification of IL-4 or IFN gamma-producing cells by ELISPOT), by determination of the activation status of immune effector cells (e.g. T-cell proliferation assays by a classical [3H] thymidine uptake), by assaying for antigen-specific T lymphocytes in a sensitized subject (e.g. peptide-specific lysis in a cytotoxicity assay, etc.).

The ability to stimulate a cellular and/or a humoral response can be determined by testing a biological sample (e.g., blood, plasma, serum, PBMCs, urine, saliva, feces, CSF or lymph fluid) from the subject for the presence of antibodies directed to the immunogenic tau peptide(s) administered in the pharmaceutical composition (see for example Harlow, 1989, Antibodies, Cold Spring Harbor Press). For example, titers of antibodies produced in response to administration of a composition providing an immunogen can be measured by enzyme-linked immunosorbent assay (ELISA), dot blots, SDS-PAGE gels, ELISPOT or Antibody-Dependent Cellular Phagocytosis (ADCP) Assay.

As used herein, the term "subject" refers to an animal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee or human). According to particular embodiments, the subject is a human.

As used herein, the term "therapeutically effective amount" refers to an amount of an active ingredient or component that elicits the desired biological or medicinal response in a subject. A therapeutically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

As used herein, the terms "treat", "treating", and "treatment" are all intended to refer to an amelioration or reversal of at least one measurable physical parameter related to a neurodegenerative disease, disorder, or condition, which is not necessarily discernible in the subject, but can be discernible in the subject. The terms "treat", "treating", and "treatment" can also refer to causing regression, preventing the progression, or at least slowing down the progression of the disease, disorder, or condition. In a particular embodiment, "treat", "treating", and "treatment" refer to an alleviation, prevention of the development or onset, or reduction in the duration of one or more symptoms associated with the neurodegenerative disease, disorder, or condition. In a particular embodiment, "treat", "treating", and "treatment" refer to prevention of the recurrence of the disease, disorder, or condition. In a particular embodiment, "treat", "treating", and "treatment" refer to an increase in the survival of a subject having the disease, disorder, or condition. In a particular embodiment, "treat", "treating", and "treatment" refer to elimination of the disease, disorder, or condition in the subject.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (x) inhibit or reduce the disease, disorder or condition to be treated, or a symptom associated therewith in a subject; and/or (xi) enhance or improve the prophylactic or therapeutic effect(s) of another therapy.

As used herein a "neurodegenerative disease, disorder, or condition" includes any neurodegenerative disease, disorder, or condition known to those skilled in the art in view of the present disclosure. Examples of neurodegenerative diseases, disorders, or conditions include neurodegenerative diseases or disorders caused by or associated with the formation of neurofibrillary lesions, such as tau-associated diseases, disorders or conditions, referred to as tauopathies. According to particular embodiments, the neurodegenerative disease, disorder, or condition includes any of the diseases or disorders which show co-existence of tau and amyloid pathologies including, but not is limited to, Alzheimer's Disease, Parkinson's Disease, Creutzfeldt-Jacob disease, Dementia pugilistica, Down's Syndrome, Gerstmann-Sträussler-Scheinker disease, inclusion body myositis, prion protein cerebral amyloid angiopathy, traumatic brain injury, amyotrophic lateral sclerosis, parkinsonism-dementia complex of Guam, Non-Guamanian motor neuron disease with neurofibrillary tangles, argyrophilic grain dementia, corticobasal degeneration, Dementia Lewy Amyotrophic Lateral sclerosis, diffuse neurofibrillary tangles with calcification, frontotemporal dementia, preferably frontotemporal dementia with parkinsonism linked to chromosome 17 (FTDP-17), frontotemporal lobar dementia, Hallevorden-Spatz disease, multiple system atrophy, Niemann-Pick disease type C, Pick's disease, progressive subcortical gliosis, progressive supranuclear palsy, Subacute sclerosing panencephalitis, Tangle only dementia, Postencephalitic Parkinsonism, Myotonic dystrophy, chronic traumatic encephalopathy (CTE), Primary age-related tauopathy (PART), or Lewy body dementia (LBD). According to particular embodiments, the neurodegenerative disease, disorder, or condition is Alzheimer's disease or another tauopathy.

The present invention also provides a method for promoting clearance of tau aggregates from the brain of a subject, said method comprising administering to the subject a pharmaceutical composition according to an embodiment of the invention, under conditions effective to promote clearance of the tau aggregates from the brain of the subject. According to particular embodiments, the tau aggregates are neurofibrillary tangles or their pathological tau precursors.

The present invention also provides a method for slowing progression of a tau-pathology related behavioral phenotype in a subject, said method comprising administering to the subject a pharmaceutical composition according to an embodiment of the invention, under conditions effective to slow the progression of the tau-pathology related behavioral phenotype in the subject.

In a preferred embodiment of the present invention, administration of a tau peptide, via administration of a pharmaceutical composition according to an embodiment of the invention, induces an active immune response in the subject to the tau peptide and to the pathological form of tau, thereby facilitating the clearance of related tau aggregates, slowing the progression of tau-pathology related behavior and/or treating the underlying tauopathy. In accordance with this aspect of the present invention, an immune response involves the development of a beneficial humoral (antibody mediated) response directed against the tau peptide and a cellular (mediated by antigen-specific T cells or their secretion products) response directed against the T-cell epitope or the immunogenic carrier.

As used herein, a tau-pathology related behavioral phenotype includes, without limitation, cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

In carrying out the methods of the present invention, it is preferable to select a subject having or at risk of having Alzheimer's disease or other tauopathy, a subject having tau aggregates in the brain, or a subject exhibiting a tangle related behavioral phenotype prior to administering the immunogenic peptides or antibodies of the present invention. Subjects amenable to treatment include individuals at risk of disease but not showing symptoms, as well as patients presently showing symptoms. In the case of Alzheimer's disease, virtually anyone is at risk of suffering from Alzheimer's disease. Therefore, the present methods can be administered prophylactically to the general population without the need for any assessment of the risk of the subject patient. The present methods are especially useful for individuals who have a known genetic risk of Alzheimer's disease. Such individuals include those having relatives who have experienced the disease, and those whose risk is determined by analysis of genetic or biochemical markers.

In asymptomatic patients, treatment can begin at any age (e.g., 10, 20, 30 years of age). Usually, however, it is not necessary to begin treatment until a patient reaches 40, 50, 60, or 70 years of age. Treatment typically entails multiple dosages over a period of time. Treatment can be monitored by assaying antibody, or activated T-cell or B-cell responses to the therapeutic agent over time. If the response decreases, a booster dosage is indicated.

In prophylactic applications, pharmaceutical compositions containing the tau peptides are administered to a patient susceptible to, or otherwise at risk of, Alzheimer's disease or other tauopathy in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, pharmaceutical compositions containing a tau peptide are administered to a patient suspected of, or already suffering from, such a disease in an amount sufficient to cure, or at least partially arrest, the symptoms of the disease (biochemical, histologic and/or behavioral), including its complications and intermediate pathological phenotypes in development of the disease.

Effective doses of a pharmaceutical composition of the invention, for the prevention and/or treatment of the neurodegenerative disease, disorder, or condition vary depending upon many different factors, including mode of administration, target site, physiological state of the patient, other medications administered, and whether treatment is prophylactic or therapeutic. The amount of peptides depends on whether adjuvant is also administered, with higher dosages being required in the absence of adjuvant. The timing of injections can vary significantly from once a day, to once a year, to once a decade. A typical regimen consists of an immunization followed by booster injections at time intervals, such as 6 week intervals. Another regimen consists of an immunization followed by booster injections 1, 2, 6, 9 and 12 months later. Another regimen entails an injection every two months for life. Alternatively, booster injections can be on an irregular basis as indicated by monitoring of immune response.

It is readily appreciated by those skilled in the art that the regimen for the priming and boosting administrations can be adjusted based on the measured immune responses after the administrations. For example, the boosting compositions are generally administered weeks or months after administration of the priming composition, for example, about 2-3 weeks or 4 weeks, or 8 weeks, or 16 weeks, or 20 weeks, or 24 weeks, or 26 weeks, or 28 weeks, or 30 weeks or 32 weeks or 36 weeks or one to two years after administration of the priming composition.

The peptides can be administered by parenteral, topical, intravenous, oral, subcutaneous, intra-arterial, intracranial, intraperitoneal, intradermal, intranasal, or intramuscular means for prophylactic and/or therapeutic treatment. The most typical route of administration of an immunogenic agent is subcutaneous or intramuscular injection. This latter type of injection is most typically performed in the arm or leg muscles.

According to particular aspects, one or more boosting immunizations can be administered. The antigens in the respective priming and boosting compositions, however many boosting compositions are employed, need not be identical, but should share antigenic determinants or be substantially similar to each other.

The composition can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration.

According to particular embodiments, the kit comprises at least one of a pharmaceutical composition comprising a liposome according to an embodiment of the invention and a pharmaceutical composition comprising a conjugate according to an embodiment of the invention.

EMBODIMENTS

The invention provides also the following non-limiting embodiments.

Embodiment 1 is a liposome, comprising:
a. a tau peptide; and
b. a helper T cell epitope;
wherein the tau peptide is presented on the surface of the liposome.

Embodiment 2 is the liposome of Embodiment 1, wherein the tau peptide is a tau phosphopeptide.

Embodiment 3 is the liposome of Embodiment 1 or 2, further comprising a toll-like receptor ligand.

Embodiment 4 is the liposome of Embodiment 3, wherein the toll-like receptor ligand comprises at least one of a toll-like receptor 4 ligand and toll-like receptor 9 ligand.

Embodiment 5 is the liposome of Embodiment 3 or 4, wherein the toll-like receptor ligand is a toll-like receptor 4 ligand.

Embodiment 6 is the liposome of Embodiment 5, wherein the toll-like receptor 4 ligand comprises monophosphoryl lipid A (MPLA).

Embodiment 7 is the liposome of Embodiment 3 or 4, wherein the toll-like receptor ligand is a toll-like receptor 9 ligand.

Embodiment 8 is the liposome of Embodiment 7, wherein the toll-like receptor 9 ligand comprises a lipidated CpG oligonucleotide.

Embodiment 9 is the liposome of Embodiment 1, comprising:
a. a tau peptide;
b. a helper T cell epitope; and
c. at least one of
i. a toll-like receptor 9 ligand, and
ii. a toll-like receptor 4 ligand.

Embodiment 10 is the liposome of Embodiment 9, wherein the tau peptide is a tau phosphopeptide.

Embodiment 11 is the liposome of Embodiment 9 or 10, wherein the toll-like receptor 9 ligand is a lipidated CpG oligonucleotide.

Embodiment 12 is the liposome of any of Embodiments 9 to 11, wherein the liposome comprises the toll-like receptor 4 ligand and toll-like receptor 9 ligand.

Embodiment 13 is the liposome of Embodiment 12, wherein the toll-like receptor 4 ligand comprises monophosphoryl lipid A (MPLA).

Embodiment 14 is a liposome, comprising:
a. a tau phosphopeptide;
b. a helper T-cell epitope;
c. a lipidated CpG oligonucleotide; and
d. an adjuvant containing a toll-like receptor 4 ligand;
wherein the tau phosphopeptide is presented on the surface of the liposome.

Embodiment 15 is the liposome of Embodiment 14, wherein the toll-like receptor 4 ligand comprises monophosphoryl lipid A (MPLA).

Embodiment 16 is the liposome of any of Embodiments 1 to 15, wherein the helper T cell epitope is encapsulated in the liposome.

Embodiment 16a is the liposome of any of Embodiments 1 to 15, wherein the helper T cell epitope is incorporated in the membrane of the liposome.

Embodiment 16b is the liposome of any of Embodiments 1 to 15, wherein the helper T cell epitope is presented on the surface of the liposome.

Embodiment 17 is a liposome composition, comprising:
a. a tau phosphopeptide;
b. a helper T cell epitope;
c. a lipidated CpG oligonucleotide; and
d. a monophosphoryl lipid A (MPLA);
wherein the tau phosphopeptide is presented on the surface of the liposome, and the T-cell epitope is encapsulated in the liposome.

Embodiment 17a is the liposome of Embodiment 17, wherein the MPLA is 3-O-desacyl-4'-monophosphoryl lipid A, preferably MPL™.

Embodiment 17b is the liposome of Embodiment 17, wherein the MPLA is monophosphoryl hexa-acyl lipid A, 3-deacyl, preferably 3D-(6-acyl) PHAD®.

Embodiment 17c is the liposome of Embodiment 17, wherein the MPLA is monophosphoryl 3-deacyl lipid A, preferably 3D-PHAD®.

Embodiment 18 is the liposome of any of Embodiments 1 to 17c, further comprising one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

Embodiment 19 is the liposome of any of Embodiments 1 to 18, wherein the tau peptide has an amino acid sequence selected from the group consisting of SEQ ID NO:1 to SEQ ID NO:12, or at least 85%, 90% or 95% identical to an amino acid sequence selected from the group consisting of SEQ ID NO:1 to SEQ ID NO:12.

Embodiment 19-1 is the liposome of Embodiment 19, wherein the tau peptide is a phosphopeptide comprising an amino acid sequence selected from the group consisting of SEQ ID NOs: 1-3 and 5-12.

Embodiment 19-2 is the liposome of Embodiment 19-1, wherein the tau phosphopeptide comprises the amino acid sequence of SEQ ID NO:1.

Embodiment 19-3 is the liposome of Embodiment 19-1, wherein the tau phosphopeptide comprises the amino acid sequence of SEQ ID NO:2.

Embodiment 19-4 is the liposome of Embodiment 19-1, wherein the tau phosphopeptide comprises the amino acid sequence of SEQ ID NO:3.

Embodiment 19a is the liposome of any one of Embodiments 19, 19-1, 19-2, 19-3 and 19-4, wherein the amino acid sequence further comprises one or more modifications to allow the tau peptide to be presented on the surface of the liposome.

Embodiment 19b is the liposome of Embodiment 19a, wherein the one or more modifications comprise at least one of palmitoylation and dodecyl modification.

Embodiment 19c is the liposome of Embodiment 19a or 19b, wherein the tau peptide is modified at its N-terminus by the one or more modifications.

Embodiment 19d is the liposome of any of Embodiments 19a to 19c, wherein the tau peptide is modified at its C-terminus by the one or more modifications.

Embodiment 19e is the liposome of Embodiment 19d, wherein the tau peptide is palmitoylated at both of its N-terminus and C-terminus.

Embodiment 19f is the liposome of any of Embodiments 19a-19e, wherein the tau peptide further comprises one or more additional amino acids to facilitate the one or more modifications.

Embodiment 19g is the liposome of Embodiment 19f, wherein the one or more additional amino acids are selected from the group consisting of Lys, Cys, Ser and Thr.

Embodiment 19h is the liposome of any of Embodiments 19 to 19g, wherein the tau peptide is amidated at its C-terminus.

Embodiment 19i is the liposome of any of Embodiments 19 to 19h, wherein the tau peptide consists of an amino acid sequence selected from the group consisting of SEQ ID NO:27 to SEQ ID NO:38.

Embodiment 19j is the liposome of any of Embodiments 19-19i, wherein the tau peptide consists of the amino acid sequence of SEQ ID NO:27.

Embodiment 19k is the liposome of any of Embodiments 19-19i, wherein the tau peptide consists of the amino acid sequence of SEQ ID NO:28.

Embodiment 19l is the liposome of any of Embodiments 19-19i, wherein the tau peptide consists of the amino acid sequence of SEQ ID NO:29.

Embodiment 20 is the liposome of any of Embodiments 1 to 19l, wherein the helper T cell epitope comprises at least one amino acid sequence selected from the group consisting of: SEQ ID NO:23 to SEQ ID NO:26.

Embodiment 20a is the liposome of Embodiment 20, wherein helper T cell epitope comprises at least two amino acid sequences selected from the group consisting of: SEQ ID NO:23 to SEQ ID NO:26.

Embodiment 20b is the liposome of Embodiment 20, wherein helper T cell epitope comprises at least three amino acid sequences selected from the group consisting of: SEQ ID NO:23 to SEQ ID NO:26.

Embodiment 20c is the liposome of Embodiment 20, wherein helper T cell epitope comprises the four amino acid sequences of: SEQ ID NO:23 to SEQ ID NO:26.

Embodiment 20d is the liposome of any of Embodiments 20a to 20c, wherein the two or more amino acid sequences selected from the group consisting of SEQ ID NO:23 to SEQ ID NO:26 are covalently linked by a linker.

Embodiment 20e is the liposome of Embodiment 20d, wherein the linker comprises one or more amino acids selected from the group consisting of Val (V), Ala (A), Arg (R), Gly (G), Ser (S), Lys (K).

Embodiment 20f is the liposome of Embodiment 20e, wherein the linker comprises an amino acid sequence selected from the group consisting of VVR, GS, RR and RK.

Embodiment 20g is the liposome of any of Embodiments 20 to 20f, wherein the helper T cell epitope is amidated at its C-terminus.

Embodiment 20h is the liposome of any of Embodiments 20 to 20g, wherein the helper T cell epitope is modified for insertion into the membrane of the liposome, presentation on the surface of the liposome or encapsulation in the liposome, depending on the intended location of the helper T cell epitope.

Embodiment 20i is the liposome of any of Embodiments 20 to 20h, wherein the helper T cell epitope consisting of an amino acid sequence selected from the group consisting of SEQ ID NO:13 to SEQ ID NO:17.

Embodiment 20j is the liposome of any of Embodiments 1 to 20i, wherein liposome comprises the tau peptide and the helper T cell epitope at a weight ratio of 6:1.

Embodiment 20k is the liposome of any of Embodiments 1 to 20i, wherein liposome comprises the tau peptide and the helper T cell epitope at a weight ratio of 5:1.

Embodiment 20l is the liposome of any of Embodiments 1 to 20i, wherein liposome comprises the tau peptide and the helper T cell epitope at a weight ratio of 4:1.

Embodiment 20m is the liposome of any of Embodiments 1 to 20i, wherein liposome comprises the tau peptide and the helper T cell epitope at a weight ratio of 3:1.

Embodiment 20n is the liposome of any of Embodiments 1 to 20i, wherein liposome comprises the tau peptide and the helper T cell epitope at a weight ratio of 2:1.

Embodiment 20o is the liposome of any of Embodiments 1 to 20i, wherein liposome comprises the tau peptide and the helper T cell epitope at a weight ratio of 1:1.

Embodiment 21 is the liposome of any of Embodiments 1 to 20o, wherein the lipidated CpG oligonucleotide comprises the nucleotide sequence selected from the group consisting of SEQ ID NO:18 to SEQ ID NO:22.

Embodiment 21a is the liposome of Embodiment 21, wherein the CpG oligonucleotide has one or more phosphorothioate internucleotide linkages.

Embodiment 21b is the liposome of Embodiment 21a, wherein the CpG oligonucleotide has all phosphorothioate internucleotide linkages.

Embodiment 21c is the liposome of any of Embodiments 21 to 21b, wherein lipidated CpG oligonucleotide comprises the CpG oligonucleotide covalently linked to at least one lipophilic group via a linker.

Embodiment 21d is the liposome of Embodiment 21c, wherein the linker comprises (C2H4O)n, wherein n is an integer of 0 to 10.

Embodiment 21e is the liposome of Embodiment 21c, wherein the linker comprises an alkyl spacer having 3 to 12 carbons.

Embodiment 21f is the liposome of any of Embodiments 21 to 21e, wherein the at least one lipophilic group is cholesterol.

Embodiment 21g is the liposome of any of Embodiments 21 to 21f, wherein the lipidated CpG oligonucleotide comprises the nucleotide sequence of SEQ ID NO:18 or SEQ ID NO:19 covalently linked to a cholesterol molecule via a linker comprising (C2H4O)n, wherein n is an integer of 3 to 5.

Embodiment 22 is a liposome, comprising:
a. a tau peptide having an amino acid sequence selected from the group consisting of SEQ ID NO:27 to SEQ ID NO:38;
b. a helper T cell epitope having an amino acid sequence selected from the group consisting of SEQ ID NO:39 to SEQ ID NO:44, preferably, the helper T cell epitope consisting of an amino acid sequence selected from the group consisting of SEQ ID NO:13 to SEQ ID NO:17;
c. a lipidated CpG oligonucleotide having a nucleotide sequence selected from the group consisting of SEQ ID NO:18 to SEQ ID NO:22, wherein the CpG oligonucleotide comprises one or more phosphorothioate internucleotide linkages, and the CpG oligonucleotide is covalently linked to at least one cholesterol via a linker; and
d. monophosphoryl lipid A (MPLA).

Embodiment 22a is a liposome of Embodiment 22, comprising:
a. a tau phosphopeptide consisting of the amino acid sequence of SEQ ID NO:27, SEQ ID NO:28 or SEQ ID NO:29;
b. a helper T cell epitope consisting of the amino acid sequence of SEQ ID NO:13
c. a lipidated CpG oligonucleotide consisting of the nucleotide sequence of SEQ ID NO: 18 or SEQ ID NO:19 covalently linked to a cholesterol via a linker comprising $(C_2H_4O)n$, wherein n is an integer of 3 to 7; and
d. monophosphoryl lipid A (MPLA).

Embodiment 22b is the liposome of Embodiment 22 or 22a, wherein the MPLA is 3-O-desacyl-4'-monophosphoryl lipid A, preferably MPL™.

Embodiment 22c is the liposome of Embodiment 22 or 22a, wherein the MPLA is preferably 3D-(6-acyl) PHAD®.

Embodiment 22d is the liposome of Embodiment 22 or 22a, wherein the MPLA is, preferably 3D-PHAD®.

Embodiment 23 is the liposome of any one of Embodiments 22 to 22d, wherein the helper T cell epitope is encapsulated in the liposome.

Embodiment 24 is a pharmaceutical composition comprising the liposome of any of Embodiments 1 to 23 and a pharmaceutically acceptable carrier.

Embodiment 25 is a conjugate comprising a tau phosphopeptide and an immunogenic carrier conjugated thereto via a linker, having the following structure:

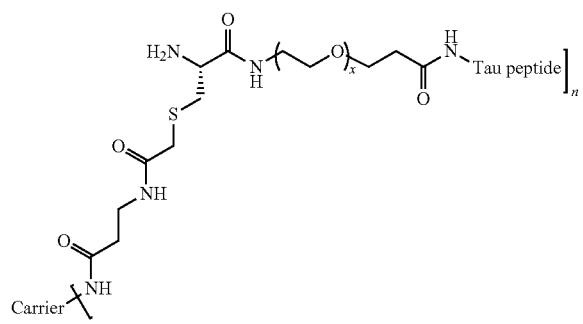

wherein x is an integer of 0 to 10; and
n is an integer of 2 to 15.

Embodiment 25a is a conjugate comprising a tau phosphopeptide and an immunogenic carrier conjugated thereto via a linker, having the structure of formula (II):

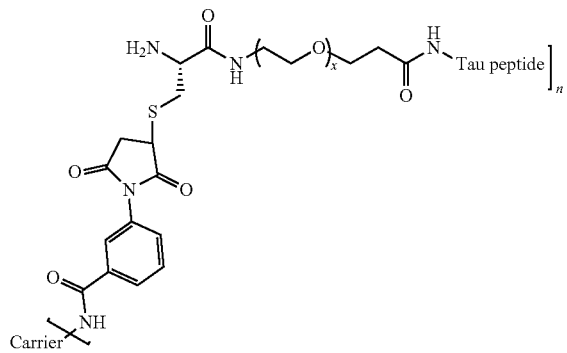

wherein
x is an integer of 0 to 10; and
n is an integer of 2 to 15.

Embodiment 26 is the conjugate of Embodiment 25 or 25a, wherein x is an integer of 2 to 6.

Embodiment 27 is the conjugate of Embodiment 25 or 25a, wherein x is 3.

Embodiment 28 is the conjugate of any of Embodiments 25 to 25a, wherein n is 3 to 7.

Embodiment 29 is the conjugate of any of Embodiments 25 to 28, wherein the carrier is an immunogenic carrier selected from the group consisting of keyhole limpet hemocyanin (KLH), tetanus toxoid, CRM197, and an outer membrane protein mixture from *N. meningitidis* (OMP), or a derivative thereof.

Embodiment 30 is the conjugate of any of Embodiments 25 to 29, wherein the tau phosphopeptide consists of the amino acid sequence selected from the group consisting of SEQ ID NO:1 to SEQ ID NO:12.

Embodiment 30a is the conjugate of Embodiment 30, wherein the tau phosphopeptide consists of the amino acid sequence of SEQ ID NO:1, SEQ ID NO:2 or SEQ ID NO:3.

Embodiment 31 is the conjugate of any of Embodiments 25 to 30, wherein the carrier is CRM197.

Embodiment 32 is the conjugate of Embodiment 25, having the structure of:

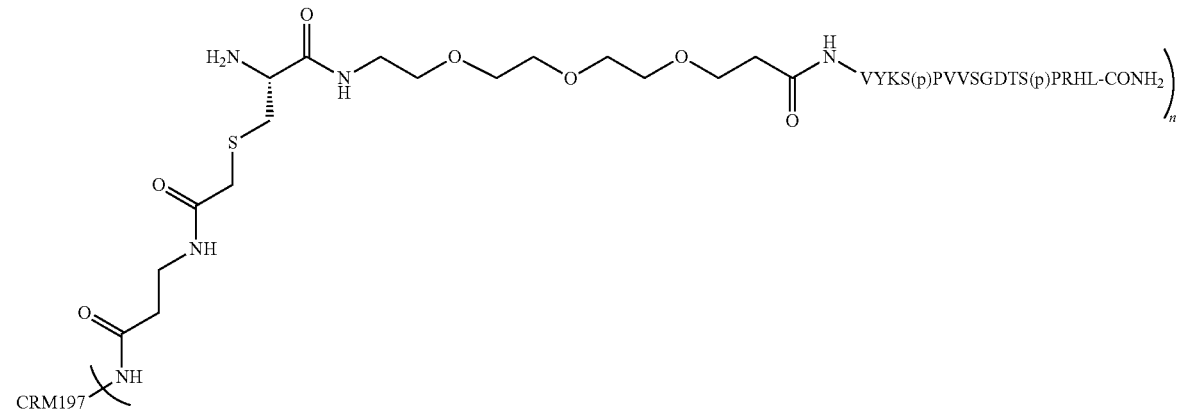

wherein n is 3-7.

Embodiment 32a is the conjugate of Embodiment 25, wherein the KLH-[m-maleimidobenzoyl-N-hydroxysuccinimide ester-cysteine-(C₂H₄O)x-Tau peptide]$_n$

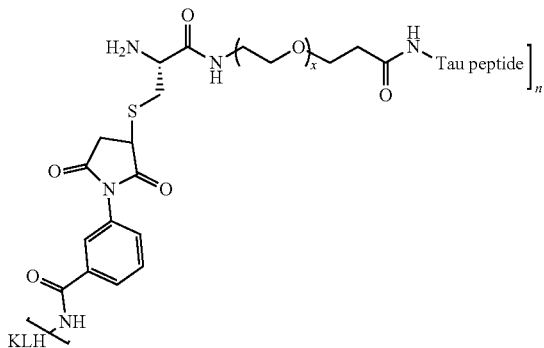

wherein
the Tau peptide consisting of SEQ ID NO:1 or SEQ ID NO:3;
x is an integer of 0 to 10; and
n is an integer of 2 to 15.

Embodiment 33 is a pharmaceutical composition comprising the conjugate of any of Embodiments 25 to 32a and a pharmaceutically acceptable carrier.

Embodiment 33a is the pharmaceutical composition of claim 33, further comprising an adjuvant.

Embodiment 33b is the pharmaceutical composition of claim 33a, wherein the adjuvant comprises at least one of a TLR-4 ligand and a TLR-9 ligand.

Embodiment 34 is a method for inducing an immune response in a subject suffering from a neurodegenerative disorder, comprising administering to the subject at least one of the pharmaceutical compositions of Embodiments 24 and 33 to 33b.

Embodiment 35 is the method of Embodiment 34, comprising administering to the subject at least one of the pharmaceutical compositions of Embodiments 24 and 33 to 33b for priming immunization, and administering to the subject at least one of the pharmaceutical compositions of Embodiments 24 and 33 to 33b for boosting immunization.

Embodiment 36 is a method for treating or preventing a neurodegenerative disease or disorder in a subject in need thereof, comprising administering to the subject at least one of the pharmaceutical compositions of Embodiment 24 or 33.

Embodiment 37 is the method of Embodiment 36, comprising administering to the subject at least one of the pharmaceutical compositions of Embodiments 24 and 33 to 33b for priming immunization, and administering to the subject at least one of the pharmaceutical compositions of Embodiments 24 and 33 to 33b for boosting immunization.

Embodiment 38 is the method of any of Embodiments 34 to 37, wherein the neurodegenerative disease or disorder is caused by or associated with the formation of neurofibrillary lesions.

Embodiment 39 is the method of any of Embodiments 34 to 38, wherein the neurodegenerative disease or disorder is Alzheimer's Disease, Parkinson's Disease, Creutzfeldt-Jacob disease, Dementia pugilistica, Down's Syndrome, Gerstmann-Sträussler-Scheinker disease, inclusion body myositis, prion protein cerebral amyloid angiopathy, traumatic brain injury, amyotrophic lateral sclerosis, parkinsonism-dementia complex of Guam, Non-Guamanian motor neuron disease with neurofibrillary tangles, argyrophilic grain dementia, corticobasal degeneration, Dementia Lewy Amyotrophic Lateral sclerosis, diffuse neurofibrillary tangles with calcification, frontotemporal dementia, preferably frontotemporal dementia with parkinsonism linked to chromosome 17 (FTDP-17), frontotemporal lobar dementia, Hallevorden-Spatz disease, multiple system atrophy, Niemann-Pick disease type C, Pick's disease, progressive subcortical gliosis, progressive supranuclear palsy, Subacute sclerosing panencephalitis, Tangle only dementia, Postencephalitic Parkinsonism, Myotonic dystrophy, chronic traumatic encephalopathy (CTE), Primary age-related tauopathy (PART), or Lewy body dementia (LBD).

Embodiment 40 is the method of any of Embodiments 34 to 39, wherein the neurodegenerative disease or disorder is Alzheimer's disease, Parkinson's Disease, Down's Syndrome, progressive supranuclear palsy (PSP), frontotemporal dementia and parkinsonism linked to chromosome 17 (FTDP-17), Pick's disease, Corticobasal Degeneration, Dementia Lewy Amyotrophic Lateral sclerosis, Myotonic disphasy, chronic traumatic encephalopathy (CTE), Cerebral angiopahty, Primary age-related tauopathy (PART), or Lewy body dementia (LBD).

Embodiment 40b is the method of any of Embodiments 34 to 39, wherein the neurodegenerative disease or disorder is Alzheimer's disease, progressive supranuclear palsy (PSP), frontotemporal dementia and parkinsonism linked to chromosome 17 (FTDP-17), or Pick's disease and PART (primary age-related tauopathy).

Embodiment 40c is the method of any of Embodiments 34 to 39, wherein the neurodegenerative disease or disorder is Alzheimer's disease, Parkinson's Disease, Down's Syndrome, frontotemporal dementia and parkinsonism linked to chromosome 17 (FTDP-17), Corticobasal Degeneration, Dementia Lewy Amyotrophic Lateral sclerosis, Myotonic disphasy, chronic traumatic encephalopathy (CTE), Cerebral angiopahty, Primary age-related tauopathy (PART), or Lewy body dementia (LBD).

Embodiment 41 is a kit comprising at least one of the pharmaceutical composition of Embodiment 24 and the pharmaceutical composition of Embodiment 33, 33a or 33b.

Embodiment 42 is a helper T cell epitope consisting of an amino acid sequence selected from the group consisting of SEQ ID NO:13 to SEQ ID NO:17.

Embodiment 43 is a pharmaceutical composition comprising the helper T cell epitope of Embodiment 42.

Embodiment 44 is a method of enhancing an immune response to an antigen in a subject in need thereof, comprising administering to the subject the antigen together with the pharmaceutical composition of Embodiment 43.

EXAMPLES

The following examples of the invention are to further illustrate the nature of the invention. It should be understood that the following examples do not limit the invention and that the scope of the invention is to be determined by the appended claims.

The experimental methods used in the following examples, unless otherwise indicated, are all ordinary methods. The reagents used in the following embodiments, unless otherwise indicated, are all purchased from ordinary reagent suppliers.

Example 1: Preparation of Liposomal Vaccines

Preparation of the Control Liposomal Vaccine (Ethanol Injection Technique)

The control liposomal vaccine was produced by Ethanol (EtOH) Injection technique followed by extrusion. First, DMPC (Lipoid GmbH, Ludwigshafen, Germany), DMPG (Lipoid GmbH, Ludwigshafen, Germany), cholesterol (Dishman, Netherlands) and MPLA (Avanti Polar Lipids, AL, USA) were solubilized at a molar ratio of 9:1:7:0.05 in a 20:1 (V/V) mixture of EtOH and tert-butanol (t-BuOH) at 60° C. The lipid/ethanol solution was diluted in phosphate buffer saline (PBS) pH 7.4 at 60° C. to maintain 10% EtOH concentration and resulting in the formation of multilamellar liposome vesicles (MLVs). The MLVs were then submitted to 5 sequential passes of extrusion through three polycarbonate filters (Whatman) with a pore size of 0.08 um in series using Emulsiflex-05 (Avestin, Canada). The resulting liposomes were diluted in PBS pH 7.4 and heated to 60° C. to obtain a liposome solution prior to tau peptide addition.

An acetate tetrapalmitoylated phosphorylated tau peptide of SEQ ID NO: 2 (Bachem AG, Switzerland), herein referred to as the active pharmaceutical ingredient (API), was dissolved in PBS at pH 11.4 with 2.0% octyl β-D-glucopyranoside (Sigma-Aldrich, USA) at a concentration of 1 mg/mL, and the peptide solution was injected into the liposome solution at 60° C. followed by stirring for 30 minutes at 60° C. Concentration was done through ultrafiltration to a target final volume, and buffer exchange was carried out 10 times with PBS pH 7.4 during diafiltration. The resulting liposomes, with the API presented on the surface of the liposomes, were then sterile filtered by passing through two 0.2 um polycarbonate syringe filters in series, and the final product was stored at 5° C.

Preparation of the Liposome X, Y, Z and $Z^+$ Vaccines

The Liposome X and Y vaccines were produced by thin-lipids film technology followed by homogenization and extrusion.

The Liposome $Z^+$ vaccines, with a final API concentration of 1200 ug/ml and final T50 concentration of 1200 ug/ml were produced by Ethanol Injection technique followed by extrusion and the liposome Z vaccines, with a final API concentration of 400 ug/ml and final T50 concentration of 100 ug/ml, were produced by thin-lipids film technology followed by homogenization and extrusion.

The Liposome $Z^{++}$ vaccine, with a final API concentration of 400 ug/ml and final T50 concentration of 400 ug/ml, was produced by thin-lipids film technology followed by homogenization and extrusion.

The Liposome $Z^{+++}$ vaccine, with a final API concentration of 1200 ug/ml and final T50 concentration of 300 ug/ml, were produced by Ethanol Injection technique followed by extrusion.

Preparation of Liposome X, Y, Z and $Z^{++}$ Vaccines by Thin Lipid Film Technique The Liposome X, Y, Z and $Z^{++}$ vaccines were produced by thin-lipids film technology followed by homogenization and extrusion. First, DMPC (Lipoid GmbH, Ludwigshafen, Germany), DMPG (Lipoid GmbH, Ludwigshafen, Germany), cholesterol (Dishman, Netherlands) and monophosphoryl hexa-acyl Lipid A 3-deacyl synthetic (3D-(6-acyl) PHAD®) (Avanti Polar Lipids, AL, USA) were solubilized at a molar ratio of 9:1:7:0.05 in EtOH at 60° C., with the exception of Liposome Y, which did not contain 3D-(6-acyl) PHAD®. Ethanol was evaporated under vacuum rotavapor to obtain thin lipid film.

Lipid film was rehydrated with PBS pH 7.4, 5% DMSO (all Sigma-Aldrich) containing 0.15 mg/mL T50 peptide (Peptides & Elephants, Germany). The sample was gently stirred for 15 min and was further vigorously vortexed to dissolve the thin lipid film. Resulting multilamellar vesicles were subjected to 10 freeze-thaw cycles (liquid $N_2$ and waterbath at 37° C.) and submitted to homogenization followed by sequential extrusion through polycarbonate membranes (Whatman, UK) with a pore size of 0.08 um. Both the homogenization and extrusion steps were done in an EmulsiFlex-05 (Avestin, Canada). Extruded liposomes with encapsulated T50 peptide were concentrated by ultrafiltration, and buffer was exchanged to PBS pH 7.4 by diafiltration. The resulting liposomes were diluted in PBS pH 7.4 and heated to 60° C. to obtain a liposome solution prior to tau peptide and adjuvant addition.

CpG2006-Cholesterol (CpG2006-Chol) (Microsynth, Switzerland) is a DNA oligonucleotide with all internucleotide linkages as thiophosphate that is modified at 5' terminus with a Cholesterol molecule through a phosphate bond by means of a PEG spacer. CpG2006-Cholesterol (CpG2006-Chol) (Microsynth, Switzerland) was dissolved in PBS pH 7.4 at 1 mg/mL and injected into the liposome solutions (with the exception of Liposome X, which does not contain CpG2006-Chol) followed by incubation for 15 minutes before insertion of the API.

The API (Bachem AG, Switzerland) was dissolved in PBS pH 11.4 with 2% Octyl B-D-glucopyranoside (Sigma-Aldrich, USA) at a concentration of 1 mg/mL, and the peptide solution was injected into the liposome solution at 60° C. followed by stirring for 30 min at 60° C. Concentration was done through ultrafiltration to obtain the target value (400 ug/ml API and 100 ug/ml T50 for liposome X, Y, Z; and 400 ug/ml API and 400 ug/ml T50 for Liposome $Z^{++}$), and buffer exchange was carried out 10 times with PBS pH 7.4 during diafiltration. The resulting liposomes with the API presented on the surface of the liposomes were then sterile filtered by passing through 0.2 um polycarbonate syringe filters, and the final product was stored at 5° C.

Preparation of Liposome O by Ethanol Injection Technique

The Liposome O vaccine was produced by Ethanol (EtOH) Injection technique followed by extrusion. First, DMPC (Lipoid GmbH, Ludwigshafen, Germany), DMPG (Lipoid GmbH, Ludwigshafen, Germany), cholesterol (Dishman, Netherlands) and MPLA (Avanti Polar Lipids, AL, USA) were solubilized at a molar ratio of 9:1:7:0.05 in a 20:1 (V/V) mixture of EtOH and tert-butanol (t-BuOH) at 60° C. The lipid/ethanol solution was diluted in phosphate buffer saline (PBS) pH 7.4 at 60° C. to maintain 10% EtOH concentration and resulting in the formation of multilamellar liposome vesicles (MLVs). The MLVs were then submitted to 5 sequential passes of extrusion through three polycarbonate filters (Whatman) with a pore size of 0.08 um in series using Emulsiflex-05 (Avestin, Canada). The resulting liposomes were diluted in PBS pH 7.4 and heated to 60° C. to obtain a liposome solution prior to tau peptide addition.

T46 peptide (Pepscan, the Netherlands) was dissolved in PBS pH 7.4 at 1 mg/mL and injected into the liposome solutions followed by incubation for 15 minutes before insertion of the API.

The API (Bachem, Switzerland) was dissolved in PBS pH 11.4 with 2% Octyl ß-D-glucopyranoside (Sigma-Aldrich, USA) at a concentration of 1 mg/mL, and the peptide solution was injected into the liposome solution at 60° C. followed by stirring for 30 min at 60° C. Concentration was done through ultrafiltration to obtain the target value (400 ug/ml API and 100 ug/ml T46), and buffer exchange was carried out 10 times with PBS pH 7.4 during diafiltration. The resulting liposomes with the API presented on the surface of the liposomes were then sterile filtered by passing through 0.2 um polycarbonate syringe filters, and the final product was stored at 5° C.

Preparation of Liposome $Z^+$ and Liposome $Z^{+++}$ Vaccines by Ethanol Injection The Liposome $Z^+$ and Liposome $Z^{+++}$ vaccines were produced using an ethanol injection based process. First, DMPC (Lipoid GmbH, Ludwigshafen, Germany), DMPG (Lipoid GmbH, Ludwigshafen, Germany), cholesterol (Dishman, Netherlands) and 3D-(6-acyl) PHAD® (Avanti Polar Lipids, AL, USA) were solubilized at a molar ratio of approximately 9:1:7:0.04 in EtOH at 60° C. T50 peptide (Bachem AG, Switzerland) was dissolved in 10 mM His/270 mM sucrose (pH 5.8-6.0). Then, the lipid ethanol solution was injected into the solution containing T50 peptide and gently stirred for 15 min, resulting in multilamellar vesicles (MLVs). MLVs were submitted to homogenization (6 times for Liposome $Z^+$, and no homogenization for Liposome $Z^{+++}$) followed by sequential extrusion through polycarbonate membranes (Whatman, UK) with a pore size of 0.08 um (5 passes for Liposome $Z^+$, 3-5 times for Liposome $Z^{+++}$). Both the homogenization and extrusion steps were done in an EmulsiFlex-05 (Avestin, Canada) for Liposome $Z^+$. Extrusion of Liposome $Z^{+++}$ was done using LIPEX filter extruder. Extruded liposomes were concentrated by ultrafiltration, and buffer was exchanged to 20 mM His/145 mM NaCL pH 7.4 by diafiltration. The resulting liposomes with encapsulated T50 peptide were diluted in 20 mM His/145 mM NaCL pH 7.4 and heated to 60° C. to obtain a liposome solution prior to the additions of the API and the adjuvant.

CpG2006-Chol (Microsynth, Switzerland for Liposome $Z^+$; Avecia, USA for Liposome $Z^{+++}$) was dissolved in 20 mM His/145 mM NaCl pH 7.4 at 1 mg/mL and injected into the liposome solution followed by incubation for 15 minutes before insertion of the API.

The API (Bachem AG, Switzerland) was dissolved in carbonate buffer pH 10.2 with 1% Octyl ß-D-glucopyranoside (Sigma-Aldrich, USA), at a concentration of 1 mg/mL, and the peptide solution was injected into the liposome $Z^+$ solution at 60° C. followed by stirring for 30 min at 60° C. The peptide solution was mixed into the liposome $Z^+$ solution using T-Line Mixing at 60° C. followed by stirring for 30 min at 60° C. Concentration was done through ultrafiltration to obtain the target value (1200 ug/ml API and 1200 ug/ml T50 for Liposome $Z^+$; and 1200 ug/ml API and 300 ug/ml T50 for Liposome $Z^{+++}$), and buffer exchange was carried out 10 times with 10 mM His/270 mM Sucrose pH 6.5 during diafiltration. The resulting $Z^+$ liposomes with the API presented on the surface of the liposomes and the resulting $Z^{+++}$ liposomes with the API presented on the surface of the liposomes were then sterile filtered by passing through 0.2 um polycarbonate syringe/capsule filters, and the final product was stored at 5° C.

Preparation of the Liposome L, M, & N Vaccines

The Liposome L, M, and N vaccines were produced by thin-lipids film technology followed by homogenization and extrusion. First, DMPC (Lipoid GmbH, Ludwigshafen, Germany), DMPG (Lipoid GmbH, Ludwigshafen, Germany), cholesterol (Dishman, Netherlands), and MPLA (Avanti Polar Lipids, AL, USA) were solubilized at a molar ratio of 9:1:7:0.05 in EtOH at 60° C. Ethanol was evaporated under vacuum rotavapor in order to obtain thin lipid film.

Lipid film was rehydrated with PBS pH 7.4, 5% DMSO (all Sigma-Aldrich) containing either:
  0.15 mg/mL T48 peptide (Peptides&Elephants, Germany)—for Liposome M; or
  0.13 mg/mL T50 peptide (Peptides&Elephants, Germany)—for Liposome L; or
  0.15 mg/mL T52 peptide (Peptides&Elephants, Germany)—for Liposome N.

The sample was gently stirred for 15 min and was further vigorously vortexed to dissolve the thin lipid film. Resulting multilamellar vesicles were subjected to 10 freeze-thaw cycles (liquid $N_2$ and waterbath at 37° C.) and submitted to homogenization followed by sequential extrusion through polycarbonate membranes (Whatman, UK) with a pore size of 0.08 um. Both the homogenization and extrusion steps were done in an EmulsiFlex-05 (Avestin, Canada). Extruded liposomes were concentrated by ultrafiltration, and buffer was exchanged to PBS pH 7.4 by diafiltration. The resulting liposomes with encapsulated T48, T50 or T52 peptide were diluted in PBS pH 7.4 and heated to 60° C. to obtain a liposome solution prior to tau peptide addition.

The API (Bachem AG, Switzerland) was dissolved in PBS pH 11.4 with 2% Octyl B-D-glucopyranoside (Sigma-Aldrich, USA) at a concentration of 1 mg/mL and the peptide solution was injected into the liposome solution at 60° C. followed by stirring for 30 min at 60° C. Concentration was done through ultrafiltration to obtain a target value (400 ug/ml API and 100 ug/ml T48, T50 or T52) and buffer exchange was carried out 10 times with PBS pH 7.4 during diafiltration. The resulting liposomes with the API presented on the surface of the liposomes were then sterile filtered by passing through 0.2 um polycarbonate syringe filters and the final product was stored at 5° C.

Preparation of the Liposome R, S and T Vaccines

The Liposome R, S and T vaccines were produced using an ethanol injection based process followed by extrusion. First, DMPC (Lipoid GmbH, Ludwigshafen, Germany), DMPG (Lipoid GmbH, Ludwigshafen, Germany), cholesterol (Dishman, Netherlands) and 3D-(6-acyl) PHAD® (Avanti Polar Lipids, AL, USA) were solubilized at a molar ratio of 9:1:7:0.04 in EtOH at 60° C. For Liposome R and T, the above lipid ethanol solution was mixed to the 10 mM histidine pH 5.8 supplemented by 270 mM sucrose to reach 10% solvent (EtOH) and then incubated for 30 minutes at 60° C. For Liposome S, T50 peptide (Bachem AG, Switzerland) was dissolved in 10 mM His/270 mM sucrose (pH 5.8-6.0). Lipid-buffer mix related to Liposome R, S and T were gently stirred for 15 min, resulting in multilamellar vesicles (MLVs). The resulting multi lamellar vesicles were submitted to extrusion through polycarbonate membranes (Whatman, UK) with a pore size of 0.08 um (5x) done in an EmulsiFlex-05 high pressure system (Avestin, Canada).

Extruded liposomes were concentrated by ultrafiltration, and buffer was exchanged to 20 mM His/145 mM NaCL pH 7.4 by diafiltration. The resulting liposomes with encapsulated T50 for Liposome S and the resulting Liposomes R and T were further diluted in 20 mM His/145 mM NaCL pH 7.4 and heated to 60° C. to obtain a liposome solution prior to the additions of the API and T57 for Liposome T.

For Liposome T, T57 was dissolved to 1 mg/mL in 1% Octyl ß-D-glucopyranoside (Sigma-Aldrich, USA) in deionized distilled water and inserted in liposome followed by incubation for 15 minutes at 60° C. before API insertion.

The API (Bachem AG, Switzerland) was dissolved in carbonate buffer pH 10.2 with 1% Octyl ß-D-glucopyranoside (Sigma-Aldrich, USA), at a concentration of 1 mg/mL, and the peptide solution was mixed into the liposome solution at 60° C. followed by stirring for 30 min at 60° C. Concentration was done through ultrafiltration to obtain the following target value:

1200 ug/ml API for Liposome R;
1200 ug/ml API and 300 ug/ml T50 for Liposome S; and
1200 ug/ml API and 300 ug/ml T57 for Liposome T;

Buffer exchange was carried out 10 times with 10 mM His/270 mM Sucrose pH 6.5 during diafiltration. The resulting liposomes with the API presented on the surface of the liposomes were then sterile filtered by passing through 0.2 um polycarbonate syringe filters, and the final product was stored at 5° C.

Example 2: Preparation of Conjugate Vaccine

Peptides and Adjuvants

Sequences of two multi-phosphorylated peptide epitopes (TAUVAC-p7.1 and TAUVAC-p22.1 which have three and two phosphorylated amino acids, respectively) were refined by optimizing the length such that they might better bind surface immunoglobulin of B cells, and such that the sequences did not contain epitopes predicted to bind human HLA class I A, B, and C molecules with high affinity. The latter criterion was important to avoid the induction of a cytotoxic CD8$^+$ T cell response against tau that could potentially cause significant neuronal damage. Using the T cell epitope prediction tool of the Immune Epitope Database and Analysis Resources, peptide TAUVAC-p7.1 showed no predicted epitopes capable of binding to human HLA class I A, B, C and HLA class II DQ and DR molecules with high affinity, while peptide TAUVAC-p22.1 was predicted to contain epitopes binding to HLA class II DQ and DR molecules with intermediate/high affinity (data not shown).

Phosphorylated tau peptides (SEQ ID NO: 1, SEQ ID NO: 2, SEQ ID NO: 3) used in this study were produced synthetically (Pepscan, NL) with the phospho-residues added during synthesis. A conjugate comprising phosphorylated tau peptide having the amino acid sequence of SEQ ID NO: 1 or SEQ ID NO: 3 covalently linked to a KLH carrier via a linker is herein referred to as Conjugate B or Conjugate C, respectively. A conjugate comprising phosphorylated tau peptide having the amino acid sequence of SEQ ID NO: 2 covalently linked to a CRM carrier via a linker is herein referred to as Conjugate A.

To manufacture Conjugates B and C, vaccine peptides were conjugated to the carrier protein KLH via a m-maleimidobenzoyl-N-hydroxysuccinimide ester (MBS) linker and an extra cysteine on the N-terminus of the peptide. The unbound peptide was removed using a Sephadex G25 column before concentrating the conjugate. Conjugates were mixed before injection to either a potent multicomponent adjuvant (Sigma Adjuvant System, Sigma-Aldrich) or a single component depot adjuvant (aluminium hydroxide, Alhydrogel®, Invivogen) following manufacturer's instructions.

Vaccine peptides were conjugated to the carrier protein CRM197 via a polyethylene glycol (PEG)-cysteine-acetamidopropionamide linker. Phosphorylated tau peptide having the amino acid sequence of SEQ ID NO: 2 was produced synthetically (Polypeptide Laboratories SAS), with phospho-residues and PEG3 spacer added during synthesis. Conjugate A was manufactured by conjugating the carrier protein CRM197 via a succinimidyl 3-(bromoacetamide) propionate (SBAP) linker to a cysteine on the N-terminus of the peptide. SBAP was ligated to CRM197 protein primary amines (—NH2) via NHS ester reaction chemistry. The excess SBAP linker was removed using ultrafiltration and diafiltration (UF/DF). The CRM197-SBAP intermediate was conjugated to the phosphorylated tau peptide, and once the reaction was completed, the conjugation reaction was terminated by adding excess amount of L-cystine to quench the reaction. The crude CRM197-peptide conjugated product was purified using a Capto Q ImpRes (GE Healthcare) chromatography column and eluted using a salt isocratic method. The purified CRM197-peptide product was then formulated into 20 mM Tris, 250 mM Sucrose, pH 8.1 to a concentration of 0.5 mg/mL using UF/DF. The CRM197-tau peptide Drug Substance (DS) was generated by adding a 10% PS80 stock buffer to reach a final concentration of 0.01% PS80. The solution was thoroughly mixed prior to filtering.

Example 3: Vaccine Induced IgG Antibodies Specific to Tau Phosphopeptide

All animal experiments were approved and performed in accordance with local legislation on animal experiments. Rhesus macaques (Macaca mulatta) were obtained from Kunming Biomed International Ltd, China, Yunnan Yinmore Bio-Tech Co. LTD, China and Yunnan Laboratory Primates Inc., China. Animals were two to five years old at the start of immunization, and their minimum weight was 2.5 kg. A detailed clinical examination was performed prior to initiation of the treatment and weekly thereafter. Moreover, macaques were observed twice per day, and clinical signs were recorded.

Adult Rhesus macaques (n=3 males and 3 females per group) were immunized subcutaneously with 1800 μg of acetate tetrapalmitoylated phosphorylated tau peptide of SEQ ID NO: 2 per dose of the control liposomal vaccine (liposome with tetrapalmitoylated phosphorylated tau peptide of SEQ ID NO: 2 and MPLA) or a liposomal vaccine according to embodiment of the application, e.g., Liposome Z (liposome with tetrapalmitoylated phosphorylated tau peptide of SEQ ID NO: 2, 3D-(6-acyl) PHAD®, lipidated CpG oligonucleotide CpG 2006 and T-cell peptide T50) or 15 μg per dose of a conjugate vaccine according to an embodiment of the invention (e.g., Conjugate A, phosphorylated tau peptide of SEQ ID NO: 2 linked to CRM197) co-injected with alum and CpG oligonucleotide CpG 2006 at days 1, 29 and 85. Bleedings were performed before immunization and at days 8, 22, 36, 50, 64, 78, 92, 106, 120, 134 and 148, and the sera were isolated.

Specific IgG antibody titers were determined by ELISA, using phosphorylated tau peptide of SEQ ID NO: 2 as the coating antigen. Serum from individual immunized monkey was serially diluted in assay buffer (PBS, 0.05% Tween® 20, 1% BSA) and applied to 96-well plates that had been coated with the relevant peptide. After two hour incubation, samples were removed and plates washed in PBST (PBS, 0.05% Tween® 20). Antibodies were detected using an HRP conjugated anti-monkey IgG (KPL), followed by ABTS substrate (Roche). All samples were run in eight two-fold dilutions, with positive and negative control samples included on each plate. The data was expressed as geometric mean of end-point titers (last serum dilution inducing a positive response) per group.

Figure 4:
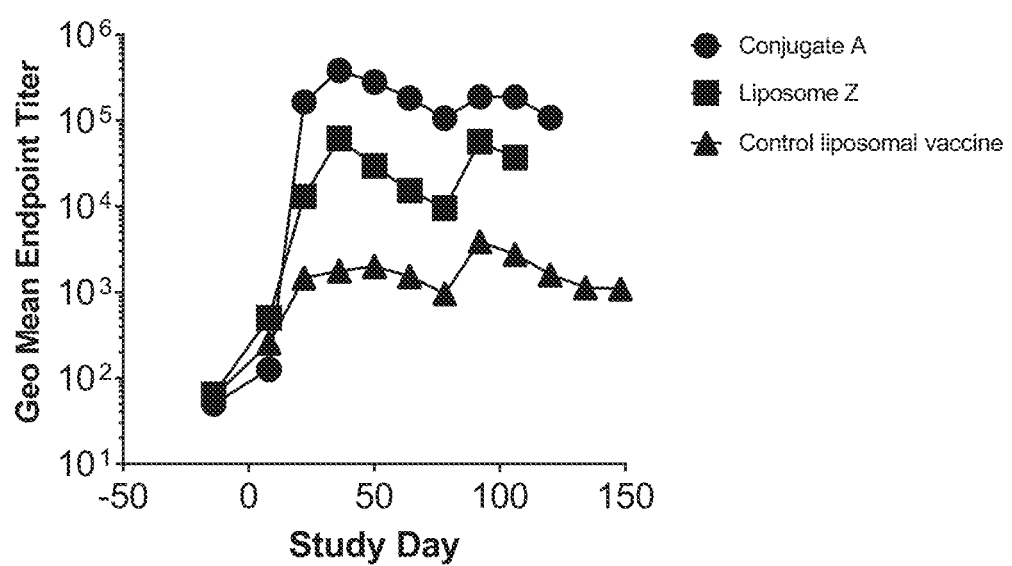
FIG. 4 shows that tau vaccines according to embodiments of the invention induce sustained high titer anti-phosphorylated tau antibodies in Rhesus macaque: the geometric mean of end-point titers per group, as measured by enzyme-linked immunosorbent assay (ELISA), over time, is higher for a vaccine comprising a liposome (Liposome Z) according to an embodiment of the invention or a vaccine comprising a conjugate (Conjugate A) according to an embodiment of the invention, as compared to a control liposomal vaccine without the helper T-cell epitope.

As shown in FIG. 4, both the Liposome Z vaccine and the Conjugate A induced higher phosphopeptide-specific IgG titers, as compared to the control liposomal vaccine.

Example 4: Vaccine Induced Antibodies Specific to Pathological Tau Structures in Human Brain All brain tissues were obtained from the Netherlands Brain Bank (NBB) and were collected from donors following signature of an informed consent for a brain autopsy and the use of the samples as well as their clinical information for research purposes. Paraffin sections from non-demented controls (healthy), Alzheimer's disease (AD), frontal temporal dementia with tau pathology (FTD-tau), Pick's disease, primary age-related tauopathy (PART) and progressive supranuclear palsy (PSP) were used. Brain regions included parietal cortex, middle frontal gyms, hippocampus or the caudate nucleus.

In particular, formalin-fixed paraffin embedded sections from parietal cortices of a control human subject (healthy) and a human subject suffering from Alzheimer's disease (AD Braak V/VI) were stained with post-immune macaque serum diluted 1:100 in normal antibody diluent (Immunologic). The sections were then washed and stained with a Goat anti-monkey-HRP (Abcam). The staining was finally visualized using 3,3'-diaminobenzidine (DAB; Dako) which deposits a brown specific stain in the presence of horse radish peroxidase (HRP). Slides were counterstained with haematoxylin, dehydrated and mounted with Quick D mounting medium (Klinipath). Pictures were taken with a Leica DC500 microscope.

Figure 5:
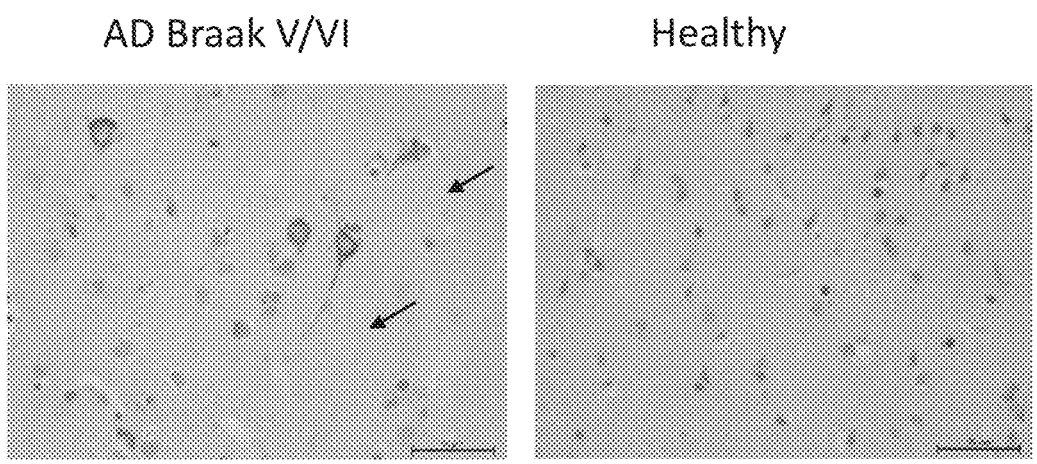
FIG. 5 shows that serum from Rhesus macaques immunized with a liposome (Liposome Z) according to an embodiment of the invention binds to pathological tau structures in human AD brain sections (left panel) as compared to healthy human brain sections (right panel)

Results in FIG. 5 show that post-immune sera from Rhesus macaques immunized with Liposome Z (liposome with tetrapalmitoylated phosphorylated tau peptide of SEQ ID NO: 2, 3D-(6-acyl) PHAD®, lipidated CpG oligonucleotide CpG 2006 and T-cell peptide T50) stained pathological tau structures in human brain sections. Serum was collected from Rhesus macaques at day 106 after the primary immunization with the improved liposomes. This macaque received immunizations at month 0, 1, and 3 prior to serum collection. The left (AD Braak V/VI) panel shows staining of parietal cortex from a Braak Stage V donor. Arrows indicate staining of tau tangles. The right (Healthy) panel shows staining of parietal cortex from a Braak Stage 0 donor. Serum was applied to sections at a 1:100 dilution, followed by goat anti-monkey antibody at 1:100, and staining was visualized using a DAB developer.

Figure 6:
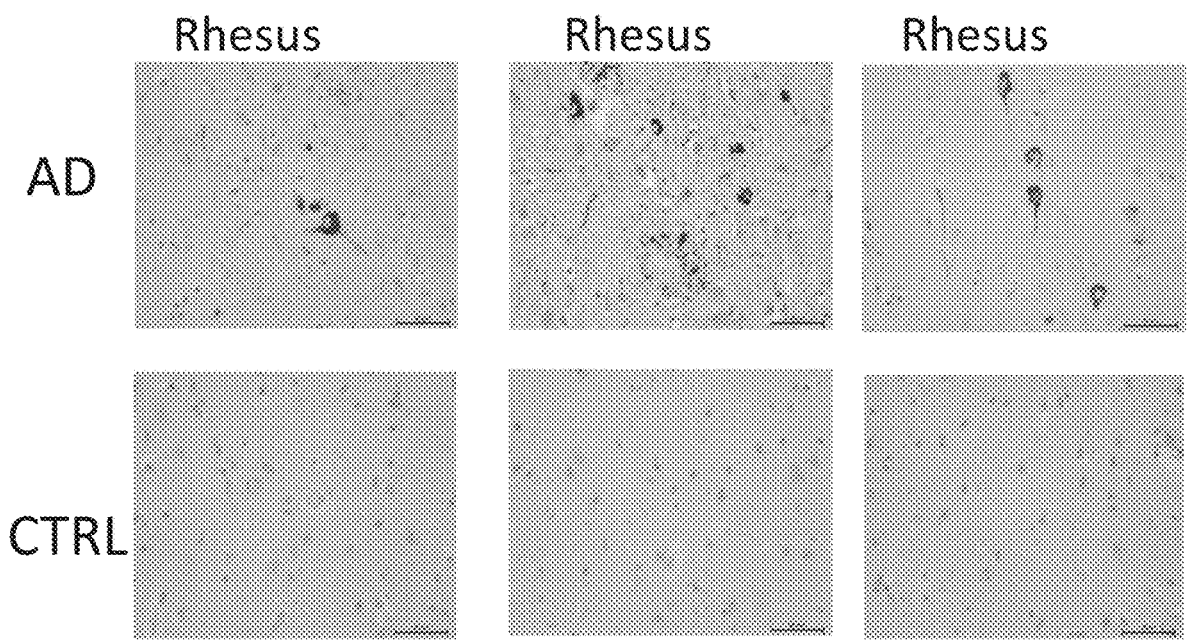
FIG. 6 shows that serum from Rhesus macaques immunized with a conjugate (Conjugate A) according to an embodiment of the invention formulated in a composition containing soluble CpG and alum hydroxide binds to pathological tau structures in human AD brain sections (top row), as compared to healthy human brain sections (bottom row)

Results in FIG. 6 show that serum from Rhesus macaques immunized with Conjugate A which contains phosphorylated tau peptide of SEQ ID NO: 2 plus soluble CpG and alum hydroxide binds to pathological tau structures in human AD brain sections. Serum was collected at day 106 after the primary immunization with the CRM conjugate vaccine. These macaques received immunizations at month 0, 1, and 3 prior to serum collection. The upper (AD) panels show staining of parietal cortex, including tau tangles, from a Braak Stage V donor. The lower (CTRL) panels show staining of parietal cortex from a Braak Stage 0 donor. Serum was applied to sections at a 1:100 dilution, followed by goat anti-monkey antibody at 1:100, and staining was visualized using a DAB developer.

Example 5: Liposomal Vaccines with One or Two Adjuvants

Addition of two adjuvants in the improved liposomal vaccine increases the level of tau phosphopeptide-specific IgG antibody titers, as well as the consistency of antibody response between individuals.

Figure 7A:
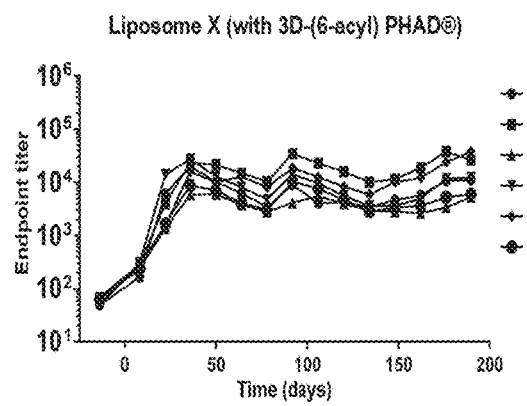
FIG. 7A shows the titers of anti-phosphorylated tau antibodies induced by Liposome X with a TLR4 ligand, MPLA (3D-(6-acyl) PHAD®) alone as the adjuvant.
Figure 7B:
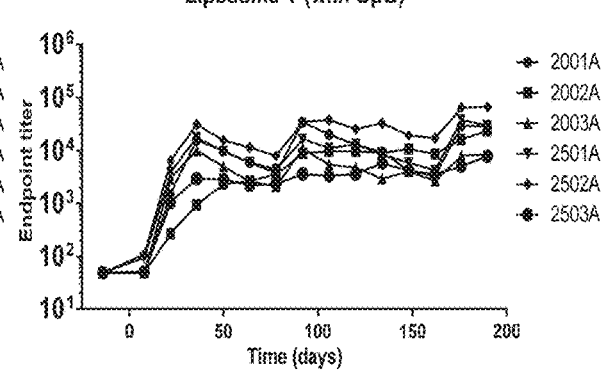
FIG. 7B shows the titers of anti-phosphorylated tau antibodies induced by Liposome Y with a TLR9 ligand (lipidated CpG oligonucleotide) alone as the adjuvant.
Figure 7C:
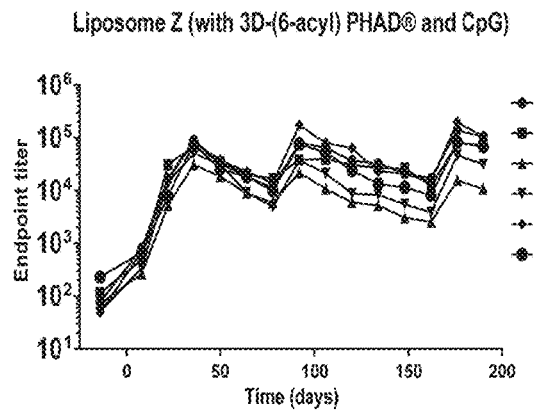
FIG. 7C shows the titers of anti-phosphorylated tau antibodies induced by Liposome Z with a combination of a TLR4 ligand, MPLA (3D-(6-acyl) PHAD®) and a TLR9 ligand (lipidated CpG oligonucleotide) as the adjuvants, which also shows that the combination of two adjuvants induces less variability in antibody titers among individual monkeys.
Figure 7D:
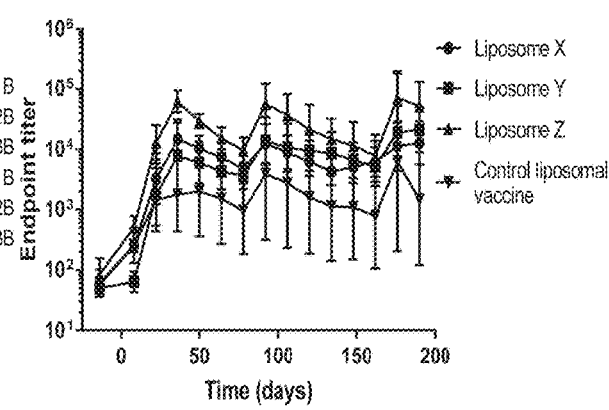
FIG. 7D presents the geometric mean of antibody titers of the above-mentioned immunization groups and a control liposomal vaccine with a TLR4 ligand, MPLA, but without T-cell epitope, and shows that the vaccines according to embodiments of the invention result in higher antibody titers of anti-phosphorylated tau antibodies than a control liposomal vaccine: titers were measured by ELISA and are presented in geometric mean+/− 95% confidence interval of end point titers per group over time.

Adult Rhesus macaques (n=3 males and 3 females per group) were immunized subcutaneously at days 1, 29, 85 and 169 with 1800 μg of acetate tetrapalmitoylated phosphorylated tau peptide of SEQ ID NO: 2 per dose of the control liposomal vaccine or the improved liposomal vaccine with encapsulated T50 T-cell epitope, containing either 3D-(6-acyl) PHAD® adjuvant alone (Liposome X, FIG. 7A), lipidated CpG 2006 oligonucleotide adjuvant alone (Liposome Y, FIG. 7B), or both 3D-(6-acyl) PHAD® and lipidated CpG 2006 oligonucleotide adjuvants (Liposome Z, FIG. 7C). Bleedings were performed before immunization and at days 8, 22, 36, 50, 64, 78, 92, 106, 120, 134, 148, 162, 176 and 190 and the sera were isolated. Specific IgG antibody titers in the sera were determined by ELISA, using phosphorylated tau peptide of SEQ ID NO: 2 as the coating antigen and an anti-monkey IgG secondary antibody. Resulting antibody levels are presented as end-point titers (last serum dilution inducing a positive response) for each individual monkey over time. Each immunization group is represented in one panel (FIG. 7A-C). Geometric mean of end-point titers per group±95% confidence interval is presented in FIG. 7D. In summary, FIGS. 7A-D show that inclusion of two adjuvants in the liposomal vaccine containing encapsulated T50 improved the level and consistency of antibody response to tau phosphopeptide, resulting in less variability in antibody response among individual monkeys. More specifically, as shown in FIG. 7D, improved liposomal vaccines with phosphorylated tau peptide of SEQ ID NO: 2, T50 T-cell epitope (Liposome X, Y and Z) and 1 or 2 adjuvants, induced higher titers against the tau phosphopeptide than the control liposomal vaccine with no T-cell epitope. All monkeys were responders when injected with each of the improved liposomal vaccines, while 4 out of 6 animals were responders with the control liposomal vaccine.

Example 6: Vaccines Induced Antibodies Specific to the Enriched Paired Helical Filaments (ePHF)

Groups of Rhesus macaques (n=3 males and 3 females per group) were immunized subcutaneously by vaccination at day 1 and day 29 with (i) the improved liposomal vaccine containing the T50 T-cell epitope and 3D-(6-acyl) PHAD® adjuvant alone (Liposome X), (ii) the improved liposomal vaccine containing the T50 T-cell epitope and lipidated CpG 2006 adjuvant alone (Liposome Y), (iii) the improved liposomal vaccine containing the T50 T-cell epitope and two adjuvants (3D-(6-acyl) PHAD® and lipidated CpG2006, Liposome Z), or (iv) the conjugate vaccine (phosphorylated tau peptide of SEQ ID NO: 2 linked to CRM197) co-injected with alum and CpG oligonucleotide CpG 2006 (Conjugate A).

Preparations of enriched paired helical filaments (ePHF) were obtained from post-mortem brain tissues of histologically confirmed AD subjects by sarcosyl extraction of insoluble tau, using a modified method of Greenberg and Davies (Greenberg and Davies, 1991, Proc Natl Acad Sci USA, 87(15):5827-31). Antibody titers specific for enriched paired helical filaments (ePHF) were evaluated using the Mesoscale Discovery (MSD) platform. MSD streptavidin plates were coated with the biotinylated anti-tau capturing antibody (HT7-biotin, ThermoScientific) before incubation with ePHF isolated from Alzheimer's disease patients, while the IgG antibodies specific for ePHF were further detected using a SulfoTag-labelled anti-human IgG antibody that cross-reacts with monkey IgG antibodies. More specifically, ePHF was added to MSD Gold small spot streptavidin 96-well plates (MSD) previously saturated with 1% BSA and coated with biotinylated HT-7 (Thermo Scientific). After one hour of incubation, plates were washed with PBST and serial dilutions of sera were added and incubated for two hours. Bound antibodies were detected using a SulfoTag labelled anti-human IgG antibody followed by a fixation step in 1% PFA before adding the Read Buffer T. Plates were analyzed using a Sector Imager (MSD). Results were expressed in Arbitrary units per milliliter (AU/mL) for each individual monkey, together with the geometric mean per group. Antibody titers specific for ePHF at Day 50 after the first immunization are represented.

Figure 8:
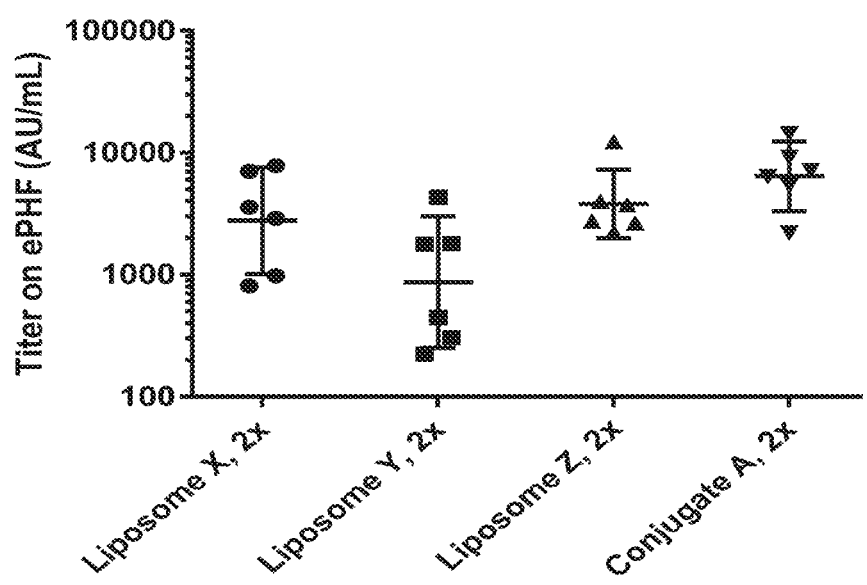
FIG. 8 shows that immunization using a liposomal vaccine (e.g., Liposome X, Y or Z) or a conjugate vaccine (Conjugate A) according to an embodiment of the invention induces antibody IgG titers specific for enriched paired helical filaments (ePHF) isolated from the post mortem brain of Alzheimer's disease patients: antibody titers were measured by Meso Scale Discovery (MSD) technology and are presented as values for individual monkeys on Day 50 and the geometric mean+/− 95% CI after the first immunization.

FIG. 8 shows that all of the vaccines induced high titers of ePHF-specific IgG antibodies.

Similar results with high titers of ePHF-specific IgG antibodies were also obtained with other liposomes, such as Liposome Z+, administered to Rhesus macaques via intramuscular administration.

Example 7: The Breadth of Tau Phosphopeptide-Specific Antibody Induced by the Liposomal Vaccine and Conjugate Vaccine in Rhesus Monkeys Groups of Rhesus macaques (n=3 males and 3 females per group) were immunized subcutaneously at days 1 and 29 with (i) the improved liposomal vaccine containing encapsulated T50 and two adjuvants: TLR4 ligand (3D-(6-acyl) PHAD®) and lipidated CpG 2006 oligonucleotide (Liposome Z), and (ii) the conjugate vaccine (phosphorylated tau peptide of SEQ ID NO: 2 linked to CRM) (Conjugate A) co-injected with alum and CpG oligonucleotide CpG 2006. The epitope recognition profile of antibodies was determined by epitope mapping ELISA three weeks after the second immunization (Day 50) using a library of N-terminally biotinylated 8-mer peptides, shifted by one amino acid and covering the sequence of phosphorylated tau peptide of SEQ ID NO: 2, as well as the sequence of SEQ ID NO: 4 (VYKSPVVSGDTSPRHL, non-phosphorylated tau peptide having the same amino acid sequence as SEQ ID NO: 2) and the corresponding biotinylated full length peptides.

Figure 9A:
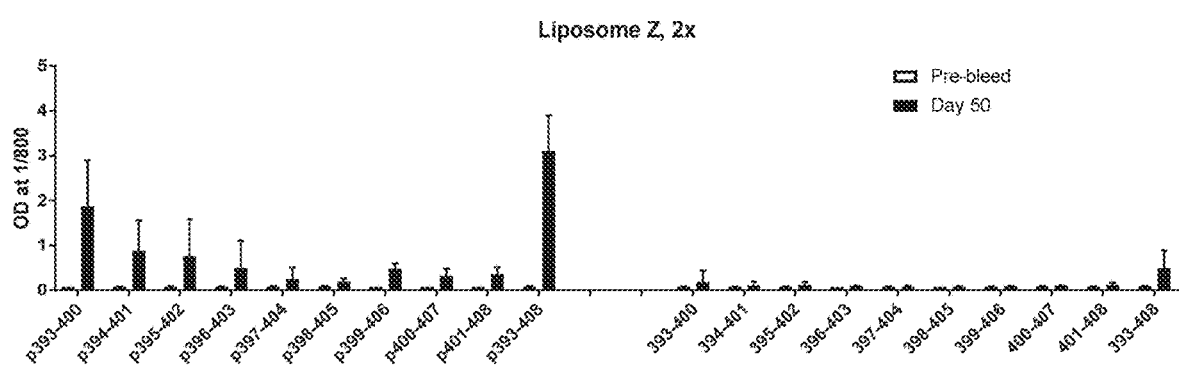
FIG. 9 shows that immunization with a liposomal vaccine according to an embodiment of the invention (Liposome Z) containing encapsulated T50 and a combination of a TLR4 ligand (3D-(6-acyl) PHAD®) and a TLR9 ligand (lipidated CpG oligonucleotide) as adjuvants induces antibodies that mostly bind the N-terminus of phosphorylated tau peptide of SEQ ID NO: 2 (FIG. 9A), whereas monkeys immunized with a conjugate vaccine according to an embodiment of the invention (Conjugate A) generate IgG antibodies that bind mostly to the C-terminal part of the peptide, for both phosphorylated peptide (left) and non-phosphorylated peptide (right) (FIG. 9B)
Figure 9B:
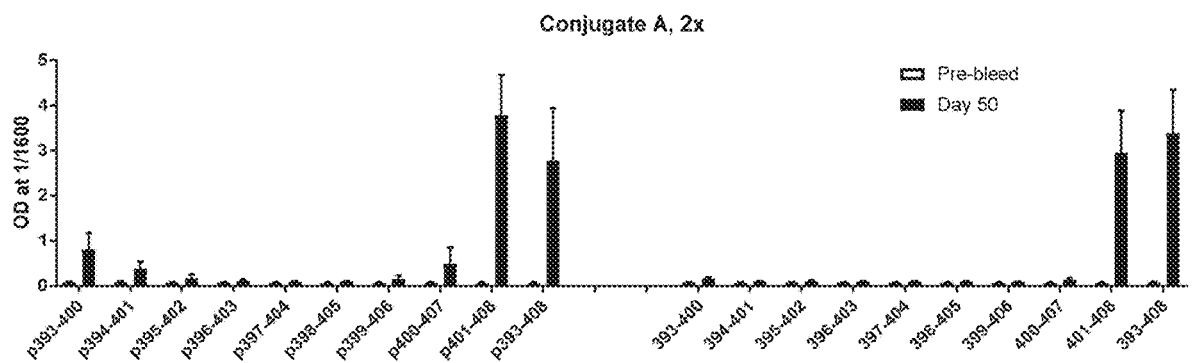

FIG. 9 shows that monkeys immunized with liposome Z produced IgG antibodies that bind mostly to the N-terminal part of the phosphorylated peptide of SEQ ID NO: 2 (FIG. 9A), whereas monkeys immunized with the conjugate vaccine (phosphorylated tau peptide of SEQ ID NO: 2 linked to CRM) generated IgG antibodies that bind mostly to the C-terminal part of the tau peptide of SEQ ID NO: 2 (FIG. 9B).

Figure 10A:
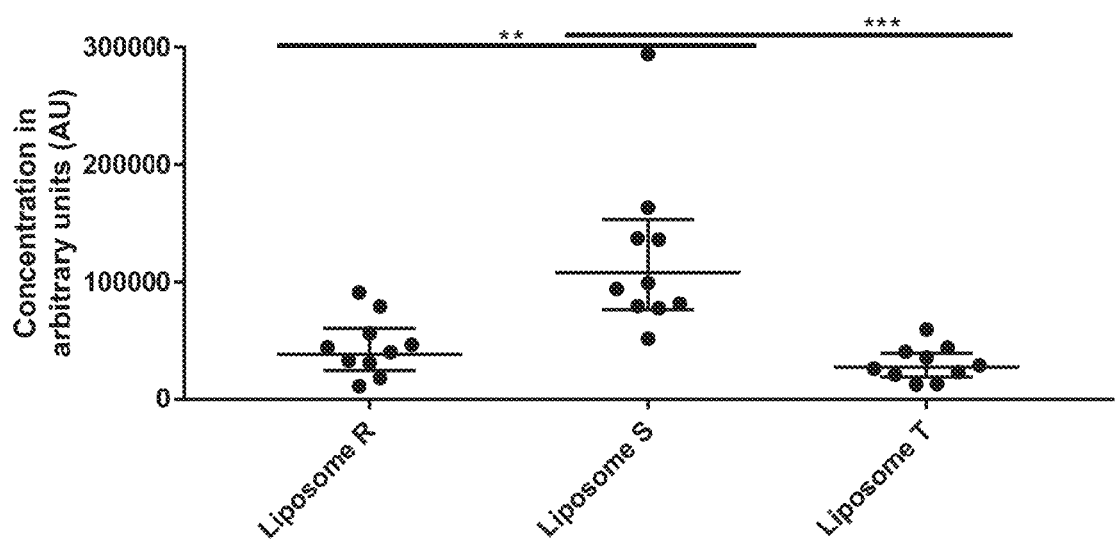
FIG. 10 A and B show that vaccination with a liposomal vaccine according to an embodiment of the invention containing encapsulated T-cell epitope T50 and TLR4 ligand (3D-(6-acyl) PHAD®) as adjuvant (Liposome S) induces significantly higher antibody titers than the control liposomal vaccine (with a TLR4 ligand, 3D-(6-acyl) PHAD®, but without T-cell epitope T50, Liposome R) and also the liposomal vaccine according to an embodiment of the invention containing surface T-cell epitope T57 (dipalmitoylated T50) and TLR4 ligand (3D-(6-acyl) PHAD®, Liposome T) in mice: antibody titers at day 21 (FIG. 10A) and 35 (FIG. 10B) after the first immunization were measured by ELISA and presented as individual values and the geometric mean per group±95% CI; (: p<0.01, *: p<0.001)
Figure 10B:
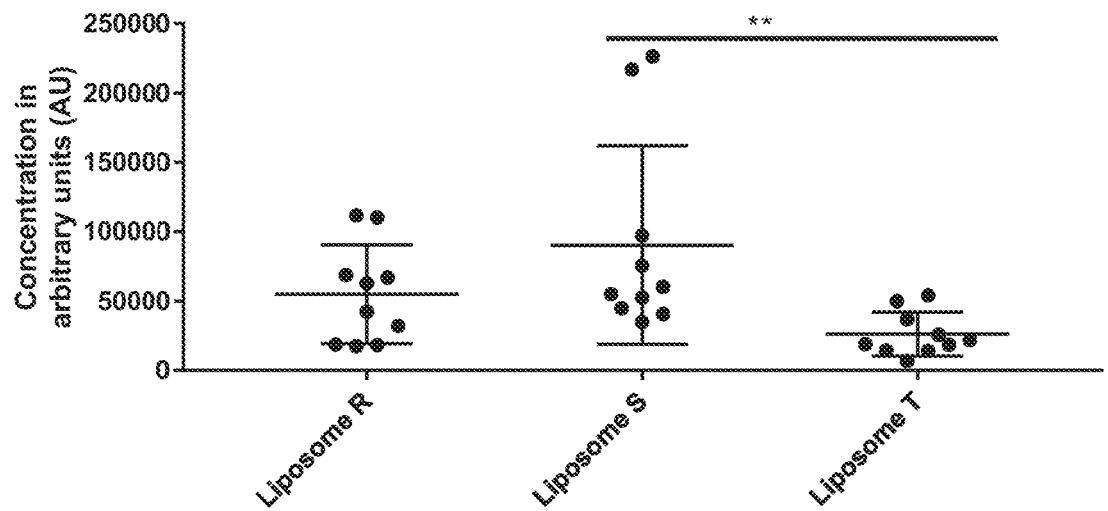

Example 8: Increased Titers of IgG Antibodies Specific to Tau Phosphopeptide Induced by Liposomal Vaccine with Encapsulated T-Cell Epitope Three groups of C57BL/6J mice (n=10 per group) were immunized subcutaneously at days 0 and 14 with i) liposomal vaccine containing TLR4 agonist (3D-(6-acyl) PHAD®), (Liposome R), ii) liposomal vaccine containing encapsulated T-cell epitope T50 and TLR4 ligand (3D-(6-acyl) PHAD®) as adjuvant, (Liposome S), or iii) liposomal vaccine containing anchored T-cell epitope T57 on the liposomal surface (i.e. dipalmitoylated T50) and TLR4 ligand (3D-(6-acyl) PHAD®) as adjuvant, (Liposome T). Level of IgG antibodies specific to phosphorylated tau peptide of SEQ ID NO: 2 was measured 21 and 35 days after the first injection in mouse plasma by ELISA; results were presented as values of individual mice, together with the geometric mean per group±95% CI expressed in arbitrary units (AU) per mL. As shown in FIG. 10A, vaccination with the liposomal vaccine containing encapsulated T50 (Liposome S) induced significantly higher antibody titers than the control liposomal vaccine (Liposome R) and the liposomal vaccine containing anchored T-cell epitope (Liposome T) 21 days after the first immunization (Kruskal-Wallis test: p=0.0089 and p=0002, respectively) and also higher antibody titers than the control liposomal vaccine and significantly higher antibody titers than the liposomal vaccine containing anchored T-cell epitope 35 days after the first immunization (Kruskal-Wallis test: p=0.7591 and p=0053, respectively) (FIG. 10B).

Figure 11A:
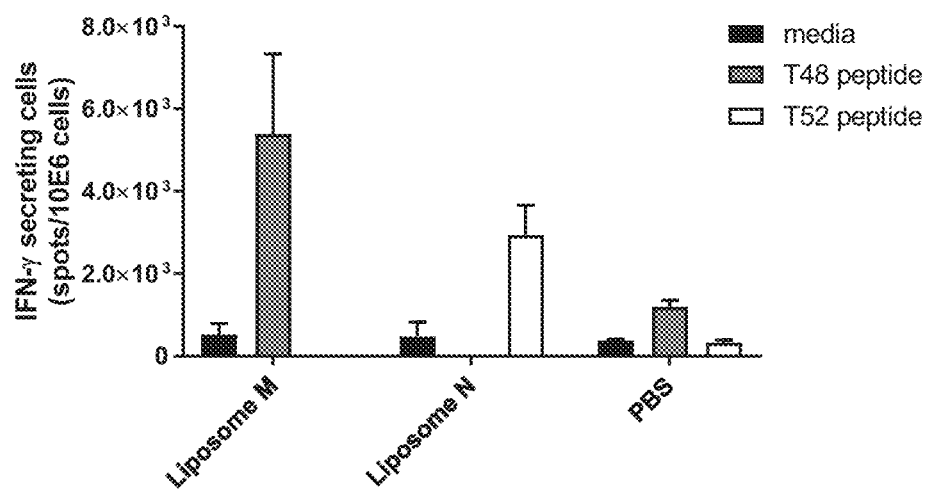
FIG. 11 shows that encapsulation of T-cell peptides T48 or T52 into the liposome (Liposome M or N, respectively) induces a T-cell response specific to the encapsulated peptide in mice: T-cell response was evaluated by IFN-γ (FIG. 11A) and IL-4 (FIG. 11B) ELISPOT.
Figure 11B:
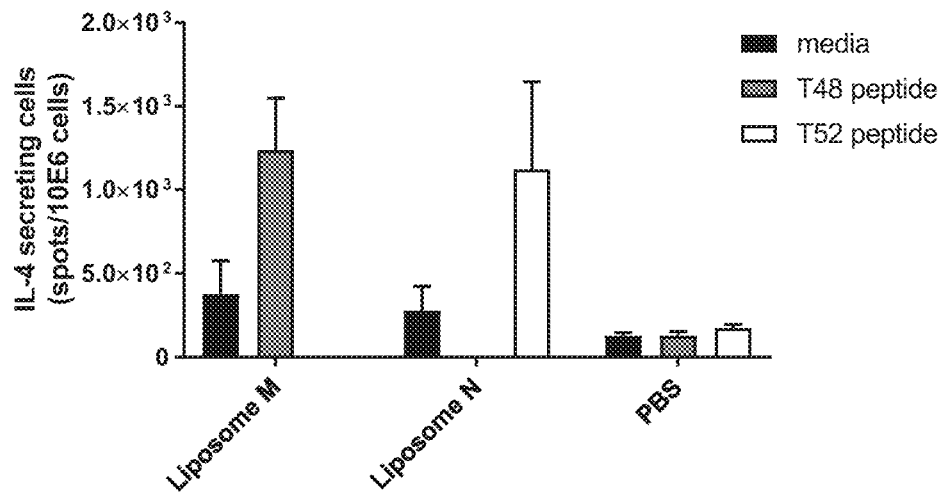

Example 9: Liposomal Vaccines Induced T-cell Response Specific to the Incorporated T-cell Epitope Three groups of C57BL/6J mice (n=5 per group) were immunized subcutaneously at days 0, 14 and 28 with (i) the improved liposomal vaccine with encapsulated T-cell peptide T48 (containing T-cell epitopes PADRE, T2, T30 and T17 separated with the GS linker) and a TLR4 agonist as adjuvant (MPLA) (Liposome M), (ii) the improved liposomal vaccine with encapsulated T52 (containing T-cell epitopes PADRE, T2 and T30 separated with the RK linker) and a TLR4 agonist (MPLA) as adjuvant (Liposome N) or (iii) PBS. Spleens from mice were harvested 42 days after the first immunization for the analysis of T-cell responses by IL-4 and IFN-γ ELISPOT. Single cell suspensions were incubated with medium, T48 or T52 peptide at 10 ug/mL for 48 hours. Plates were incubated with a biotinylated anti-mouse IL-4 or IFN-γ monoclonal antibodies and with streptavidin alkaline phosphatase (AP). Spots were developed by adding the AP substrate. FIG. 11 shows that the restimulation of mouse splenocytes with the same peptide as the one encapsulated in the liposome induced IL-4 (FIG. 11B) and IFN-γ spot forming cells (FIG. 11A), while the splenocytes of PBS-injected mice did not. This confirmed that the addition of T-cell epitope to the vaccine induced the activation of specific T-cells, allowing them to further provide the help in antibody production to the tau-specific B-cells.

Figure 12:
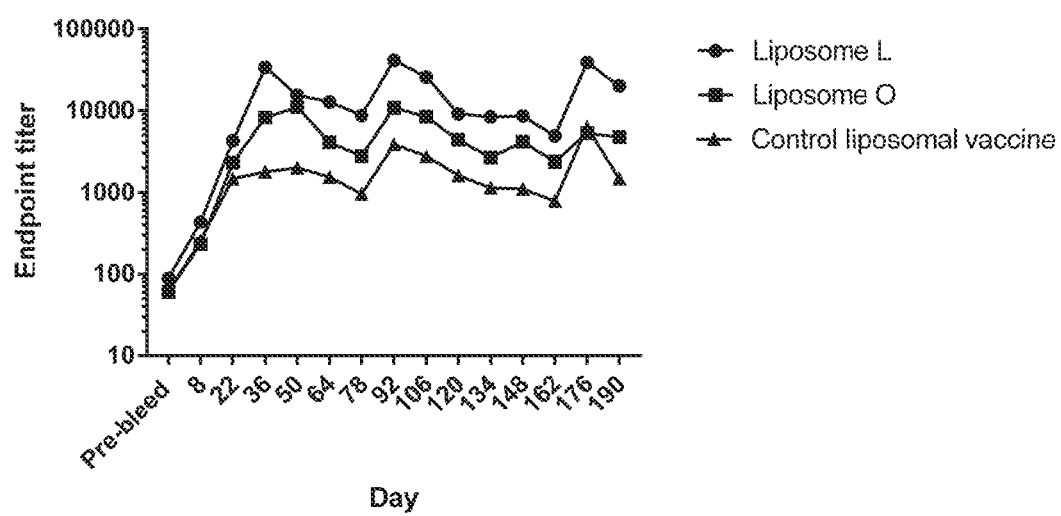
FIG. 12 shows that liposomal vaccine containing an encapsulated T-cell epitope (Liposome L) and liposomal vaccine containing an anchored T-cell epitope (Liposome O) each induced higher tau phosphopeptide-specific antibody titers than the control liposomal vaccine without T-cell epitope; each of Liposome L, Liposome O and control liposome further contains MPLA as adjuvant.

Example 10: Liposomal Vaccines Containing Encapsulated T-cell Epitope and Anchored T-Cell Epitope Groups of Rhesus macaques (n=6 per group) were immunized subcutaneously at days 1, 29, 85 and 169 with (i) liposomal vaccine containing encapsulated T-cell epitope T50 and TLR4 ligand (MPLA) as adjuvant (liposome L), (ii) liposomal vaccine containing anchored T-cell epitope T46 and TLR4 ligand (MPLA) as adjuvant (liposome O) and (iii) control liposomal vaccine containing a TLR4 ligand (MPLA) as adjuvant and no T-cell epitope. Bleedings were performed before immunization (at day −14) and at days 8, 22, 36, 50, 64, 78, 92, 106, 120, 134, 148, 162, 176 and 190, and the sera were isolated. Specific IgG antibody titers were determined by ELISA, using phosphorylated tau peptide of SEQ ID NO: 2 as the coating antigen and an anti-monkey IgG secondary antibody. Resulting antibody levels were calculated as end-point titers (last serum dilution inducing a positive response), and the data was expressed as geometric mean per group. As shown in FIG. 12, liposomal vaccine containing an encapsulated T-cell epitope (Liposome L) and liposomal vaccine containing an anchored T-cell epitope (Liposome 0) each induced higher tau phosphopeptide-specific antibody titers than the control liposomal vaccine without T-cell epitope.

Example 11: Antibody Response in Mice Induced by Conjugate Vaccine

Figure 13A:
FIG. 13A illustrates that groups of adult female Balb/C mice (n=14 per group) were immunized a total of four times with 100 ug adjuvanted KLH-tau conjugate vaccine (KLH-TAUVAC-p7.1 or KLH-TAUVAC-p22.1), an active placebo vaccine (KLH plus alum or Ribi), or an inactive placebo (PBS) according to the schedule shown: four animals from each immunization group were sacrificed seven days after the primary immunization, and the lymph nodes draining the injection site were collected.

Female BALB/c mice (14 mice per group) were immunized with Conjugate B or Conjugate C (containing SEQ ID NO:1 or SEQ ID NO: 3 covalently linked to KLH) following the schedule depicted in FIG. 13A and using the vaccine candidates adjuvanted with either a potent multicomponent adjuvant (Sigma Adjuvant System®, Sigma-Aldrich, from here on referred to as Ribi) or a single component depot adjuvant (Alhydrogel® adjuvant 2% or aluminum hydroxide gel, InvivoGen, from here on referred to as alum). The amino acid sequence of SEQ ID NO:1 contains only one amino acid difference compared to that in the mouse protein, while the sequence of SEQ ID NO:3 is 100% conserved between humans and mice. Thus, the selected epitopes can be reasonably considered "self" proteins for mice and mice should be a relevant model to investigate the limitations that immune tolerance might place on immunogenicity.

Figure 13B:
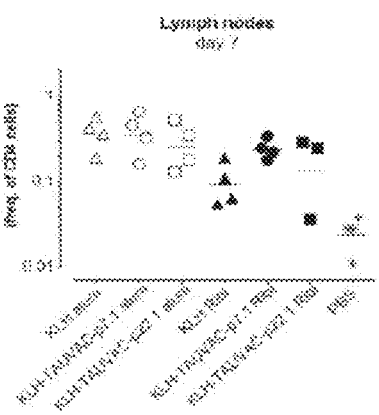
FIG. 13B shows the geometric mean percent of TfHs by immunization group (n=4 mice per group analyzed individually) in the draining nodes: all groups receiving active vaccines or placebos had measurable TfHs; moreover, animals receiving vaccine KLH-TAUVAC-p7.1, KLH-TAUVAC-p22.1 or active placebo KLH plus alum, had significantly more TfHs than the animals given an inactive placebo (p=0.0044 for KLH-TAUVAC-p7.1; p=0.0482 for KLH-TAUVAC-p22.1; p=0.0063 for KLH, using an ANOVA test followed by a Dunnett's adjustment for multiple comparisons)

As a first measure of vaccine immunogenicity flow cytometry was used to measure induction of T follicular helper cells (TfHs) in the cervical lymph nodes draining the vaccine injection site (four mice per group). TfHs are a specialized population of $CD4^+$ T cells characterized by the expression of CXCR5, PD-1 and ICOS among other molecules. TfHs expand after exposure to a vaccine or other immune stimuli and support affinity maturation of B cells in the germinal center (Crotty, 2011, Annual Reviews of Immunology. Vol 29:p621-663). The number of TfHs induced correlates positively with the protective efficacy of vaccines in humans (Bentebibel et al., 2013, Sci Transl Med., 5(176): 176ra32; Spensieri et al., 2013, Proc Natl Acad Sci USA., 110(35):14330-5) and small animals. As shown in FIG. 13B, both vaccines, as well as the KLH plus adjuvant control immunization induced measurable TfHs in vaccinated mice. Moreover, all the animals receiving active vaccine (Conjugate B and Conjugate C groups) or active placebo (KLH) plus alum, had significantly more TfHs than the animals given an inactive placebo (PBS group), when draining cervical lymph nodes were harvested seven days after the first immunization (P=0.0044 for KLH-TAUVAC-p7.1; P=0.0482 for KLH-TAUVAC-p22.1; P=0.0063 for KLH, using an ANOVA test followed by Dunnett's adjustment for multiple comparisons).

Figure 13C:
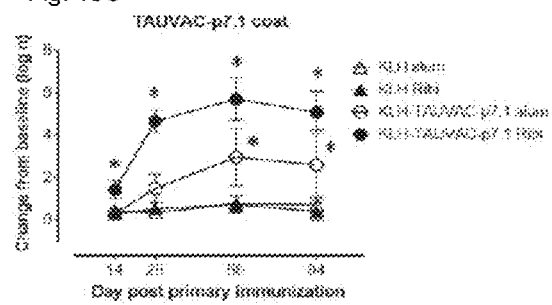
FIGS. 13C-H show change in serum titers from baseline (day 0) at four timepoints after immunization (days 14, 28, 56, and 84) for the group means (n=5-10) with 95% confidence interval: asterisk indicates time points at which KLH-TAUVAC-induced antibody response is significantly higher than the one induced by active placebos (p≤0.05, measured using ANOVA test followed by Tukey's adjustment for multiple comparisons), more specifically.

ELISA was conducted to determine the serum titer of antibodies binding to the tau phosphopeptides and to KLH at Day 0 and at four additional time points after immunization (days 14, 28, 56, and 84, see FIG. 13C, D, G and H). As shown in FIG. 13C, immunization with Conjugate B induced binding antibodies reactive against the corresponding vaccine peptide. For animals immunized with Conjugate B and Ribi adjuvant, binding titers against the vaccine peptide were significantly higher than the binding titers induced by the active placebo (compare Conjugate B plus Ribi to KLH plus Ribi) at all time points measured (P<0.001 using an ANOVA test followed by Tukey's adjustment for multiple comparisons). For the alum adjuvanted group the difference was significant only at days 56 and 84 (P=0.001 and 0.012 respectively).

Figure 13D:
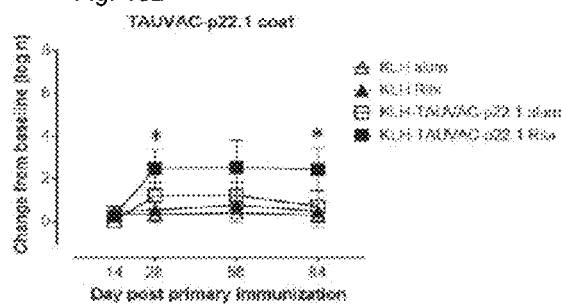

The tau specific antibody response to Conjugate C (FIG. 13D) was of overall lower magnitude than was the response to Conjugate B, although the assay differences (different coating peptide) preclude making a direct statistical comparison between the two vaccines. Nonetheless, antibody titers against Conjugate C were significantly higher in mice vaccinated with Conjugate C plus Ribi than in mice receiving active placebo KLH Ribi at days 28 and 84 (P=0.001 and 0.008 respectively) after immunization; titers of the alum adjuvanted group were not significantly different than those of the active placebo.

Figure 13E:
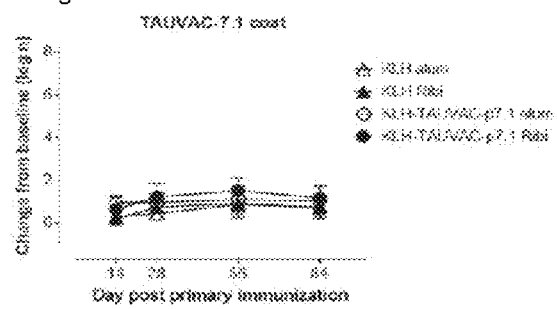
Figure 13F:
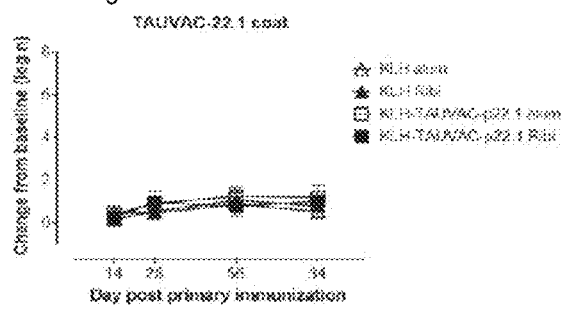
Figure 13G:
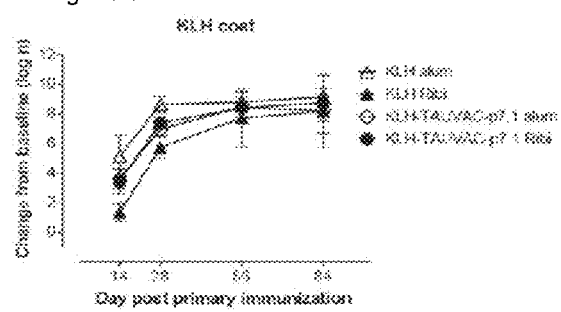
Figure 13H:
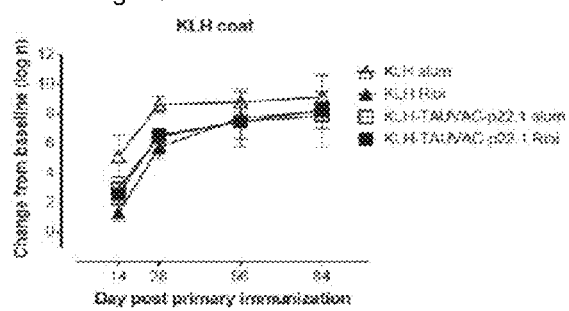

Although the carrier protein protects the phosphopeptide from degradation in vivo to some extent, it was likely that phosphatase digestion of the peptide antigens in vivo would expose some non-phosphorylated peptide to the immune system. To determine whether that exposure resulted in generation of antibodies capable of binding non-phosphorylated peptide in Conjugate B and Conjugate C, ELISA was performed using non-phosphorylated peptides as the coating antigen. As shown in FIG. 13E-F, the response to non-phosphorylated tau peptides was low, comparable to the response of the active placebos to the same non-phosphorylated peptide. Moreover, in animals immunized with Conjugate B and Ribi, binding titers against the phosphorylated peptide were significantly higher than the binding titers against the non-phosphorylated peptide at all timepoints measured (P=0.009 at day 14; P<0.0001 at day 28, 56 and 84 using an ANOVA test). For the alum adjuvanted group the difference was significant only at days 56 and 84 (P=0.0002 and 0.001 respectively). For animals immunized with Conjugate C, responses to the phosphorylated peptide were higher only when Ribi adjuvant was used (P<0.0001 at day 28; P=0.0001 at day 56 and 84).

Figure 14:
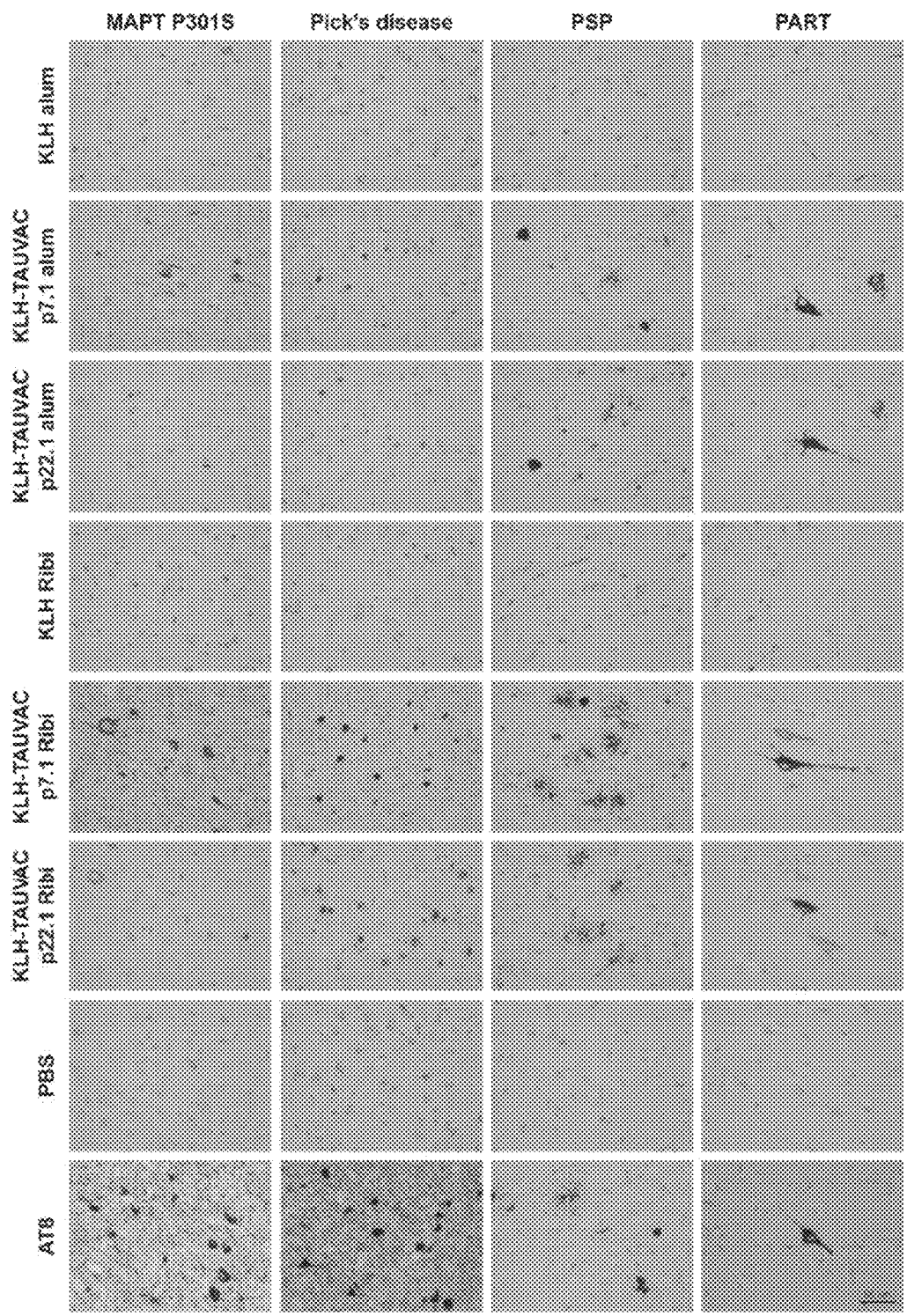
FIG. 14 shows that sera from mice immunized with Tau conjugate also bound pathological tau structures from other tauopathies: pooled sera (n=6) from each vaccination group 84 days after primary immunization were used to stain brain tissue from a frontal temporal dementia case with a MAPT mutation (MAPT P301S, frontal cortex), a case with Pick's disease (frontal cortex), progressive supranuclear palsy (PSP, caudate nucleus) and primary age-related tauopathy (PART, hippocampus); sera from animals receiving the active vaccines highlighted the tau-related structures typical of each tauopathy, while sera from animals immunized with an active placebo (KLH-alum or KLH-Ribi) or the inactive one (PBS), did not stain any of those structures; as reference an immunostaining with AT8 of the corresponding area is shown; scale bar=50 um.

Example 12: Antibodies Induced by Conjugate Vaccines Bind to Physiologically Relevant Forms of Altered Tau To further determine whether the vaccine induced antibodies could bind to physiologically relevant forms of altered tau, we used post-immune sera from vaccinated mice to stain post-mortem human brain sections collected either from Alzheimer's disease patients (5 AD cases), from patients affected by other tauopathies (3 cases of PART, FTD, PICK and PSP), or from age-matched healthy controls (5 control cases, CTRL). As expected, sera from control animals (PBS and active placebo groups) did not bind the brain sections, while AT8, a monoclonal antibody that binds to pTau [pSer202, pThr 205] obtained from a murine clone, showed strong immunoreactivity of tau pathology in an adjacent tissue section of the corresponding area (FIG. 14). Sera from animals immunized with the active vaccines Conjugate B and Conjugate C bound pathological tau structures not only in the AD sections (data not shown), but also in those from other tauopathies (FIG. 14). Conjugate B induced antibodies reacted with (pre-)tangles, neuropil threads and neuritic plaques in AD cases. These post-immune sera were also able to immunoreact with neurofibril tangles and neuropil threads in PART brain tissue, neuronal inclusions and neuropil threads in FTD-tau (MAPT P301S)

tissue, inclusions and astrocytes in some of the Pick's disease cases and finally the neuronal inclusions, neuropil threads and astrocytes typical of PSP. Conjugate C induced polyclonal sera also reacted to pathological tau structures characteristics of each tauopathy. In the AD cases, the staining was mainly focused on neurofibrillary tangles, and to less extent on neuritic plaques and neuropil threads. Lower magnification of the corresponding areas showed similar results (Data not known).

Example 13: Vaccine-Induced Antibodies are Functional in Mice

The protective efficacy of Conjugate B vaccine was tested in an injection model of tauopathy (Peeraer et al., 2015, Neurobiol Dis., 73:83-95). In this model, mice made susceptible to tauopathy via a genetic mutation (P301L) receive an intracerebral injection of enriched PHF isolated from human AD brain following the timelines indicated in FIG. 15A. The injection, which is performed before the onset of transgene-induced tauopathy, accelerates the development of tauopathy in these animals. Conversely, when the ePHF "seed" is pre-mixed with an antibody capable of suppressing tau seeding activity like AT8, the induction of tauopathy is reduced (unpublished data, not shown).

Figure 15A:
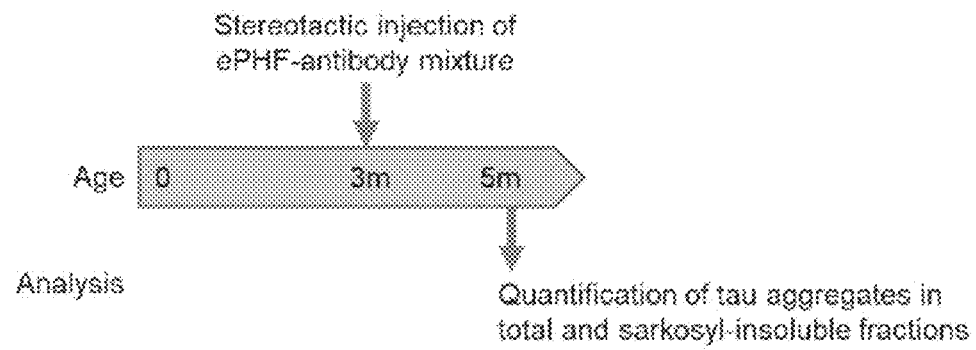
FIG. 15A: three month old P301L transgenic mice (n=15 per group) received a stereotactic injection of human ePHF pre-incubated with purified IgG from mice immunized with either KLH-TAUVAC-p7.1 plus RIBI or with the active placebo KLH plus RIBI; two months after the injection, all mice were sacrificed and the amount of aggregated tau in the mice was determined in total and sarkosyl-insoluble fractions.
Figure 15B:
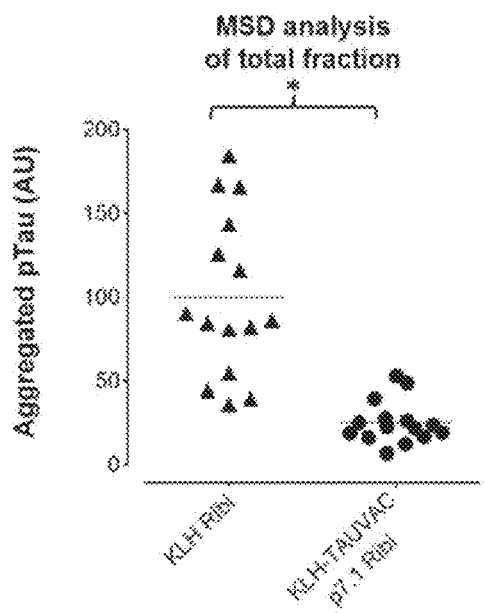
FIGS. 15B and 15C: the total fractions (B) and sarkosyl-insoluble fractions (C) collected from the injected hemisphere of each animal: graphs show the amount of tau measured by MSD; in both the total fraction and the insoluble fraction, brains of mice receiving ePHF pre-incubated with IgG from KLH-TAUVAC-p7.1 immunized mice had significantly less aggregated tau than did mice receiving ePHF pre-incubated with control antibodies.
Figure 15C:
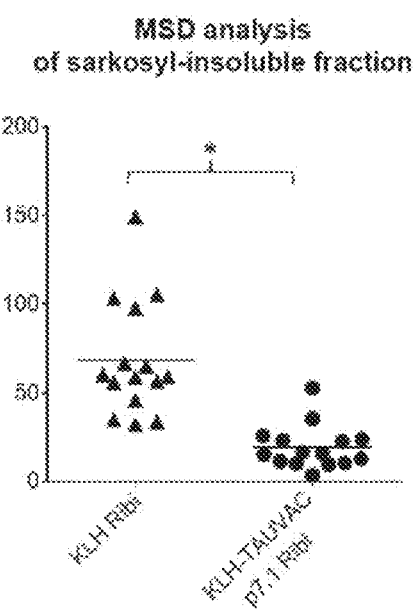

Following the scheme in FIG. 15A, we assessed the development of tauopathy after stereotaxic injection of enriched human PHF pre-mixed with IgG purified from serum of animals immunized with Conjugate B, Ribi or with the active control KLH Ribi. Two months after the injection, the brains of these mice were harvested and the amount of aggregated tau in total and sarkosyl-insoluble fractions was determined using standard biochemical analysis. Data obtained showed that when mice were injected with ePHF that had been pre-mixed with IgG from mice vaccinated with Conjugate B, there was significantly less aggregated phospho-tau in both total (FIG. 15B) and sarkosyl-insoluble (FIG. 15C) fractions compared to animals receiving the control injection (p<0.0001 KLH Ribi vs KLH-TAUVAC-p7.1 Ribi using an ANOVA test followed by Holm-Bonferroni adjustment for multiple comparisons). The sarkosyl-insoluble tau being well accepted to correlate with the pathological features of tauopathy, this result demonstrates that antibodies induced by vaccination with KLH-TAU-VAC-p7.1 are protective in vivo.

Example 14: Vaccine-Induced Antibodies are Functional in Non-Human Primates

Figure 16A:
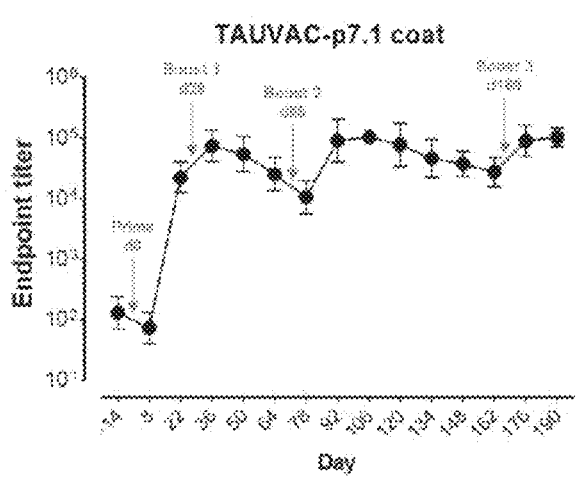
FIG. 16A: sera from animals immunized with KLH-TAUVAC-p7.1 were tested for reactivity on the immunizing peptide p7.1 using ELISA.
Figure 16B:
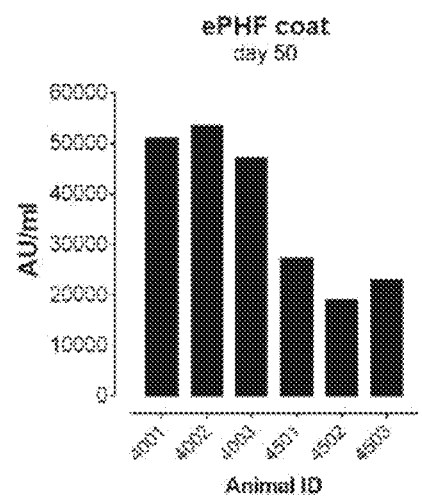
FIG. 16B: sera collected from all animals 50 days following primary immunization had measurable antibody levels against human ePHF using MSD, with 3 out of 6 animals showing high reactivity on this antigen.
Figure 16C:
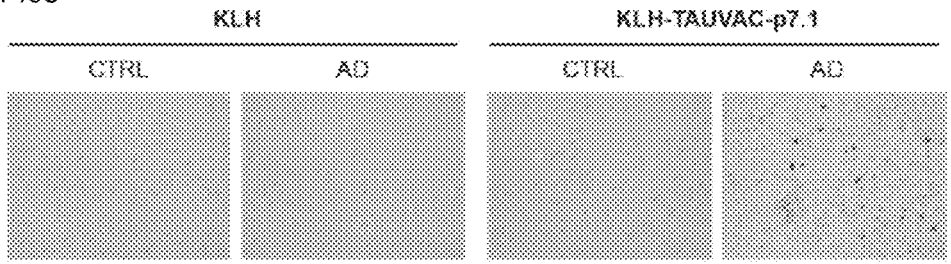
FIG. 16C: sera collected from animals 50 days following primary immunization were applied to human brain sections from healthy individuals or from AD patients, post-immune sera from KLH-TAUVAC-p7.1 group stained pathological tau structures, namely neurofibrillary tangles, neuropil threads and neuritic plaques in AD brain tissue, while sera from KLH-immunized mice did not show any reactivity, and no staining was observed on control tissue.
Figure 16D:
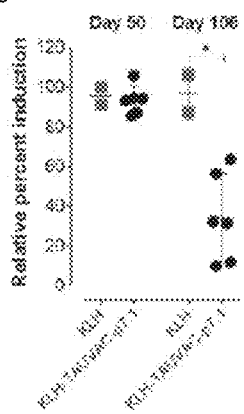
FIG. 16D: when tested in the tau immunodepletion assay, animals receiving KLH-TAUVAC-p7.1 had antibodies able to bind and deplete tau seed (p=0.03 at day 50 using an ANOVA test followed by Dunnett's adjustment for multiple comparisons), while immunization with KLH did not trigger such antibodies.
Figure 16E:
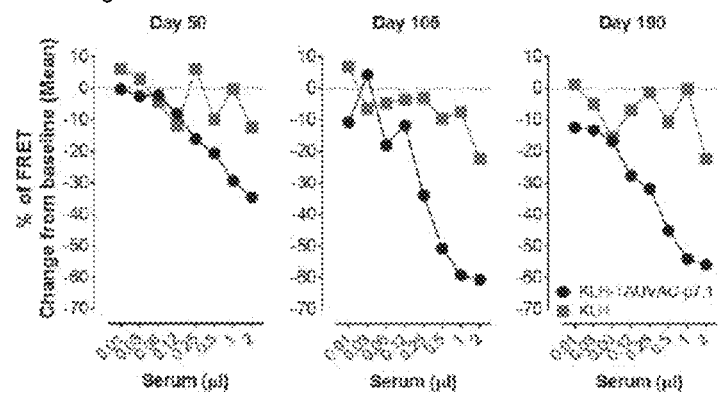
FIG. 16E: pre- and post-immunization sera were also tested in the neutralization assay as serially diluted individual samples; changes from baseline (CFB) were calculated as difference between FRET counts for readings at day −14 prior to vaccination (baseline) and post vaccination days 50, 106 and 190 respectively. Response at a specific post vaccination day ($day_i$) was then computed as follows: Response=% FRET_$day_i$−% FRET_baseline; a general linear mixed model on aforementioned responses, with animal as random effect, was applied with variables vaccine groups, day and serum levels treated as categorical variables and all their interactions.

Rhesus macaques were immunized with alum and CpG oligonucleotide adjuvated Conjugate B (n=6) or with KLH (n=2) at day 1, 29, 85 and 169. Blood was collected every 14 days and sera from animals immunized with Conjugate B tested for reactivity on the immunizing peptide using ELISA (FIG. 16 A) and human ePHF using MSD (FIG. 16B). Immunization with Conjugate B resulted in a sustained and consistent antibody response against the vaccine phosphopeptide. Moreover, all animals had measurable antibody levels against human ePHF with 3 out of 6 animals showing high reactivity on this antigen. Sera collected from animals 50 days following primary immunization were applied to human brain sections from healthy individuals or from AD patients (FIG. 16C). Post-immune sera from Conjugate B group stained pathological tau structures, namely neurofibrillary tangles, neuropil threads and neuritic plaques in AD brain tissue, while sera from KLH-immunized mice did not show any reactivity. No staining was observed on control tissue. When tested in the tau immunodepletion assay, animals receiving Conjugate B had antibodies able to bind and deplete tau seed (p=0.03 at day 50 using an ANOVA test followed by Dunnett's adjustment for multiple comparisons), while immunization with KLH did not trigger such antibodies (FIG. 16D). Pre- and post-immunization sera were also tested in the neutralization assay as serially diluted individual samples (FIG. 16E). Changes from baseline (CFB) were calculated as difference between FRET counts for readings at day −14 prior to vaccination (baseline) and post vaccination days 50, 106 and 190 respectively. Response at a specific post vaccination day (day) was then computed as follows:

Response=% FRET_day$_i$−% FRET_baseline

A general linear mixed model on aforementioned responses, with animal as random effect, was applied with variables vaccine groups, day and serum levels treated as categorical variables and all their interactions. Given the exploratory nature of the study, no multiple testing adjustment was considered. Hypothesis testing was performed at the 5% level of significance.

Figure 17A:
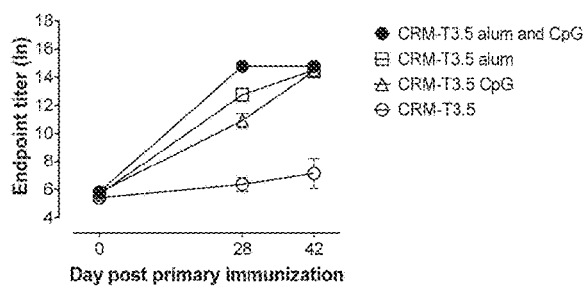
FIG. 17A: mice were immunized with 2 ug of the Conjugate A vaccine.
Figure 17B:
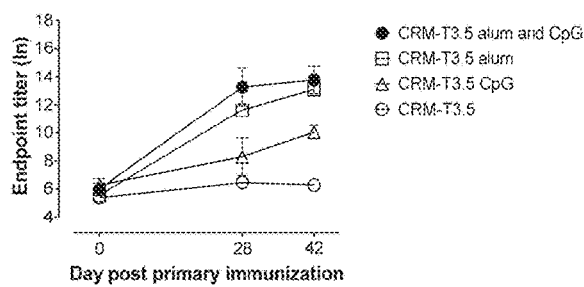
FIG. 17B: mice were immunized with 0.2 ug of the Conjugate A vaccine.
Figure 18:
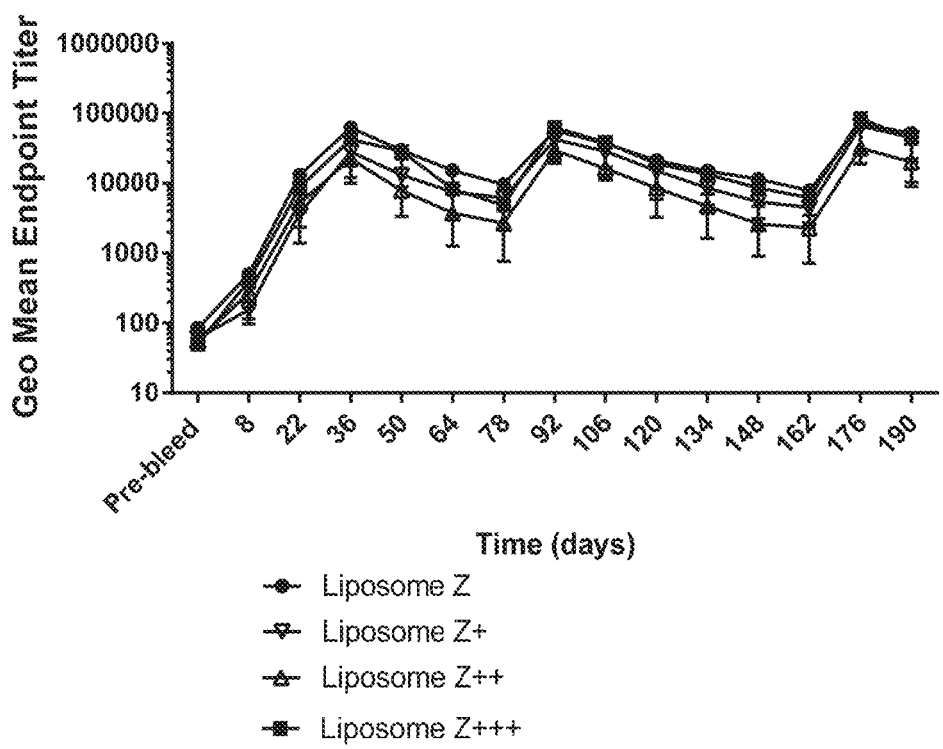
FIG. 18 shows that tau vaccines according to embodiments of the invention with different ratios of Tau peptide to T-cell epitope induce sustained high titer anti-phosphorylated tau antibodies in Rhesus macaques.

Example 15: Mice Immunized with the Conjugate Vaccine in Combination of Alum and CpG Oligonucleotide Adjuvants Resulted in Higher Titer Antibody Responses to the Vaccine Peptide Adult female C57BL/6 mice (n=5-6 per group) were immunized intramuscularly with either 2 ug (FIG. 17A) or 0.2 ug (FIG. 17B) of the Conjugate A vaccine. The conjugate vaccine was either administered alone (no adjuvant), with alum hydroxide, with CpG oligonucleotide, or with alum and CpG oligonucleotide combined. All mice received a primary immunization on day 0 of the study followed by a single booster immunization on day 28. The dose for the alum adjuvant was 500 ug per mouse per injection, and the dose for the CpG oligonucleotide adjuvant was 20 ug/mouse per injection. The graphs in FIG. 17 show the results of binding ELISA using serum collected from mice before immunization (day 0) and at two time points after immunization (day 28 and 42) with vaccine peptide T3.5 as the coating antigen. T3.5 specific mean endpoint titers per group were plotted, with error bars representing standard error. The tables show the statistical analysis of the results, in which antibody titers were compared using the non-parametric Kruskal-Wallis Test, and pairwise group comparisons were assessed using the Wilcoxon Signed Rank test as post-hoc to the Kruskal Wallis test.

The results shown in FIG. 17 illustrate that at both doses, the non-adjuvanted vaccine failed to induce a strong immune response. Use of alum or CpG oligonucleotide or a combination of both improved the magnitude of the antibody response (p≤0.0152). Moreover, for animals immunized with 2 ug of vaccine, the adjuvant combination gave significantly higher antibody titers than single adjuvants at day 28 (p=0.0028). The combination alum-CpG oligonucleotide also performed better than CpG oligonucleotide alone for animals immunized with 0.2 ug of vaccine at day 42 (p=0.0497). These data support the use of the alum and CpG oligonucleotide adjuvant combination.

Example 16: Liposomal Vaccines with Different Ratios Tau Peptide: T-Cell Epitopes Induce High and Sustained Level of Tau Phosphopeptide-Specific IgG Antibody Titers Adult Rhesus macaques (n=6 per group) were immunized subcutaneously at days 1, 29, 85 and 169 with 1800 µg of acetate tetrapalmitoylated phosphorylated tau peptide of SEQ ID NO: 2 per dose in the improved liposomal vaccine with encapsulated T50 T-cell epitope, containing both 3D-(6-acyl) PHAD® and lipidated CpG 2006 oligonucleotide adjuvant with: i) 400 ug/mL of phosphorylated tau peptide of SEQ ID NO: 2 and 100 ug/mL of T50 (Liposome Z), ii) 1200 ug/mL of phosphorylated tau peptide of SEQ ID NO: 2 and 1200 ug/mL of T50 (Liposome $Z^{+}$), iii) 400 ug/mL of phosphorylated tau peptide of SEQ ID NO: 2 and 400 ug/mL of T50 (Liposome $Z^{++}$), iv) 1200 ug/mL of phosphorylated tau peptide of SEQ ID NO: 2 and 300 ug/mL of T50 (Liposome $Z^{+++}$). Bleedings were performed before immunization and at days 8, 22, 36, 50, 64, 78, 92, 106, 120, 134, 148, 162, 176 and 190 and the sera were isolated. Specific IgG antibody titers in the sera were determined by ELISA, using phosphorylated tau peptide of SEQ ID NO: 2 as the coating antigen and an anti-monkey IgG secondary antibody. Resulting antibody levels were calculated as end-point titers (last serum dilution inducing a positive response) for each individual monkey over time. Geometric mean of end-point titers per group ±95% confidence interval is presented in FIG. 18, showing that all four tested liposomal vaccines induced high and sustained titers against the tau phospho-peptide.

SEQUENCE LISTING phospho-tau peptide (7.1)
SEQ ID NO: 1
GDRSGYS[pS]PG[pS]PG[pT]PGSRSRT phospho-tau peptide (T3.5)
SEQ ID NO: 2
VYK[pS]PVVSGDT[pS]PRHL phospho-tau peptide (22.1)
SEQ ID NO: 3
SSTGSIDMVD[pS]PQLA[pT]LA tau peptide
SEQ ID NO: 4
VYKSPVVSGDTSPRHL phospho-tau peptide
SEQ ID NO: 5
RENAKAKTDHGAEIVYK[pS]PVVSGDT[pS]PRHL phospho-tau peptide
SEQ ID NO: 6
RQEFEVMEDHAGT[pY]GL phospho-tau peptide
SEQ ID NO: 7
PGSRSR[pT]P[pS]LPTPPTR phospho-tau peptide
SEQ ID NO: 8
GYSSPG[pS]PG[pT]PGSRSR phospho-tau peptide
SEQ ID NO: 9
GDT[pS]PRHL[pS]NVSSTGSID phospho-tau peptide
SEQ ID NO: 10
PG[pS]PG[pT]PGSRSR[pT]P[pS]LP phospho-tau peptide
SEQ ID NO: 11
HL[pS]NVSSTGSID phospho-tau peptide
SEQ ID NO: 12
VSGDT[pS]PRHL T50 T cell epitope -continued

SEQ ID NO: 13
AKFVAAWTLKAAAVVRQYIKANSKFIGITELVVRFNNFTVSFWLRVPKVS
ASHLE-$NH_2$

T46 T cell epitope
SEQ ID NO: 14
AKFVAAWTLKAAAGSQYIKANSKFIGITELGSFNNFTVSFWLRVPKVSAS
HLEK(Pal)K(Pal)-$NH_2$ T48 helper T cell epitope
SEQ ID NO: 15
AKFVAAWTLKAAAGSQYIKANSKFIGITELGSFNNFTVSFWLRVPKVSAS
HLEGSLINSTKIYSYFPSVISKVNQ-$NH_2$ T51 helper T cell epitope
SEQ ID NO: 16
AKFVAAWTLKAAARRQYIKANSKFIGITELRRFNNFTVSFWLRVPKVSAS
HLE-$NH_2$ T52 helper T cell epitope
SEQ ID NO: 17
AKFVAAWTLKAAARKQYIKANSKFIGITELRKFNNFTVSFWLRVPKVSAS
HLE-$NH_2$ CpG 2006 (also known as CpG 7909)
SEQ ID NO: 18
5′-tcgtcgttttgtcgttttgtcgtt-3′
wherein lower case means phosphorothioate (ps) internucleotide linkages CpG 1018
SEQ ID NO: 19
5′-tgactgtgaacgttcgagatga-3′
wherein lower case means phosphorothioate internucleotide linkages CpG2395
SEQ ID NO: 20
5′-tcgtcgttttcggcgcgcgccg-3′
wherein lower case means phosphorothioate internucleotide linkages CpG2216
SEQ ID NO: 21
5'-ggGGGACGATCGTCgggggg-3'
wherein lower case means phosphorothioate internucleotide linkages and capital letters means phosphodiester (po) linkages CpG2336
SEQ ID NO: 22
5'-gggGACGACGTCGTGgggggg-3',
wherein lower case means phosphorothioate internucleotide linkages and capital letters means phosphodiester linkages Pan DR epitope (PADRE) peptide
SEQ ID NO: 23
AKFVAAWTLKAAA

P2
SEQ ID NO: 24
QYIKANSKFIGITEL

P30
SEQ ID NO: 25
FNNFTVSFWLRVPKVSASHLE $TT_{586-605}$
SEQ ID NO: 26
LINSTKIYSYFPSVISKVNQ palmitoylated phospho-tau peptide (palmitoylated 7.1)

-continued palmitoylated phospho-tau peptide
SEQ ID NO: 27
K(pal)K(pal)GDRSGYS[pS]PG[pS]PG[pT]PGSRSRTK(pal)K
(pal)

palmitoylated phospho-tau peptide
(T3, palmitoylated T3.5)
SEQ ID NO: 28
K(pal)K(pal)VYK[pS]PVVSGDT[pS]PRHLK(pal)K(pal)

palmitoylated phospho-tau peptide
(palmitoylated 22.1)
SEQ ID NO: 29
K(pal)K(pal)SSTGSIDMVD[pS]PQLA[pT]LAK(pal)K(pal)

palmitoylated tau peptide
SEQ ID NO: 30
K(pal)K(pal)VYKSPVVSGDTSPRHLK(pal)K(pal)

palmitoylated phospho-tau peptide
SEQ ID NO: 31
K(pal)K(pal)RENAKAKTDHGAEIVYK[pS]PVVSGDT[pS]PRHLK
(pal)K(pal)

palmitoylated phospho-tau peptide
SEQ ID NO: 32
K(pal)K(pal)RQEFEVMEDHAGT[pY]GLK(pal)K(pal)

palmitoylated phospho-tau peptide
SEQ ID NO: 33
K(pal)K(pal)PGSRSR[pT]P[pS]LPTPPTRK(pal)K(pal)

palmitoylated phospho-tau peptide
SEQ ID NO: 34
K(pal)K(pal)GYSSPG[pS]PG[pT]PGSRSRK(pal)K(pal)

palmitoylated phospho-tau peptide
SEQ ID NO: 35
K(pal)K(pal)GDT[pS]PRHL[pS]NVSSTGSIDK(pal)K(pal)

palmitoylated phospho-tau peptide
SEQ ID NO: 36
K(pal)K(pal)PG[pS]PG[pT]PGSRSR[pT]P[pS]LPK(pal)K
(pal)

palmitoylated phospho-tau peptide
SEQ ID NO: 37
K(pal)K(pal)HL[pS]NVSSTGSIDK(pal)K(pal)

palmitoylated phospho-tau peptide
SEQ ID NO: 38
K(pal)K(pal)VSGDT[pS]PRHLK(pal)K(pal)

T50 without the C-terminal amide
SEQ ID NO: 39
AKFVAAWTLKAAAVVRQYIKANSKFIGITELVVRFNNFTVSFWLRVPKVS
ASHLE T46 without the -Lys(Pal)-Lys(Pal)-NH₂ at the
C-terminal
SEQ ID NO: 40
AKFVAAWTLKAAAGSQYIKANSKFIGITELGSFNNFTVSFWLRVPKVSAS
HLE T48 without the C-terminal amide
SEQ ID NO: 41
AKFVAAWTLKAAAGSQYIKANSKFIGITELGSFNNFTVSFWLRVPKVSAS
HLEGSLINSTKIYSYFPSVISKVNQ T51 without the C-terminal amide
SEQ ID NO: 42
AKFVAAWTLKAAARRQYIKANSKFIGITELRRFNNFTVSFWLRVPKVSAS
HLE T52 without the C-terminal amide
SEQ ID NO: 43
AKFVAAWTLKAAARKQYIKANSKFIGITELRKFNNFTVSFWLRVPKVSAS
HLE T57
SEQ ID NO: 44
AKFVAAWTLKAAAVVRQYIKANSKFIGITELVVRFNNFTVSFWLRVPKVS
ASHLE-K(Pal)K(Pal)-NH2

REFERENCES

Asuni A A et al., J Neurosci. 2007 Aug. 22; 27(34):9115-29
Bentebibel et al., 2013, Sci Transl Med., 5(176):176ra32
Crotty, 2011, Annual Reviews of Immunology. Vol 29:p621-663
Friedhoff et al., Biochimica et Biophysica Acta 1502 (2000) 122-132
Greenberg and Davies, 1991, Proc Natl Acad Sci USA, 87(15):5827-31
Hanger et al., Trends Mol Med. 15:112-9, 2009
Hickman et al., J. Biol. Chem. vol. 286, NO. 16, pp. 13966-13976, Apr. 22, 2011
Kontsekova E et al., Alzheimers Res Ther. 2014 Aug. 1; 6(4):44
Novak P et al., Lancet Neurology 2017, 16:123-134
Peeraer et al., 2015, Neurobiol Dis., 73:83-95
Ries et al., 2015, Org. Biomol. Chem., 13:9673
Spensieri et al., 2013, Proc Natl Acad Sci USA., 110(35): 14330-5
Theunis C et al., PLoS One. 2013; 8(8): e72301
U.S. Pat. No. 7,741,297
U.S. Pat. No. 8,647,631
U.S. Pat. No. 9,687,447
WO90/14837
WO2010/115843

---

It is claimed:

1. A liposome, comprising:
   a. a tau peptide having an amino acid sequence selected from the group consisting of SEQ ID NOs: 2, 5, 9, and 12, wherein the tau peptide is presented on the surface of the liposome;
   b. a helper T cell epitope comprising at least one amino acid sequence selected from the group consisting of: SEQ ID NOs:23, 24, 25, and 26;
   c. a lipidated CpG oligonucleotide, wherein the CpG oligonucleotide comprises one or more phosphorothioate internucleotide linkages, and wherein the CpG oligonucleotide is covalently linked to at least one cholesterol via a linker; and
   d. monophosphoryl lipid A (MPLA).

2. The liposome of claim 1, wherein:
   a. the tau peptide has an amino acid sequence selected from the group consisting of SEQ ID NO: 28, 31, 35, and 38;
   b. the lipidated CpG oligonucleotide has the nucleotide sequence selected from the group consisting of SEQ ID NO: 18 to SEQ ID NO:22; and
   c. the helper T cell epitope comprises the amino acid sequences of SEQ ID NO: 23, SEQ ID NO:24 and SEQ ID NO:25, wherein the amino acid sequences are covalently linked together, optionally via one or more linkers.

3. The liposome of claim 2, wherein the helper T cell epitope comprises an amino acid sequence selected from the group consisting of SEQ ID NOs:39, 40, 41, 42, and 43.

4. The liposome of claim 2, wherein the helper T cell epitope comprises an amino acid sequence selected from the group consisting of SEQ ID NOs:13, 14, 15, 16, 17, and 44.

5. The liposome of claim 1, further comprising one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

6. A liposome, comprising:
   a. a tau peptide comprising the amino acid sequence of SEQ ID NO: 2, wherein the tau peptide is presented on the surface of the liposome;
   b. a helper T cell epitope having an amino acid sequence selected from the group consisting of SEQ ID NOs:39, 40, 41, 42, and 43;
   c. a lipidated CpG oligonucleotide having the nucleotide sequence selected from the group consisting of SEQ ID NO:18 to SEQ ID NO:22, wherein the CpG oligonucleotide is covalently linked to at least one cholesterol via a linker; and
   d. monophosphoryl lipid A (MPLA).

7. The liposome of claim 6, further comprising one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

8. The liposome of claim 6, wherein the helper T cell epitope has the amino acid sequence of SEQ ID NO:39.

9. The liposome of claim 6, wherein the helper T cell epitope has the amino acid sequence of SEQ ID NO:40.

10. The liposome of claim 6, wherein the helper T cell epitope has the amino acid sequence of SEQ ID NO:41.

11. The liposome of claim 6, wherein the helper T cell epitope has the amino acid sequence of SEQ ID NO:42.

12. The liposome of claim 6, wherein the helper T cell epitope has the amino acid sequence of SEQ ID NO:43.

13. The liposome of claim 6, wherein the tau peptide has the amino acid sequence of SEQ ID NO:28.

14. A liposome, comprising:
   a. a tau peptide comprising the amino acid sequence of SEQ ID NO: 28, wherein the tau peptide is presented on the surface of the liposome;
   b. a helper T cell epitope having an amino acid sequence selected from the group consisting of SEQ ID NOs: 13, 14 or 15,
   c. a lipidated CpG oligonucleotide having the nucleotide sequence selected from the group consisting of SEQ ID NO:18, wherein the CpG oligonucleotide is covalently linked to at least one cholesterol via a linker; and
   d. monophosphoryl lipid A (MPLA).

15. The liposome of claim 14, further comprising one or more lipids selected from the group consisting of 1,2-dimyristoyl-sn-glycero-3-phosphocholine (DMPC), 1,2-dimyristoyl-sn-glycero-3-phosphoryl-3'-rac-glycerol (DMPG), and cholesterol.

16. The liposome of claim 14, wherein the helper T cell epitope has the amino acid sequence of SEQ ID NO:13.

17. The liposome of claim 14, wherein the helper T cell epitope has the amino acid sequence of SEQ ID NO:14.

18. The liposome of claim 14, wherein the helper T cell epitope has the amino acid sequence of SEQ ID NO:15.

19. A pharmaceutical composition comprising the liposome of claim 1 and a pharmaceutically acceptable carrier.

20. A pharmaceutical composition comprising the liposome of claim 6 and a pharmaceutically acceptable carrier.

21. A pharmaceutical composition comprising the liposome of claim 14 and a pharmaceutically acceptable carrier.

22. A method for inducing an immune response in a subject suffering from a neurodegenerative disorder, comprising administering to the subject the pharmaceutical composition of claim 19, wherein the neurodegenerative disease or disorder is caused by or associated with the formation of neurofibrillary lesions.

23. A method for inducing an immune response in a subject suffering from a neurodegenerative disorder, comprising administering to the subject the pharmaceutical composition of claim 20, wherein the neurodegenerative disease or disorder is caused by or associated with the formation of neurofibrillary lesions.

24. A method for inducing an immune response in a subject suffering from a neurodegenerative disorder, comprising administering to the subject the pharmaceutical composition of claim 21, wherein the neurodegenerative disease or disorder is caused by or associated with the formation of neurofibrillary lesions.

* * * * *

SEQUENCE LISTING

```
<160> NUMBER OF SEQ ID NOS: 44

<210> SEQ ID NO 1
<211> LENGTH: 21
<212> TYPE: PRT
<213> ORGANISM: Artificial Sequence
<220> FEATURE:
<223> OTHER INFORMATION: phospho-tau peptide 7.1
<220> FEATURE:
<221> NAME/KEY: phosphorylated serine
<222> LOCATION: (8)..(8)
<220> FEATURE:
```

<221> NAME/KEY: phosphorylated serine
<222> LOCATION: (11)..(11)
<220> FEATURE:
<221> NAME/KEY: phosphorylated threonine
<222> LOCATION: (14)..(14)

<400> SEQUENCE: 1

Gly Asp Arg Ser Gly Tyr Ser Ser Pro Gly Ser Pro Gly Thr Pro Gly
1               5                   10                  15

Ser Arg Ser Arg Thr
            20

<210> SEQ ID NO 2
<211> LENGTH: 16
<212> TYPE: PRT
<213> ORGANISM: Artificial Sequence
<220> FEATURE:
<223> OTHER INFORMATION: phospho-tau peptide T3.5
<220> FEATURE:
<221> NAME/KEY: phosphorylated serine
<222> LOCATION: (4)..(4)
<220> FEATURE:
<221> NAME/KEY: phosphorylated serine
<222> LOCATION: (12)..(12)

<400> SEQUENCE: 2

Val Tyr Lys Ser Pro Val Val Ser Gly Asp Thr Ser Pro Arg His Leu
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: phospho-tau peptide 22.1
<220> FEATURE:
<221> NAME/KEY: phosphorylated serine
<222> LOCATION: (11)..(11)
<220> FEATURE:
<221> NAME/KEY: phosphorylated threonine
<222> LOCATION: (16)..(16)

<400> SEQUENCE: 3

Ser Ser Thr Gly Ser Ile Asp Met Val Asp Ser Pro Gln Leu Ala Thr
1               5                   10                  15

Leu Ala

<210> SEQ ID NO 4
<211> LENGTH: 16
<212> TYPE: PRT
<213> ORGANISM: Artificial Sequence
<220> FEATURE:
<223> OTHER INFORMATION: tau peptide

<400> SEQUENCE: 4

Val Tyr Lys Ser Pro Val Val Ser Gly Asp Thr Ser Pro Arg His Leu
1               5                   10                  15

<210> SEQ ID NO 5
<211> LENGTH: 30
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (18)..(18)
<220> FEATURE:
<221> NAME/KEY: phosphorylated serine

```
<222> LOCATION: (26)..(26)

<400> SEQUENCE: 5

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30

<210> SEQ ID NO 6
<211> LENGTH: 16
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated tyrosine
<222> LOCATION: (14)..(14)

<400> SEQUENCE: 6

Arg Gln Glu Phe Glu Val Met Glu Asp His Ala Gly Thr Tyr Gly Leu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated threonine
<222> LOCATION: (7)..(7)
<220> FEATURE:
<221> NAME/KEY: phosphorylated serine
<222> LOCATION: (9)..(9)

<400> SEQUENCE: 7

Pro Gly Ser Arg Ser Arg Thr Pro Ser Leu Pro Thr Pro Pro Thr Arg
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (7)..(7)
<220> FEATURE:
<221> NAME/KEY: phosphorylated threonine
<222> LOCATION: (10)..(10)

<400> SEQUENCE: 8

Gly Tyr Ser Ser Pro Gly Ser Pro Gly Thr Pro Gly Ser Arg Ser Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (4)..(4)
<220> FEATURE:
<221> NAME/KEY: phosphorylated serine
<222> LOCATION: (9)..(9)

<400> SEQUENCE: 9
```

```
Gly Asp Thr Ser Pro Arg His Leu Ser Asn Val Ser Ser Thr Gly Ser
1               5                   10                  15

Ile Asp

<210> SEQ ID NO 10
<211> LENGTH: 17
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (3)..(3)
<220> FEATURE:
<221> NAME/KEY: phosphorylated threonine
<222> LOCATION: (6)..(6)
<220> FEATURE:
<221> NAME/KEY: phosphorylated threonine
<222> LOCATION: (13)..(13)
<220> FEATURE:
<221> NAME/KEY: phosphorylated serine
<222> LOCATION: (15)..(15)

<400> SEQUENCE: 10

Pro Gly Ser Pro Gly Thr Pro Gly Ser Arg Ser Arg Thr Pro Ser Leu
1               5                   10                  15

Pro

<210> SEQ ID NO 11
<211> LENGTH: 12
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (3)..(3)

<400> SEQUENCE: 11

His Leu Ser Asn Val Ser Ser Thr Gly Ser Ile Asp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: phospho-tau peptide
<220> FEATURE:
<221> NAME/KEY: phosphorylated serine
<222> LOCATION: (6)..(6)

<400> SEQUENCE: 12

Val Ser Gly Asp Thr Ser Pro Arg His Leu
1               5                   10

<210> SEQ ID NO 13
<211> LENGTH: 55
<212> TYPE: PRT
<213> ORGANISM: Artificial Sequence
<220> FEATURE:
<223> OTHER INFORMATION: T50 T cell epitope
<220> FEATURE:
<221> NAME/KEY: C-terminal amide
<222> LOCATION: (55)..(55)

<400> SEQUENCE: 13

Ala Lys Phe Val Ala Ala Trp Thr Leu Lys Ala Ala Ala Val Val Arg
```

```
                1               5                   10                  15
Gln Tyr Ile Lys Ala Asn Ser Lys Phe Ile Gly Ile Thr Glu Leu Val
                20                  25                  30

Val Arg Phe Asn Asn Phe Thr Val Ser Phe Trp Leu Arg Val Pro Lys
        35                  40                  45

Val Ser Ala Ser His Leu Glu
        50                  55

<210> SEQ ID NO 14
<211> LENGTH: 55
<212> TYPE: PRT
<213> ORGANISM: Artificial Sequence
<220> FEATURE:
<223> OTHER INFORMATION: T46 T cell epitope
<220> FEATURE:
<221> NAME/KEY: palmitoylated lysine
<222> LOCATION: (54)..(54)
<220> FEATURE:
<221> NAME/KEY: palmitoylated lysine
<222> LOCATION: (55)..(55)
<220> FEATURE:
<221> NAME/KEY: C-terminal amide
<222> LOCATION: (55)..(55)

<400> SEQUENCE: 14

Ala Lys Phe Val Ala Ala Trp Thr Leu Lys Ala Ala Ala Gly Ser Gln
1               5                   10                  15

Tyr Ile Lys Ala Asn Ser Lys Phe Ile Gly Ile Thr Glu Leu Gly Ser
                20                  25                  30

Phe Asn Asn Phe Thr Val Ser Phe Trp Leu Arg Val Pro Lys Val Ser
        35                  40                  45

Ala Ser His Leu Glu Lys Lys
        50                  55

<210> SEQ ID NO 15
<211> LENGTH: 75
<212> TYPE: PRT
<213> ORGANISM: Artificial Sequence
<220> FEATURE:
<223> OTHER INFORMATION: T48 helper T cell epitope
<220> FEATURE:
<221> NAME/KEY: C-terminal amide
<222> LOCATION: (75)..(75)

<400> SEQUENCE: 15

Ala Lys Phe Val Ala Ala Trp Thr Leu Lys Ala Ala Ala Gly Ser Gln
1               5                   10                  15

Tyr Ile Lys Ala Asn Ser Lys Phe Ile Gly Ile Thr Glu Leu Gly Ser
                20                  25                  30

Phe Asn Asn Phe Thr Val Ser Phe Trp Leu Arg Val Pro Lys Val Ser
        35                  40                  45

Ala Ser His Leu Glu Gly Ser Leu Ile Asn Ser Thr Lys Ile Tyr Ser
        50                  55                  60

Tyr Phe Pro Ser Val Ile Ser Lys Val Asn Gln
65                  70                  75

<210> SEQ ID NO 16
<211> LENGTH: 53
<212> TYPE: PRT
<213> ORGANISM: Artificial Sequence
<220> FEATURE:
<223> OTHER INFORMATION: T51 helper T cell epitope
<220> FEATURE:
<221> NAME/KEY: C-terminal amide
```

```
<222> LOCATION: (53)..(53)

<400> SEQUENCE: 16

Ala Lys Phe Val Ala Ala Trp Thr Leu Lys Ala Ala Arg Arg Gln
1               5                   10                  15

Tyr Ile Lys Ala Asn Ser Lys Phe Ile Gly Ile Thr Glu Leu Arg Arg
                20                  25                  30

Phe Asn Asn Phe Thr Val Ser Phe Trp Leu Arg Val Pro Lys Val Ser
            35                  40                  45

Ala Ser His Leu Glu
    50

<210> SEQ ID NO 17
<211> LENGTH: 53
<212> TYPE: PRT
<213> ORGANISM: Artificial Sequence
<220> FEATURE:
<223> OTHER INFORMATION: T52 helper T cell epitope
<220> FEATURE:
<221> NAME/KEY: C-terminal amide
<222> LOCATION: (53)..(53)

<400> SEQUENCE: 17

Ala Lys Phe Val Ala Ala Trp Thr Leu Lys Ala Ala Arg Lys Gln
1               5                   10                  15

Tyr Ile Lys Ala Asn Ser Lys Phe Ile Gly Ile Thr Glu Leu Arg Lys
                20                  25                  30

Phe Asn Asn Phe Thr Val Ser Phe Trp Leu Arg Val Pro Lys Val Ser
            35                  40                  45

Ala Ser His Leu Glu
    50

<210> SEQ ID NO 18
<211> LENGTH: 24
<212> TYPE: DNA
<213> ORGANISM: Artificial Sequence
<220> FEATURE:
<223> OTHER INFORMATION: CpG 2006
<220> FEATURE:
<221> NAME/KEY: phosphorothioate (ps) internucleotide linkages
<222> LOCATION: (1)..(24)

<400> SEQUENCE: 18
tcgtcgtttt gtcgttttgt cgtt                                          24

<210> SEQ ID NO 19
<211> LENGTH: 22
<212> TYPE: DNA
<213> ORGANISM: Artificial Sequence
<220> FEATURE:
<223> OTHER INFORMATION: CpG 1018
<220> FEATURE:
<221> NAME/KEY: phosphorothioate (ps) internucleotide linkages
<222> LOCATION: (1)..(22)

<400> SEQUENCE: 19
tgactgtgaa cgttcgagat ga                                            22

<210> SEQ ID NO 20
<211> LENGTH: 22
<212> TYPE: DNA
<213> ORGANISM: Artificial Sequence
<220> FEATURE:
<223> OTHER INFORMATION: CpG 2395
<220> FEATURE:
```

```
<221> NAME/KEY: phosphorothioate (ps) internucleotide linkages
<222> LOCATION: (1)..(22)

<400> SEQUENCE: 20
tcgtcgtttt cggcgcgcgc cg                                                   22

<210> SEQ ID NO 21
<211> LENGTH: 20
<212> TYPE: DNA
<213> ORGANISM: Artificial Sequence
<220> FEATURE:
<223> OTHER INFORMATION: CpG 2216
<220> FEATURE:
<221> NAME/KEY: phosphorothioate (ps) internucleotide linkages
<222> LOCATION: (1)..(3)
<220> FEATURE:
<221> NAME/KEY: phosphodiester (po) internucleotide linkages
<222> LOCATION: (3)..(14)
<220> FEATURE:
<221> NAME/KEY: phosphorothioate (ps) internucleotide linkages
<222> LOCATION: (14)..(20)

<400> SEQUENCE: 21 ggggggacgat cgtcgggggg                                                     20

<210> SEQ ID NO 22
<211> LENGTH: 21
<212> TYPE: DNA
<213> ORGANISM: Artificial Sequence
<220> FEATURE:
<223> OTHER INFORMATION: CpG 2336
<220> FEATURE:
<221> NAME/KEY: phosphorothioate (ps) internucleotide linkages
<222> LOCATION: (1)..(4)
<220> FEATURE:
<221> NAME/KEY: phosphodiester (po) internucleotide linkages
<222> LOCATION: (4)..(15)
<220> FEATURE:
<221> NAME/KEY: phosphorothioate (ps) internucleotide linkages
<222> LOCATION: (15)..(21)

<400> SEQUENCE: 22
ggggacgacg tcgtgggggg g                                                    21

<210> SEQ ID NO 23
<211> LENGTH: 13
<212> TYPE: PRT
<213> ORGANISM: Artificial Sequence
<220> FEATURE:
<223> OTHER INFORMATION: Pan DR epitope (PADRE) peptide

<400> SEQUENCE: 23

Ala Lys Phe Val Ala Ala Trp Thr Leu Lys Ala Ala Ala
1               5                   10

<210> SEQ ID NO 24
<211> LENGTH: 15
<212> TYPE: PRT
<213> ORGANISM: Artificial Sequence
<220> FEATURE:
<223> OTHER INFORMATION: P2

<400> SEQUENCE: 24

Gln Tyr Ile Lys Ala Asn Ser Lys Phe Ile Gly Ile Thr Glu Leu
1               5                   10                  15

<210> SEQ ID NO 25
<211> LENGTH: 21
<212> TYPE: PRT
```

```
<213> ORGANISM: Artificial Sequence
<220> FEATURE:
<223> OTHER INFORMATION: P30

<400> SEQUENCE: 25

Phe Asn Asn Phe Thr Val Ser Phe Trp Leu Arg Val Pro Lys Val Ser
1               5                   10                  15

Ala Ser His Leu Glu
            20

<210> SEQ ID NO 26
<211> LENGTH: 20
<212> TYPE: PRT
<213> ORGANISM: Artificial Sequence
<220> FEATURE:
<223> OTHER INFORMATION: TT586-605

<400> SEQUENCE: 26

Leu Ile Asn Ser Thr Lys Ile Tyr Ser Tyr Phe Pro Ser Val Ile Ser
1               5                   10                  15

Lys Val Asn Gln
            20

<210> SEQ ID NO 27
<211> LENGTH: 25
<212> TYPE: PRT
<213> ORGANISM: Artificial Sequence
<220> FEATURE:
<223> OTHER INFORMATION: palmitoylated phospho-tau peptide
      (palmitoylated 7.1)
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (10)..(10)
<220> FEATURE:
<221> NAME/KEY: phosphorylated serine
<222> LOCATION: (13)..(13)
<220> FEATURE:
<221> NAME/KEY: phosphorylated threonine
<222> LOCATION: (16)..(16)
<220> FEATURE:
<221> NAME/KEY: palmitoylated lysine
<222> LOCATION: (24)..(24)
<220> FEATURE:
<221> NAME/KEY: palmitoylated lysine
<222> LOCATION: (25)..(25)

<400> SEQUENCE: 27

Lys Lys Gly Asp Arg Ser Gly Tyr Ser Ser Pro Gly Ser Pro Gly Thr
1               5                   10                  15

Pro Gly Ser Arg Ser Arg Thr Lys Lys
            20                  25

<210> SEQ ID NO 28
<211> LENGTH: 20
<212> TYPE: PRT
<213> ORGANISM: Artificial Sequence
<220> FEATURE:
<223> OTHER INFORMATION: palmitoylated phospho-tau peptide (T3,
      palmitoylated T3.5)
<220> FEATURE:
<221> NAME/KEY: palmitoylated lysine
<222> LOCATION: (1)..(1)
<220> FEATURE:
<221> NAME/KEY: palmitoylated lysine
```

```
<222> LOCATION: (2)..(2)
<220> FEATURE:
<221> NAME/KEY: phosphorylated serine
<222> LOCATION: (6)..(6)
<220> FEATURE:
<221> NAME/KEY: phosphorylated serine
<222> LOCATION: (14)..(14)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 28

Lys Lys Val Tyr Lys Ser Pro Val Val Ser Gly Asp Thr Ser Pro Arg
1               5                   10                  15

His Leu Lys Lys
            20

<210> SEQ ID NO 29
<211> LENGTH: 22
<212> TYPE: PRT
<213> ORGANISM: Artificial Sequence
<220> FEATURE:
<223> OTHER INFORMATION: palmitoylated phospho-tau peptide
      (palmitoylated 22.1)
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (13)..(13)
<220> FEATURE:
<221> NAME/KEY: phosphorylated threonine
<222> LOCATION: (18)..(18)
<220> FEATURE:
<221> NAME/KEY: palmitoylated lysine
<222> LOCATION: (21)..(21)
<220> FEATURE:
<221> NAME/KEY: palmitoylated lysine
<222> LOCATION: (22)..(22)

<400> SEQUENCE: 29

Lys Lys Ser Ser Thr Gly Ser Ile Asp Met Val Asp Ser Pro Gln Leu
1               5                   10                  15

Ala Thr Leu Ala Lys Lys
            20

<210> SEQ ID NO 30
<211> LENGTH: 20
<212> TYPE: PRT
<213> ORGANISM: Artificial Sequence
<220> FEATURE:
<223> OTHER INFORMATION: palmitoylated tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 30
```

```
Lys Lys Val Tyr Lys Ser Pro Val Val Ser Gly Asp Thr Ser Pro Arg
1               5                   10                  15

His Leu Lys Lys
            20

<210> SEQ ID NO 31
<211> LENGTH: 34
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (20)..(20)
<220> FEATURE:
<221> NAME/KEY: phosphorylated serine
<222> LOCATION: (28)..(28)
<220> FEATURE:
<221> NAME/KEY: palmitoylated lysine
<222> LOCATION: (33)..(33)
<220> FEATURE:
<221> NAME/KEY: palmitoylated lysine
<222> LOCATION: (34)..(34)

<400> SEQUENCE: 31

Lys Lys Arg Glu Asn Ala Lys Ala Lys Thr Asp His Gly Ala Glu Ile
1               5                   10                  15

Val Tyr Lys Ser Pro Val Val Ser Gly Asp Thr Ser Pro Arg His Leu
            20                  25                  30

Lys Lys

<210> SEQ ID NO 32
<211> LENGTH: 20
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated tyrosine
<222> LOCATION: (16)..(16)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 32

Lys Lys Arg Gln Glu Phe Glu Val Met Glu Asp His Ala Gly Thr Tyr
1               5                   10                  15

Gly Leu Lys Lys
            20

<210> SEQ ID NO 33
<211> LENGTH: 20
<212> TYPE: PRT
<213> ORGANISM: Artificial Sequence
<220> FEATURE:
```

```
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated threonine
<222> LOCATION: (9)..(9)
<220> FEATURE:
<221> NAME/KEY: phosphorylated serine
<222> LOCATION: (11)..(11)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 33

Lys Lys Pro Gly Ser Arg Ser Arg Thr Pro Ser Leu Pro Thr Pro Pro
1               5                   10                  15

Thr Arg Lys Lys
            20

<210> SEQ ID NO 34
<211> LENGTH: 20
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (9)..(9)
<220> FEATURE:
<221> NAME/KEY: phosphorylated threonine
<222> LOCATION: (12)..(12)
<220> FEATURE:
<221> NAME/KEY: palmitoylated lysine
<222> LOCATION: (19)..(19)
<220> FEATURE:
<221> NAME/KEY: palmitoylated lysine
<222> LOCATION: (20)..(20)

<400> SEQUENCE: 34

Lys Lys Gly Tyr Ser Ser Pro Gly Ser Pro Gly Thr Pro Gly Ser Arg
1               5                   10                  15

Ser Arg Lys Lys
            20

<210> SEQ ID NO 35
<211> LENGTH: 22
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (6)..(6)
<220> FEATURE:
```

```
<221> NAME/KEY: phosphorylated serine
<222> LOCATION: (11)..(11)
<220> FEATURE:
<221> NAME/KEY: palmitoylated lysine
<222> LOCATION: (21)..(21)
<220> FEATURE:
<221> NAME/KEY: palmitoylated lysine
<222> LOCATION: (22)..(22)

<400> SEQUENCE: 35

Lys Lys Gly Asp Thr Ser Pro Arg His Leu Ser Asn Val Ser Ser Thr
1               5                   10                  15

Gly Ser Ile Asp Lys Lys
            20

<210> SEQ ID NO 36
<211> LENGTH: 21
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (5)..(5)
<220> FEATURE:
<221> NAME/KEY: phosphorylated threonine
<222> LOCATION: (8)..(8)
<220> FEATURE:
<221> NAME/KEY: phosphorylated threonine
<222> LOCATION: (15)..(15)
<220> FEATURE:
<221> NAME/KEY: phosphorylated serine
<222> LOCATION: (17)..(17)
<220> FEATURE:
<221> NAME/KEY: palmitoylated lysine
<222> LOCATION: (20)..(20)
<220> FEATURE:
<221> NAME/KEY: palmitoylated lysine
<222> LOCATION: (21)..(21)

<400> SEQUENCE: 36

Lys Lys Pro Gly Ser Pro Gly Thr Pro Gly Ser Arg Ser Arg Thr Pro
1               5                   10                  15

Ser Leu Pro Lys Lys
            20

<210> SEQ ID NO 37
<211> LENGTH: 16
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (5)..(5)
<220> FEATURE:
<221> NAME/KEY: palmitoylated lysine
<222> LOCATION: (15)..(15)
<220> FEATURE:
<221> NAME/KEY: palmitoylated lysine
<222> LOCATION: (16)..(16)
```

<400> SEQUENCE: 37

Lys Lys His Leu Ser Asn Val Ser Ser Thr Gly Ser Ile Asp Lys Lys
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: palmitoylated phospho-tau peptide
<220> FEATURE:
<221> NAME/KEY: palmitoylated lysine
<222> LOCATION: (1)..(1)
<220> FEATURE:
<221> NAME/KEY: palmitoylated lysine
<222> LOCATION: (2)..(2)
<220> FEATURE:
<221> NAME/KEY: phosphorylated serine
<222> LOCATION: (8)..(8)
<220> FEATURE:
<221> NAME/KEY: palmitoylated lysine
<222> LOCATION: (13)..(13)
<220> FEATURE:
<221> NAME/KEY: palmitoylated lysine
<222> LOCATION: (14)..(14)

<400> SEQUENCE: 38

Lys Lys Val Ser Gly Asp Thr Ser Pro Arg His Leu Lys Lys
1               5                   10

<210> SEQ ID NO 39
<211> LENGTH: 55
<212> TYPE: PRT
<213> ORGANISM: Artificial Sequence
<220> FEATURE:
<223> OTHER INFORMATION: T50 without the C-terminal amide

<400> SEQUENCE: 39

Ala Lys Phe Val Ala Ala Trp Thr Leu Lys Ala Ala Val Val Arg
1               5                   10                  15

Gln Tyr Ile Lys Ala Asn Ser Lys Phe Ile Gly Ile Thr Glu Leu Val
            20                  25                  30

Val Arg Phe Asn Asn Phe Thr Val Ser Phe Trp Leu Arg Val Pro Lys
        35                  40                  45

Val Ser Ala Ser His Leu Glu
    50                  55

<210> SEQ ID NO 40
<211> LENGTH: 53
<212> TYPE: PRT
<213> ORGANISM: Artificial Sequence
<220> FEATURE:
<223> OTHER INFORMATION: T46 without the palmitoylated lysines and
      C-terminal amide

<400> SEQUENCE: 40

Ala Lys Phe Val Ala Ala Trp Thr Leu Lys Ala Ala Ala Gly Ser Gln
1               5                   10                  15

Tyr Ile Lys Ala Asn Ser Lys Phe Ile Gly Ile Thr Glu Leu Gly Ser
            20                  25                  30

Phe Asn Asn Phe Thr Val Ser Phe Trp Leu Arg Val Pro Lys Val Ser
        35                  40                  45

Ala Ser His Leu Glu
    50

```
<210> SEQ ID NO 41
<211> LENGTH: 75
<212> TYPE: PRT
<213> ORGANISM: Artificial Sequence
<220> FEATURE:
<223> OTHER INFORMATION: T48 without the C-terminal amide

<400> SEQUENCE: 41

Ala Lys Phe Val Ala Ala Trp Thr Leu Lys Ala Ala Gly Ser Gln
1               5                   10                  15

Tyr Ile Lys Ala Asn Ser Lys Phe Ile Gly Ile Thr Glu Leu Gly Ser
            20                  25                  30

Phe Asn Asn Phe Thr Val Ser Phe Trp Leu Arg Val Pro Lys Val Ser
                35                  40                  45

Ala Ser His Leu Glu Gly Ser Leu Ile Asn Ser Thr Lys Ile Tyr Ser
    50                  55                  60

Tyr Phe Pro Ser Val Ile Ser Lys Val Asn Gln
65                  70                  75

<210> SEQ ID NO 42
<211> LENGTH: 53
<212> TYPE: PRT
<213> ORGANISM: Artificial Sequence
<220> FEATURE:
<223> OTHER INFORMATION: T51 without the C-terminal amide

<400> SEQUENCE: 42

Ala Lys Phe Val Ala Ala Trp Thr Leu Lys Ala Ala Arg Arg Gln
1               5                   10                  15

Tyr Ile Lys Ala Asn Ser Lys Phe Ile Gly Ile Thr Glu Leu Arg Arg
            20                  25                  30

Phe Asn Asn Phe Thr Val Ser Phe Trp Leu Arg Val Pro Lys Val Ser
                35                  40                  45

Ala Ser His Leu Glu
    50

<210> SEQ ID NO 43
<211> LENGTH: 53
<212> TYPE: PRT
<213> ORGANISM: Artificial Sequence
<220> FEATURE:
<223> OTHER INFORMATION: T52 without the C-terminal amide

<400> SEQUENCE: 43

Ala Lys Phe Val Ala Ala Trp Thr Leu Lys Ala Ala Arg Lys Gln
1               5                   10                  15

Tyr Ile Lys Ala Asn Ser Lys Phe Ile Gly Ile Thr Glu Leu Arg Lys
            20                  25                  30

Phe Asn Asn Phe Thr Val Ser Phe Trp Leu Arg Val Pro Lys Val Ser
                35                  40                  45

Ala Ser His Leu Glu
    50

<210> SEQ ID NO 44
<211> LENGTH: 57
<212> TYPE: PRT
<213> ORGANISM: Artificial Sequence
<220> FEATURE:
<223> OTHER INFORMATION: T57
<220> FEATURE:
<221> NAME/KEY: palmitoylated lysine
<222> LOCATION: (56)..(56)
```

```
<220> FEATURE:
<221> NAME/KEY: palmitoylated lysine
<222> LOCATION: (57)..(57)
<220> FEATURE:
<221> NAME/KEY: C-terminal amide
<222> LOCATION: (57)..(57)

<400> SEQUENCE: 44

Ala Lys Phe Val Ala Ala Trp Thr Leu Lys Ala Ala Ala Val Val Arg
1               5                   10                  15

Gln Tyr Ile Lys Ala Asn Ser Lys Phe Ile Gly Ile Thr Glu Leu Val
            20                  25                  30

Val Arg Phe Asn Asn Phe Thr Val Ser Phe Trp Leu Arg Val Pro Lys
        35                  40                  45

Val Ser Ala Ser His Leu Glu Lys Lys
    50                  55
```